US008646282B2

(12) United States Patent
Ilercil et al.

(10) Patent No.: US 8,646,282 B2
(45) Date of Patent: Feb. 11, 2014

(54) THERMO-ELECTRIC HEAT PUMP SYSTEMS

(76) Inventors: Alp Ilercil, Scottsdale, AZ (US); Tayfun Ilercil, Dana Point, CA (US)

( * ) Notice: Subject to any disclaimer, the term of this patent is extended or adjusted under 35 U.S.C. 154(b) by 184 days.

(21) Appl. No.: 13/146,635

(22) PCT Filed: Jan. 28, 2010

(86) PCT No.: PCT/US2010/022459
§ 371 (c)(1),
(2), (4) Date: Feb. 8, 2012

(87) PCT Pub. No.: WO2010/088433
PCT Pub. Date: Aug. 5, 2010

(65) Prior Publication Data
US 2012/0125014 A1 May 24, 2012

Related U.S. Application Data

(63) Continuation of application No. 12/361,484, filed on Jan. 28, 2009.

(60) Provisional application No. 61/148,911, filed on Jan. 30, 2009.

(51) Int. Cl.
*F25B 21/04* (2006.01)
(52) U.S. Cl.
USPC ......... 62/3.3; 62/3.1; 62/3.2; 62/3.6; 62/3.62; 62/371

(58) Field of Classification Search
USPC ....................... 62/3.1, 3.2, 3.3, 3.6, 3.62, 371
See application file for complete search history.

(56) References Cited

U.S. PATENT DOCUMENTS

| 6,959,555 B2 * | 11/2005 | Bell | 62/3.7 |
| 2006/0204950 A1 * | 9/2006 | Ilercil et al. | 435/1.1 |

* cited by examiner

*Primary Examiner* — Cheryl J Tyler
*Assistant Examiner* — Jonathan Bradford
(74) *Attorney, Agent, or Firm* — Rodney J. Fuller; Booth Udall Fuller, PLC

(57) ABSTRACT

The invention is directed to an energy efficient thermoelectric heat pump assembly. The thermoelectric heat pump assembly preferably comprises two to nine thermoelectric unit layers capable of active use of the Peltier effect; and at least one capacitance spacer block suitable for storing heat and providing a delayed thermal reaction time of the assembly. The capacitance spacer block is thermally connected between the thermoelectric unit layers. The present invention further relates to a thermoelectric transport and storage devices for transporting or storing temperature sensitive goods, for example, vaccines, chemicals, biologicals, and other temperature sensitive goods. Preferably the transport or storage devices are configured and provide on-board energy storage for sustaining, for multiple days, at a constant-temperature, with an acceptable temperature variation band.

20 Claims, 33 Drawing Sheets

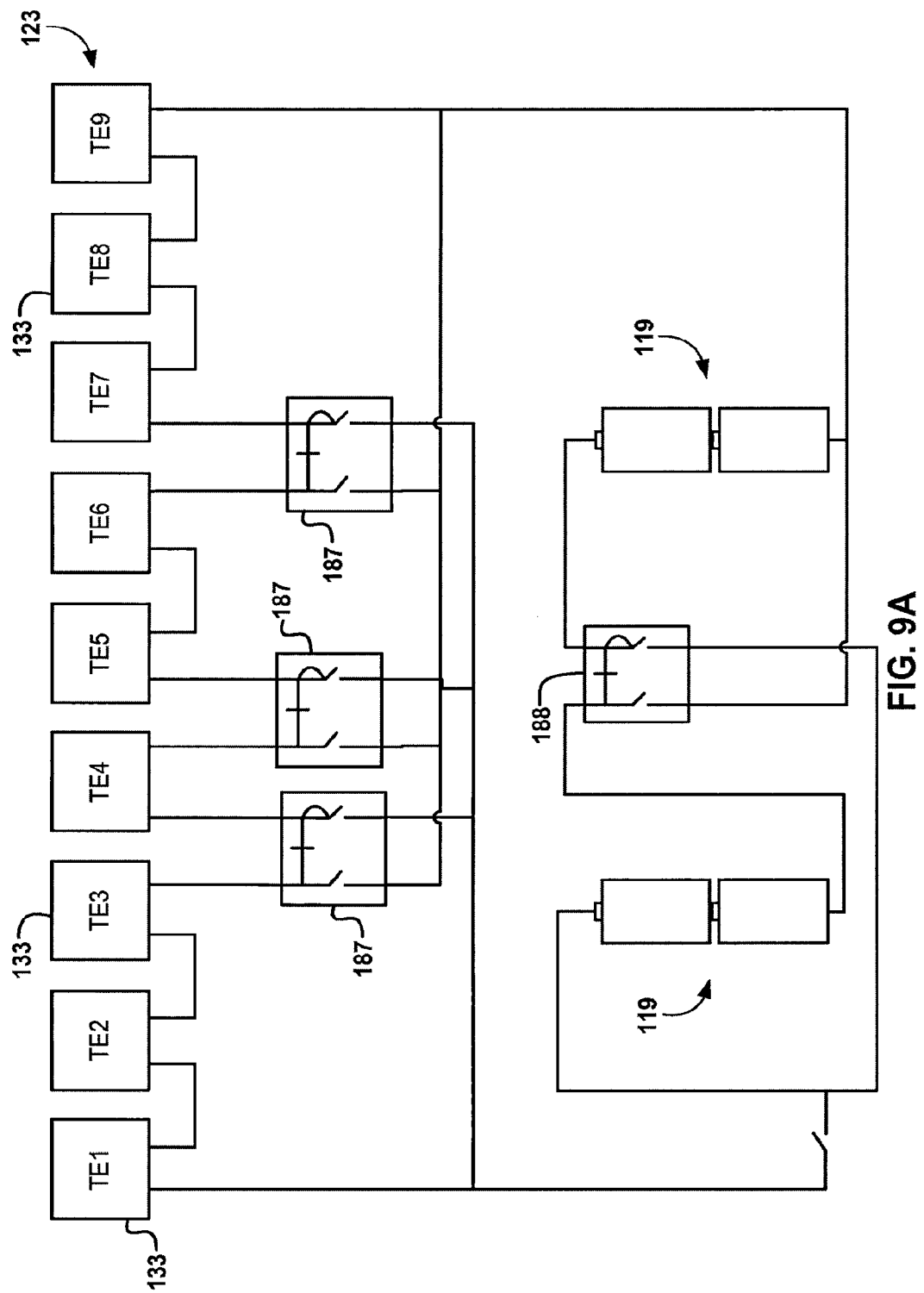

Option
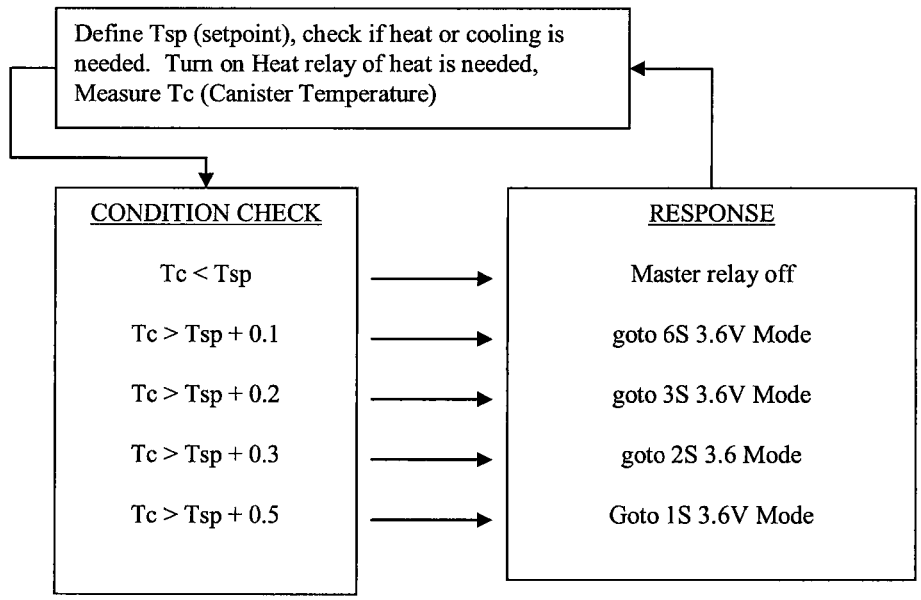
Option
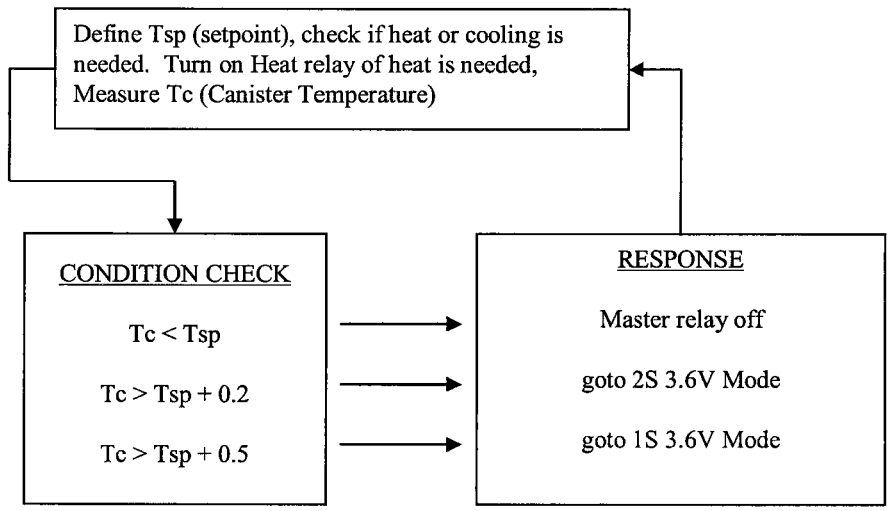
FIG. 18

| I max | DT max | Q | Delta T | V | I | I/Imax | DVDtmax | Couples | | DVDtmax / I/Imax | SL DVDtmax / MQ I/Imax |
|---|---|---|---|---|---|---|---|---|---|---|---|
| 2.1 | 67 | 0 | 40 | 5.53 | 0.57 | 0.271 | 0.597 | 127 | Single layer | 2.20 | 3.80 |
| 2.1 | 67 | 0 | 40 | 3.10 | 0.57 | 0.271 | 0.597 | 71 | Single layer | 2.20 | 3.80 |
| 2.1 | 67 | 0 | 40 | 2.75 | 0.57 | 0.271 | 0.597 | 63 | Single layer | 2.20 | 3.80 |
| 2.1 | 67 | 0 | 40 | 1.35 | 0.57 | 0.271 | 0.597 | 31 | Single layer | 2.20 | 3.80 |
| 2.1 | 67 | 0 | 40 | 0.75 | 0.57 | 0.271 | 0.597 | 17 | Single layer | 2.20 | 3.80 |
| 2.1 | 67 | 0 | 40 | 0.31 | 0.57 | 0.271 | 0.597 | 7 | Single layer | 2.20 | 3.80 |
| 2.1 | 67 | 0 | 24 | 3.16 | 0.33 | 0.157 | 0.358 | 127 | Micro Q | 2.28 | 2.28 |
| 2.1 | 67 | 0 | 20 | 2.60 | 0.27 | 0.129 | 0.299 | 127 | Single layer | 2.32 | 3.92 |
| 2.1 | 67 | 0 | 20 | 1.46 | 0.27 | 0.129 | 0.299 | 71 | Single layer | 2.32 | 3.92 |
| 2.1 | 67 | 0 | 20 | 1.29 | 0.27 | 0.129 | 0.299 | 63 | Single layer | 2.32 | 3.92 |
| 2.1 | 67 | 0 | 20 | 0.64 | 0.27 | 0.129 | 0.299 | 31 | Single layer | 2.32 | 3.92 |
| 2.1 | 67 | 0 | 20 | 0.35 | 0.27 | 0.129 | 0.299 | 17 | Single layer | 2.32 | 3.92 |
| 2.1 | 67 | 0 | 20 | 0.14 | 0.27 | 0.129 | 0.299 | 7 | Single layer | 2.32 | 3.92 |
| 2.1 | 67 | 0 | 12 | 1.53 | 0.16 | 0.076 | 0.179 | 127 | Micro Q | 2.35 | 2.35 |
| 2.1 | 67 | 0 | 10 | 1.27 | 0.14 | 0.067 | 0.149 | 127 | Single layer | 2.24 | 3.92 |
| 2.1 | 67 | 0 | 10 | 0.71 | 0.14 | 0.067 | 0.149 | 71 | Single layer | 2.24 | 3.92 |
| 2.1 | 67 | 0 | 10 | 0.63 | 0.14 | 0.067 | 0.149 | 63 | Single layer | 2.24 | 3.92 |
| 2.1 | 67 | 0 | 10 | 0.31 | 0.14 | 0.067 | 0.149 | 31 | Single layer | 2.24 | 3.92 |
| 2.1 | 67 | 0 | 10 | 0.17 | 0.14 | 0.067 | 0.149 | 17 | Single layer | 2.24 | 3.92 |
| 2.1 | 67 | 0 | 10 | 0.07 | 0.14 | 0.067 | 0.149 | 7 | Single layer | 2.24 | 3.92 |
| 2.1 | 67 | 0 | 6 | 0.77 | 0.08 | 0.038 | 0.090 | 127 | Micro Q | 2.35 | 2.35 |

| Control T | Cap T | Dt | V | I | Qc | I/Imax | DVDtmax | Qh | | | |
|---|---|---|---|---|---|---|---|---|---|---|---|
| -12.7 | 10.9 | 23.6 | 3.7 | 0.46 | 1.08 | 0.219 | 0.352 | 2.78 | 1S Mode | | |
| 10.6 | 26.4 | 15.8 | 3.7 | 0.47 | 3.42 | 0.224 | 0.236 | 5.18 | Cold layer | | |
| | | 39.4 | | | | | | | Hot layer | | |

| Control T | Cap T | Dt | V | I | Qc | I/Imax | DVDtmax | Qh | | | |
|---|---|---|---|---|---|---|---|---|---|---|---|
| 3 | 15.1 | 12.1 | 1.84 | 0.21 | 0.68 | 0.100 | 0.181 | 1.07 | 2S Mode | | |
| 14.9 | 23.7 | 8.8 | 1.84 | 0.23 | 1.65 | 0.110 | 0.131 | 2.07 | Cold layer | | |
| | | 20.9 | | | | | | | Hot layer | | |

FIG. 28A

| I max | DT max | Q | Delta T | V | I | I/Imax | Dt/Dtmax | Couples | |
|---|---|---|---|---|---|---|---|---|---|
| 2.1 | 67 | 1 | 40 | 6.12 | 0.66 | 0.314 | 0.597 | 127 | Single layer |
| 2.1 | 67 | 1 | 40 | 3.70 | 0.74 | 0.352 | 0.597 | 71 | Single layer |
| 2.1 | 67 | 1 | 40 | 3.36 | 0.77 | 0.367 | 0.597 | 63 | Single layer |
| 2.1 | 67 | 1 | 40 | 2.03 | 1.02 | 0.486 | 0.597 | 31 | Single layer |
| 2.1 | 67 | 1 | 40 | 1.60 | 1.61 | 0.767 | 0.597 | 17 | Single layer |
| 2.1 | 67 | N/A | N/A | N/A | N/A | N/A | N/A | 7 | Single layer |
| 2.1 | 67 | 1 | 24 | 3.66 | 0.42 | 0.200 | 0.358 | 127 | Micro Q top layer |
| 2.1 | 67 | 0.5 | 20 | 2.83 | 0.31 | 0.148 | 0.299 | 127 | Single layer |
| 2.1 | 67 | 0.5 | 20 | 1.70 | 0.35 | 0.167 | 0.299 | 71 | Single layer |
| 2.1 | 67 | 0.5 | 20 | 1.53 | 0.36 | 0.171 | 0.299 | 63 | Single layer |
| 2.1 | 67 | 0.5 | 20 | 0.89 | 0.45 | 0.214 | 0.299 | 31 | Single layer |
| 2.1 | 67 | 0.5 | 20 | 0.61 | 0.61 | 0.290 | 0.299 | 17 | Single layer |
| 2.1 | 67 | 0.5 | 20 | 0.46 | 1.26 | 0.600 | 0.299 | 7 | Single layer |
| 2.1 | 67 | 0.5 | 12 | 1.75 | 0.20 | 0.095 | 0.179 | 127 | Micro Q top layer |
| 2.1 | 67 | 0.25 | 10 | 1.38 | 0.16 | 0.076 | 0.149 | 127 | Single layer |
| 2.1 | 67 | 0.25 | 10 | 0.82 | 0.17 | 0.081 | 0.149 | 71 | Single layer |
| 2.1 | 67 | 0.25 | 10 | 0.74 | 0.17 | 0.081 | 0.149 | 63 | Single layer |
| 2.1 | 67 | 0.25 | 10 | 0.43 | 0.22 | 0.105 | 0.149 | 31 | Single layer |
| 2.1 | 67 | 0.25 | 10 | 0.29 | 0.29 | 0.138 | 0.149 | 17 | Single layer |
| 2.1 | 67 | 0.25 | 10 | 0.20 | 0.55 | 0.262 | 0.149 | 7 | Single layer |
| 2.1 | 67 | 0.25 | 6 | 0.86 | 0.10 | 0.048 | 0.090 | 127 | Micro Q top layer |
| Control T | Cap T | Dt | V | — | Qc | I/Imax | Dt/Dtmax | Qh | 1S Mode |
| -12.7 | 10.9 | 23.6 | 3.7 | 0.46 | 1.08 | 0.219 | 0.352 | 2.78 | Top layer |
| 10.6 | 26.4 | 15.8 | 3.7 | 0.47 | 3.42 | 0.224 | 0.236 | 5.18 | Bottom layer |
|  |  | 39.4 |  |  |  |  |  |  |  |
| Control T | Cap T | Dt | V | — | Qc | I/Imax | Dt/Dtmax | Qh | 2S Mode |
| 3 | 15.1 | 12.1 | 1.84 | 0.21 | 0.68 | 0.100 | 0.181 | 1.07 | Top layer |
| 14.9 | 23.7 | 8.8 | 1.84 | 0.23 | 1.65 | 0.110 | 0.131 | 2.07 | Bottom layer |
|  |  | 20.9 |  |  |  |  |  |  |  |

FIG. 28B

Micro Q operating point at DT20

Typical TE operating point at DT 40

Optimum TE operating point at DT 40

Micro Q operating point at DT40

THERMO-ELECTRIC HEAT PUMP SYSTEMS

CROSS-REFERENCE TO RELATED APPLICATIONS

This application is the U.S. National Stage of PCT/US2010/022459, filed Jan. 28, 2010, entitled "THERMO-ELECTRIC HEAT PUMP SYSTEMS", which is a continuation of U.S. patent application Ser. No. 12/361,484, filed Jan. 28, 2009, entitled "THERMO-ELECTRIC HEAT PUMP SYSTEMS", and which claims the benefit of U.S. Provisional Application No. 61/148,911, filed Jan. 30, 2009, entitled "THERMO-ELECTRIC HEAT PUMP SYSTEMS", the contents of each of which are incorporated herein by reference thereto.

BACKGROUND

This invention relates to thermo-electric heat pump systems. In another aspect, this invention relates to providing a system for improved iso-thermal transport and storage systems. More particularly, this invention relates to providing a system for temperature regulation for transported materials requiring a stable thermal environment. There is a need for a robust shock-proof and efficient thermo-electric device that is self-sufficient and does not require external power for a period of multiple days. Further, there is a need for a thermo-electric device that is capable of safely storing and maintaining its cargo during transport and/or storage. The need for such an invention has been expressed by those involved in transportation and storage of temperature sensitive and delicate goods, for example, biological or laboratory samples. Additionally, this need is further expressed by those responsible for transporting sensitive goods in extreme locations where temperature regulation may be problematic. Furthermore, a need exists for an iso-thermal storage and transport system that self-regulates temperature over pre-defined, adjustable cooling or heating profiles. Shipping weight and volume are also prime concerns.

A need exists for an iso-thermal storage and transport system that provides a self-contained means for storing energy onboard during the transport and storage of sensitive goods, such as biological materials and samples, including cell and tissue cultures, nucleic acids, bodily fluids, tissues, organs, embryos, semen, stem-cells, ovaries, platelets, blood, plant tissues, and other sensitive goods such as pharmaceuticals, vaccines and chemicals. In light of available utilities, external ambient temperature, environmental conditions and other factors, it is essential that an iso-thermal storage and transport system function reliably to protect sensitive goods from degradation.

A need exists for an iso-thermal storage and transport system that is robust and that provides a shock-proof system that withstands abuses and rough handling inherent within storage and transportation of sensitive goods.

Further, needs exist for iso-thermal storage and transport systems and other related thermo-electric heat pump systems that are reusable, reliable over an extended time period, cost-effective and dependable.

OBJECTS AND FEATURES OF THE INVENTION

A primary object and feature of the present invention is providing a reliable, efficient iso-thermal system for protecting sensitive goods during storage and transport.

Another object and feature of the present invention is providing a reliable, efficient iso-thermal system having high coefficients of performance (hereinafter "COP") for efficient performance for protecting sensitive goods during storage and transport.

A further object and feature of the present invention is making streamlined use of the thermo-electric effect (the direct conversion of temperature differences to electric voltage), and conversely, converting electric voltage to temperature differences for protecting sensitive goods during storage and transport.

Another object and feature of the present invention is making a convenient and accurate temperature controller wherein heat may be pumped, either into or out of a vessel, so as to maintain temperature consistency within the vessel for protecting sensitive goods during storage and transport.

Yet another object and feature of the present invention is utilizing the Seebeck and Peltier principles for protecting sensitive goods during storage and transport.

Another object and feature of the present invention is minimizing shipping volume and weight while functionally providing needed temperature regulation for protecting sensitive goods during storage and transport.

Yet another object and feature of the present invention is providing a high degree of efficiency and reliability for protecting sensitive goods during storage and transport.

Another object and feature of the present invention is providing an iso-thermal storage and transport system that self-regulates temperature over pre-defined, adjustable cooling or heating profiles.

Another object and feature of the present invention is providing onboard stored energy, such as direct-current rechargeable batteries and recharging system, for supplying required power for protecting sensitive goods during storage and transport.

Another object and feature of the present invention is method of engineering design of thermo-electric heat pumps, relating to designing toward maximizing heat pumped per unit of input power.

Another object and feature of the present invention is method of engineering design of thermo-electric heat pumps, relating to designing toward maximizing heat pumped per unit of input power, applied to shipping perishables.

Another object and feature of the present invention is method of engineering design of thermo-electric heat pumps, relating to designing toward heat removal requirements of a specific use so as to reduce power requirements.

Another object and feature of the present invention is method of engineering design of thermo-electric heat pumps, relating to designing toward maximizing heat pumped per unit of input power, providing temperature conditioning of perishables in recreational vehicles, including marine vehicles.

Another object and feature of the present invention is method of engineering design of thermo-electric heat pumps, relating to designing toward maximizing heat pumped per unit of input power, protectively transporting reproductive biological material, including equine semen, bovine semen, or other mammalian reproductive biological material.

SUMMARY OF THE INVENTION

The present invention is directed to a thermoelectric heat pump assembly having a more efficient design. As used herein, Temperature (T) is in Celsius; Voltage (V) is in Volts; current (I) is in Amps; heat (Q) is in Watts; and resistance R is in Ohms. The heat pump assembly designs described herein increases heat pump per unit of input power during overall use, with increased reliability. In a preferred embodiment the thermoelectric heat pump assembly comprises: two or more thermoelectric unit layers (i.e., thermoelectric modules) capable of active use of the Peltier effect, each thermoelectric unit layer having a cold side and a hot side, and at least one capacitance spacer block suitable for storing heat and providing a delayed thermal reaction time of the assembly.

Preferably, the heat pump assembly of the invention is configured so that each thermoelectric unit layer at steady-state during operation has ratio of the heat removed divided by the input power (COP) that is prior to and less than the peak COP on a COP curve of performance (See FIGS. 29A-C and 30A-C). The capacitance spacer block has a top portion and a bottom portion and is between a first thermoelectric unit layer and a second thermoelectric layer. The top portion of the capacitance spacer block is thermally connected to the hot side of the first thermoelectric unit layer and the bottom portion is thermally connected to the cold side of the second thermoelectric unit layer, forming a sandwich layer suitable to pump heat from the first thermoelectric unit layer to the second thermoelectric layer. Preferably, the capacitance spacer block is made of copper, aluminum, or other thermally conductive and capacitive alloys.

Each thermoelectric unit layer preferably comprises thermoelectric units electrically connected in parallel or series, but thermally connected in series. Preferably, each thermoelectric unit layer in the heat pump assembly is separated by a capacitance spacer block. In preferred configurations, the thermoelectric heat pump of the invention would have two to nine thermoelectric unit layers (e.g., 2, 3, 4, 5, 6, 7, 8, 9). The thermoelectric unit layers are preferably electrically reconfigurably connected to maintain a preferred temperature profile over time by switching between different configurations, e.g., electrically reconfigurable between series and parallel configurations.

At least one energy source (e.g., battery) is operably connected to each thermoelectric unit layer, wherein the energy source is suitable to provide a current to power the thermoelectric heat pump and to control the amount of heat removed by the heat pump. In certain aspects of the invention, the heat pump assembly comprises two or more energy sources (e.g., 3, 4, 5) that can be used as back up or provide alternative current configurations.

Advantageously, the heat pump assembly typically also has a heat sink associated with a fan assembly, wherein in the heat sink is thermally connected at the bottom end of the heat pump assembly. In certain aspects of the invention, the heat sink is at least 30 W, more preferably at least 40 W (e.g., 45 W, or 50 W).

In one aspect of the invention, the heat pump assembly is configured so that each individual thermoelectric unit layer has a ratio of input current to maximum available current (I/Imax) of 0.35 at steady-state. More preferably the heat pump assembly is configured so that the I/Imax of 0.09 or less (e.g. 0.076) at a steady-state, when change in temperature ($\Delta T$) of the heat pump assembly at the top end compared to the bottom end of the heat pump assembly is about 20° C. and heat removal (Q) is about 0 Watts; and/or the ratio of input current to maximum available current (I/Imax) of each individual thermoelectric unit layer is 0.18 or less at a steady-state, when change in temperature ($\Delta T$) of the heat pump assembly at the top end compared to the bottom end of the heat pump assembly is about 40° C. and heat (Q) is about 0 Watts.

In another aspect of the invention, the heat pump assembly is configured so that each individual thermoelectric unit layer has a maximum change in temperature ($\Delta T$max) potential and comprises at least 127 coupled pairs of thermoelectric units, and wherein the heat pump assembly is configured so that each thermoelectric layer operates at: (i) less than 20% of the $\Delta T$max at steady-state when change in temperature ($\Delta T$) of the heat pump assembly at the top end compared to the bottom end of the heat pump assembly is about 20° C.; and/or (ii) less than 40% of the $\Delta T$max at steady-state when change in temperature ($\Delta T$) of the heat pump assembly at the top end compared to the bottom end of the heat pump assembly is about 40° C.

In another aspect of the invention, the heat pump assembly further comprises a heat sink associated with a fan assembly, wherein in the heat sink is thermally connected at the bottom end of the heat pump assembly, the heat pump assembly being configured to minimize a temperature rise or drop on the heat sink at a steady-state so that the temperature rise or drop on the heat sink does not exceed 5° C., more preferably it does not exceed 4° C. or 3° C., and most preferably 2.5° C., typically as compared to ambient temperature.

In a preferred configuration, the thermoelectric heat pump assembly is configured so that at steady-state the heat sink has a temperature that does not exceed 30%, more preferably 25% or 20%, of the heat sink maximum temperature rating, wherein the heat sink has a rating of at least 35 Watts (e.g., 40 Watts).

It is preferred that each thermoelectric unit layer comprise at least 127 coupled pairs of thermoelectric units. Also, is preferable that each thermoelectric unit layer is 3 or more Ohms at 25° Celsius, more preferably 5 or more Ohms, (e.g. about 5.5, 6.0, or 6.5 Ohms), typically not greater than 7.5 Ohms. The preferred thermoelectric unit layer (i.e., a thermoelectric module) has a heat pumping capability of between 15 Watts and 20 Watts.

Preferably, each thermoelectric unit layer has a maximum change in temperature ($\Delta T$max) potential and is configured so that each thermoelectric layer operates at less than 20% of the $\Delta T$max at steady-state when change in temperature ($\Delta T$) of the heat pump assembly at the top end compared to the bottom end of the heat pump assembly is 20° C.; and/or operates at less than 40% of the $\Delta T$max at steady-state when change in temperature ($\Delta T$) of the heat pump assembly at the top end compared to the bottom end of the heat pump assembly is 40° C.

In addition, preferably the capacitance spacer block typically separates the thermoelectric unit layers by at least ¼ inch, more preferably at least about ½, 1, 2, or 3 inches. In a specific design of the invention, the capacitance spacer block, is about 1.5-2.5 inches. Preferably, the top portion and bottom portion of the capacitance spacer block is substantially the same size and shape as the cold side and hot side of each thermoelectric unit layer to obtain substantial contact with the thermoelectric unit layer.

The thermoelectric heat pump assembly of the invention may further comprise momentary relay based circuitry, preferably programmable by a portable microprocessor adapted to control the temperature of the temperature sensitive goods based on a preferred temperature profile. In a preferred embodiment of the invention, the thermoelectric heat pump assembly further comprises a microcontroller (e.g., microprocessor) operatively associated with the energy source and at least one relay, wherein the microcontroller activates the at least one relay which directs current from the energy source to at least one of the thermoelectric unit layers and wherein the at least one relay reconnects the at least one thermoelectric unit layer in series or parallel with another thermoelectric unit layer.

For example, the microcontroller: (1) defines a setpoint temperature (Tsp) and compares the Tsp to a temperature (Tc)

of a container operatively associated with the thermoelectric heat pump assembly, wherein the microcontroller controls at least one relay to connect the at least one thermoelectric unit layer in series if Tc checks positive or equal against Tsp, and wherein the microcontroller deactivates the at least one relay if Tsp checks negative or equal against Tc; (2) defines a Tsp and compares the Tsp to Tc of a container operatively associated with the thermoelectric heat pump assembly, wherein the microcontroller activates the at least one relay to connect the at least one thermoelectric unit layer in parallel if Tc checks positive or equal against Tsp, and wherein the microcontroller deactivates the at least one relay if Tsp checks negative or equal against Tc; and/or (3) defines a Tsp and compares the Tsp to a Tc of a container operatively associated with the thermoelectric heat pump assembly, wherein the microcontroller activates the at least one relay to connect the at least one thermoelectric unit layer in parallel and the microcontroller activates the at least one relay to connect the at least one thermoelectric unit layer in series if Tsp checks positive or equal against Tc, and wherein the microcontroller deactivates the at least one relay if Tsp checks negative or equal against Tc. In a specific example, the Tc would check positive or equal if the Tc is greater than the Tsp plus 1° C., more preferably 0.5° C., or a most preferably 0.1° C.

The invention is further directed to a thermoelectric transport or storage device for thermally protecting temperature sensitive goods during transport. Preferably the thermoelectric transport and storage device is configured so that it self-regulates temperature over pre-defined, adjustable cooling or heating profile. Advantageously, the device comprises a thermal isolation chamber for storing the temperature sensitive goods and at least one thermoelectric heat pump assembly, as described herein, thermally connected to the thermal isolation chamber and configured to control a temperature of the temperature sensitive goods during transport or storage at a selected steady-state temperature within a tolerable temperature variation for the temperature sensitive goods being transported or stored. Preferably the thermal isolation chamber is made of thermally conductive metals and alloys, e.g., aluminum.

Non-limiting examples of temperature-sensitive goods suitable for transport in the device include: semen, embryos, oocytes, cell cultures, tissue cultures, chondrocytes, nucleic acids, bodily fluids, organs, plant tissues, pharmaceuticals, vaccines, and temperature-sensitive chemicals. In a preferred embodiment the thermoelectric transport or storage device also has a robust shock proof exterior, capable of protecting sensitive goods during long periods of transport and storage.

In certain aspects of the invention, the transport or storage device typically also has a portable microprocessor, wherein the portable microprocessor is programmed to communicate with the thermoelectric transport or storage device upon activation. In addition, the device may also advantageously have an electrical-erasable-programmable read-only-memory (EEPROM) chip operatively associated with the thermoelectric transport or storage device. The EEPROM chip communicates with the portable microprocessor and the thermoelectric heat pump. The portable microprocessor also typically communicates with the EEPROM chip through a multi-master serial computer bus using I2C protocol and preferably stores received time and temperature profiles related to the thermoelectric heat pump assembly.

In one exemplary configuration, the portable microprocessor communicates time and temperature profiles related to the thermoelectric heat pump to the EEPROM and also receives time and temperature profiles related to the thermoelectric heat pump from the EEPROM. Preferably the portable microprocessor stores the received time and temperature profiles related to the thermoelectric heat pump. Also, the portable microprocessor is preferably operatively associated with the thermoelectric transport or storage device through one or more DB connectors. In this exemplary embodiment, the portable microprocessor is often advantageously activated by the energy source of the thermoelectric transport or storage device.

The thermoelectric transport or storage device described herein, also preferably comprises reconfigurable circuitry suitable for a selected temperature input. In this embodiment, the thermoelectric unit layers are electrically reconfigurable to maintain a temperature profile during transport or storage. Typically, the circuitry comprises a programmable microprocessor programmed to actuate a temperature sensitive goods specific temperature profile.

The thermoelectric transport or storage device also preferably has at least one rotator structured and arranged to rotate the temperature sensitive goods within the thermal isolation chamber. This facilitates a uniform temperature of the goods during transport and enhances the effectiveness of maintaining the desired temperature.

The thermoelectric transport or storage device is also preferably configured to configured to control the temperature of the temperature sensitive goods within a selected tolerance for a specific temperature sensitive good, for example, a tolerance of less than about 10° C., more preferably less than: 8° C.; 5° C.; and/or 3° C.; and most preferably less than: 1° C., 0.5° C. and/or 0.1° C.

Another aspect of the invention is the ability to program the thermoelectric transport or storage device with unique specific profiles suitable for the specific goods being transported and the needs of the users. For example, the device can be programmed to ship reproductive fluids at a selected and desired temperature to best preserve the fluids using very low tolerance variability levels of 0.1° C., until delivery, at which the device would be programmed to increase to a second selected and desired the temperature for clinical use.

Also with extremely sensitive temperature goods it is important to have a ramp down and/or ramp down period so as not to harm the goods due to a rapid change in temperature. To ramp down/up the temperature, the device can be programmed or configured to gradually increase or decrease the temperature over a set time period. For example, the device could be programmed to decrease/increase the temperature by 0.1 degrees every 20 minutes, down to a selected temperature. Thus, as can be seen, the device of the invention provides the user with the ability to specifically program the device with not just one profile, but with several temperature profiles (or sub-profiles), e.g., 3, 4, 5, etc. in accordance with parameters of the goods to be stored or transported. The activation of sub-profiles allows for increased flexibility in best protecting the specific temperature sensitive goods during transport.

The thermoelectric transport or storage device advantageously has at least one portable energy source, e.g. at least one, two, or three batteries, which is suitable to maintain the selected temperature for the temperature sensitive goods during transport of at least 72 hours, more preferably at least 84 hours, and even 7 days, the selected temperature of the temperature sensitive goods compared to ambient temperature is at least 20° C., at least 30° C. or at least 40° C. Multiple batteries can be used to provide the necessary energy source.

Another important aspect of the invention is the insulation. The insulation preferably one or more vacuum insulators insulating the thermal isolation chamber. Preferred vacuum insulators comprise at least one layer of reflective material having infrared emittance, in the infrared spectrum from about one micron to about one millimeter wavelength, of less than about 0.1. Even more preferred, the vacuum insulators also preferably comprise at least one evacuated volume having an absolute pressure of less than about 10 Torr.

The thermoelectric transport or storage devices described herein can come in many sizes and shapes, e.g., 1'×2'; 4'×4', etc. As the sizes of the transport or storage device increase it is preferably that at least 2 thermoelectric heat pumps be incorporated therein (4, 8, 10, 15, etc.). The heat pumps are preferably reconfigurably connected between series and parallel configurations. Furthermore, the thermoelectric unit layers of each heat pump is also preferably reconfigurably connected between series and parallel providing greater control over the amount of heat generation of each thermoelectric unit layer and the heat pump in general.

The invention is also directed to a method of safely transporting temperature sensitive goods at a selected temperature profile during transport. The method preferably comprises the steps of:

(a) placing the temperature sensitive goods in a transportation device adapted to thermally isolate the temperature sensitive goods from outside environment, wherein the transportation device comprises at least one temperature control system adapted to actuate the selected temperature profile while the temperature sensitive goods are in the transportation device, the temperature control system comprising at least one thermoelectric heat pump as described above in thermal association with the temperature sensitive goods being transported; and (b) transporting the temperature sensitive goods while the transportation device is activated according to the selected temperature profile.

In certain embodiment, the invention further comprises loading a user-selected temperature profile specific to the temperature sensitive goods being transported by inserting a smart chip into a communication link, wherein the smart chip downloads the profile into the transport device.

In accordance with a other preferred embodiments hereof, this invention provides a thermal protection system, relating to thermally protecting temperature-sensitive goods, comprising: at least one thermo-electric heat pump adapted to control at least one temperature of the temperature-sensitive goods; wherein such at least one thermo-electric heat pump comprises at least one thermo-electric device adapted to active use of the Peltier effect; wherein such at least one thermo-electric heat pump comprises at least one thermal capacitor adapted to provide at least one thermal capacitance in thermal association with such at least one thermo-electric device; and wherein such at least one thermal capacitance is user-selected to provide intended thermal association with such at least one thermo-electric device, and wherein such at least one thermal capacitance is preferably embodied by a capacitance spacer block made of, for example, aluminum, copper, or other thermally conductive and capacitive alloys. Moreover, it provides such a thermal protection system: wherein such intended thermal association of such at least one least one thermal capacitance is user-selected to provide increased energy efficiency of operation of such at least one thermo-electric device as compared to such energy efficiency of operation of such at least one thermo-electric device without addition of such at least one least one thermal capacitor.

Additionally, it provides such a thermal protection system: wherein such intended thermal association of such at least one thermal capacitance is user-selected to allow usage of momentary-relay-based control circuitry in combination with at least one energy store to power such at least one thermo-electric device to achieve control of at least one temperature of the temperature-sensitive goods. Also, it provides such a thermal protection system: wherein such control of such at least one temperature comprises controlling such at least one temperature to within a tolerance of less than about one degree centigrade. In addition, it provides such a thermal protection system: wherein such intended thermal association is user-selected to control usage of proportional control circuitry in combination with at least one energy store to power such at least one thermo-electric heat pump to control such at least one temperature of the temperature-sensitive goods. And, it provides such a thermal protection system: wherein such control of such at least one temperature comprises controlling such at least one temperature to within a tolerance of less then one degree centigrade. Further, it provides such a thermal protection system: wherein such at least one thermo-electric heat pump comprises a minimum of one sandwich layer; wherein such sandwich layer comprises at least one set of such thermo-electric devices and at least one set of such thermal capacitors; wherein each such sandwich layer is suitable for thermally-conductively connecting to at least one other such sandwich layer; and wherein thermal conductance between essentially all such attached sandwich layers is greater than 10 watts per meter per degree centigrade.

Even further, it provides such a thermal protection system: wherein such at least one thermo-electric heat pump comprises at least one such sandwich layer comprising such set of such thermo-electric devices; wherein each thermo-electric device comprising such plurality is electrically connected in parallel with each other each thermo-electric device comprising such plurality; and wherein each set of such thermoelectric devices comprising such first sandwich layer is suitable for thermally-conductively connecting to at least one other such sandwich layer; and wherein thermal conductance between essentially all such attached sandwich layers is greater than 10 watts per meter per degree centigrade.

Moreover, it provides such a thermal protection system further comprising: at least one thermal isolator for thermally isolating the temperature sensitive goods. Additionally, it provides such a thermal protection system: at least one thermal isolator for thermally isolating the temperature sensitive goods, wherein such at least one thermal isolator comprises at least one vessel structured and arranged to contain the temperature sensitive goods; and wherein such at least one vessel comprises at least one heat-transferring surface structured and arranged to conductively exchange heat to and from such at least one temperature controller.

Also, it provides such a thermal protection system: wherein such at least one vessel comprises at least one re-sealable surface structured and arranged to ingress and egress the temperature sensitive goods to and from such at least one thermal isolator. In addition, it provides such a thermal protection system: wherein such at least one re-sealable surface comprises at least one seal structured and arranged to exclude at least one microorganism from such at least one vessel. And, it provides such a thermal protection system: wherein such at least one thermal isolator comprises at least one insulator for insulating the temperature sensitive goods. Further, it provides such a thermal protection system: wherein such at least one insulator comprises at least one layer of reflective material; and wherein infrared emittance of such reflective material is less than about 0.1, in the infrared spectrum from about one micron to about one millimeter wavelength.

Even further, it provides such a thermal protection system: wherein such at least one insulator comprises at least one evacuated volume; and wherein absolute pressure of such least one evacuated volume is less than about 10 Torr. Moreover, it provides such a thermal protection system: wherein such at least one thermal isolator comprises at least one goods rotator structured and arranged to rotate the temperature sensitive goods within such at least one thermal isolator. Additionally, it provides such a thermal protection system: wherein such at least one goods rotator is structured and arranged to self-power from at least one energy storage device.

Also, it provides such a thermal protection system: wherein such at least one energy storage device comprises at least one battery. In addition, it provides such a thermal protection system: wherein such thermo-electric heat pump comprises from about two to about nine vessel sandwich layers, each such vessel sandwich layer comprising at least one vessel set of such thermo-electric devices; and wherein such at least one vessel set comprises at least two thermo-electric devices. And, it provides such a thermal protection system: wherein such at least one vessel set comprises at least ten thermo-electric devices.

In accordance with another preferred embodiment hereof, this invention provides a method, relating to use of at least one thermal protection system, relating to thermally protecting temperature-sensitive goods, comprising the steps of: delivery, by at least one provider, of such at least one thermal protection system to at least one user, relating to at least one use, relating to at least one time period; wherein such at least one thermal protection system comprises at least one thermo-electric device adapted to active use of the Peltier effect to effect such control of at least one temperature; wherein such at least one thermo-electric device comprises at least one thermal capacitor adapted to provide at least one thermal capacitance in thermal association with such at least one thermo-electric device; and wherein such at least one thermal capacitor is user-selected to provide intended thermal association with such at least one thermo-electric device presetting of at least one set-point temperature of such at least one thermal protection system, by such at least one provider, prior to such delivery; and receiving value from at least one party benefiting from such at least one use. Further, it provides such a method, further comprising: providing re-use of such at least one thermal protection system, by such at least one provider; wherein such step of providing re-use comprises at least one cleaning step, and at least one set-point re-setting step. Even further, it provides such a method, further comprising: permitting other entities, for value, to provide such method.

In accordance with another preferred embodiment hereof, this invention provides a method of engineering design of thermo-electric heat pumps, relating to designing toward maximizing heat pumped per unit of input power, comprising the steps of: accumulating at least one desired range of variables for each at least one design-goal element of such thermoelectric heat pump to be designed; discovering such maximum heat pumped per unit of input power; and finalizing such engineering design; wherein such step of discovering such maximum heat pumped per unit of input power comprises providing at least one desired arrangement of a plurality of thermo-electric devices, wherein essentially each thermo-electric device of such plurality of thermo-electric devices is associated with at least one user selectable thermal capacitance, holding each such at least one design-goal element within a respective such at least one desired range of variables, incrementally trial raising each such at least one user selectable thermal capacitance while performing such holding step, and essentially maximizing such at least one user selectable thermal capacitance while remaining within each respective such at least one desired range of variables; wherein at least one essentially maximum heat pumped per unit of input power may be achieved.

In accordance with another preferred embodiment hereof, this invention provides a method, applied to shipping perishables: wherein such design-goal elements comprising ambient temperature, shipping container cost, shipping container weight, shipping container size, maximum variation of temperature of perishables required; wherein the shipping container cost, shipping container weight, shipping container size, variation of temperature of perishables are minimized while achieving essentially maximum heat pumped per unit of input power; wherein such shipping container comprises at least one arrangement of a plurality of thermo-electric devices; wherein essentially each thermo-electric device of such plurality of thermo-electric devices is associated with at least one user selectable thermal capacitance; wherein thermal capacitance of each such at least one user selectable thermal capacitance is determined by holding each such at least one design-goal element within a respective such at least one desired range of variables, incrementally trial raising each such at least one user selectable thermal capacitance while performing such holding step, and essentially maximizing such at least one user selectable thermal capacitance while remaining within each respective such at least one desired range of variables; and wherein at least one essentially maximum heat pumped per unit of input power is achieved.

In accordance with another preferred embodiment hereof, this invention provides a method, applied to providing temperature conditioning of perishables in recreational vehicles: wherein such design-goal elements comprise ambient temperature, perishable cold storage container cost, perishable cold storage container weight, perishable cold storage container size, maximum variation of temperature of perishables required; wherein the cold storage container cost, perishable cold storage container weight, perishable cold storage container size, variation of temperature of perishables are minimized while achieving essentially maximum heat pumped per unit of input power; wherein such shipping container comprises at least one arrangement of a plurality of thermo-electric devices; wherein essentially each thermo-electric device of such plurality of thermo-electric devices is associated with at least one user selectable thermal capacitance; wherein thermal capacitance of each such at least one user selectable thermal capacitance is determined by holding each such at least one design-goal element within a respective such at least one desired range of variables, incrementally trial raising each such at least one user selectable thermal capacitance while performing such holding step, and essentially maximizing such at least one user selectable thermal capacitance while remaining within each respective such at least one desired range of variables; and wherein at least one essentially maximum heat pumped per unit of input power is achieved.

In accordance with another preferred embodiment hereof, this invention provides a method, relating to protectively transporting equine semen, comprising the steps of: providing at least one transportation vessel adapted to seal such horse semen in isolation from outside environment; providing at least one temperature control system adapted to control temperature of the horse semen while in such at least one transportation vessel; and providing that such at least one temperature control system comprises at least one thermo-electric heat pump; wherein such at least one thermo-electric heat pump is adapted to controlling temperature of such horse semen to remain in at least one temperature range assisting viability of such horse semen. Moreover, it provides such a method wherein such at least one thermo-electric heat pump comprises at least one Peltier thermo-electric device in thermal association with at least one thermal capacitor having at least one thermal capacitance designed to provide intended to provide intended operational features of such at least one thermo-electric heat pump.

And it provides for each and every novel feature, element, combination, step and/or method disclosed or suggested by this provisional patent application.

BRIEF DESCRIPTION OF THE FIGURES

FIG. 9A shows an electrical schematic view, illustrating electrical control of the iso-thermal transport and storage system, according to the preferred embodiment of FIG. 1.

FIG. 18 shows a schematic view of a control logic diagram of a preferred embodiment of the invention.

FIGS. 28A-B show charts, each of which illustrate how preferred embodiments of the present invention are configured to maximize efficiency of operation compared to previously available thermoelectric heat pump systems; the charts further illustrate how the preferred embodiments of the present invention are configured to maximize heat pumped per unit of input power during overall use, while minimizing the ratio of input current to maximum available current at a given steady-state temperature.

DETAILED DESCRIPTION OF THE BEST MODES AND PREFERRED EMBODIMENTS OF THE INVENTION

Steady-state, as used herein, is the state at which, during operation the heat pump assembly, the heat pump assembly reaches a selected temperature. For example, the heat pump assembly reaches a set temperature and the system is substantially balanced and is simply maintaining the set temperature.

Ambient Temperature is the temperature of the air or environment surrounding a thermoelectric cooling system; sometimes called room temperature.

COP (Coefficient of Performance) is the ratio of the heat removed or added, in the case of heating, divided by the input power.

DTmax is the maximum obtainable temperature difference between the cold and hot side of the thermoelectric elements within the module when Imax is applied and there is no heat load applied to the module.

Heat pumping is the amount of heat (Q) that a thermoelectric device is capable of removing, or "pumping", at a given set of operating parameters. For example, at a steady-state, when change in temperature ($\Delta T$) of the heat pump assembly at the top end compared to the bottom end of the heat pump assembly is 20° C. and heat (Q) is 0.5 Watts, or alternatively when change in temperature ($\Delta T$) of the heat pump assembly at the top end compared to the bottom end of the heat pump assembly is 40° C. and heat (Q) is 1.

Heat sink (also a cold sink when run in reverse) is a device that is attached to the hot side of thermoelectric module. It is used to facilitate the transfer of heat from the hot side of the module to the ambient.

Imax is the current that produces DTmax when the hot-side of the elements within the thermoelectric module are held at 300 K.

Peltier Effect is the phenomenon whereby the passage of an electrical current through a junction consisting of two dissimilar metals results in a cooling effect. When the direction of current flow is reversed heating will occur.

Qmax is the amount of heat that a TE cooler can remove when there is a zero degree temperature difference across the elements within a module and the hot-side temperature of the elements are at 300 K.

Thermal conductivity relates the amount of heat (Q) an object will transmit through its volume when a temperature difference is imposed across that volume.

Vmax is the voltage that is produced at DTmax when Imax is applied and the hot-side temperature of the elements within the thermoelectric module are at 300 K.

Figure 1:
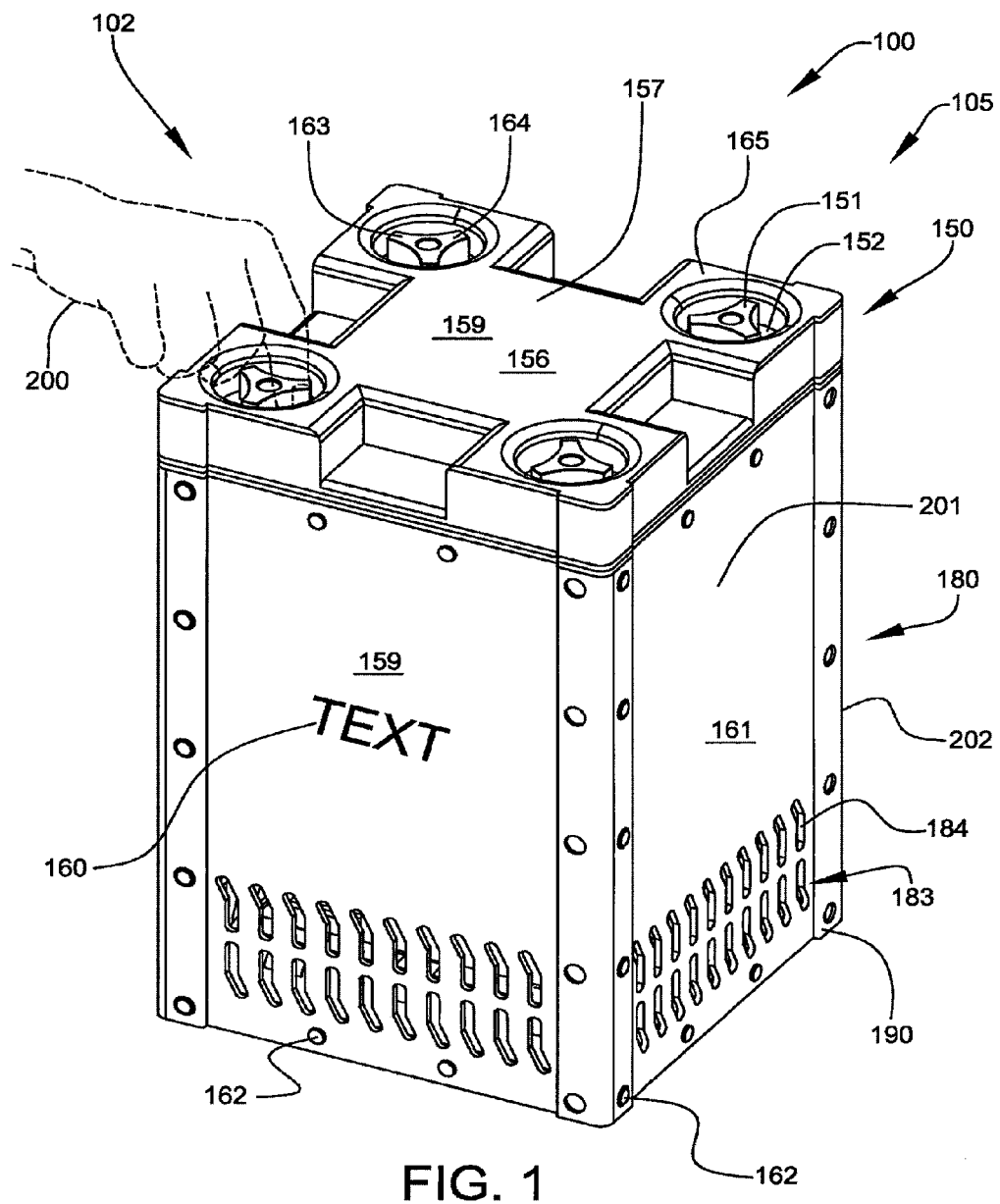
FIG. 1 shows a perspective view, illustrating an iso-thermal transport and storage system, according to a preferred embodiment of the present invention.

FIG. 1 shows a perspective view, illustrating at least one embodiment 102 of iso-thermal transport and storage system 100, according to a preferred embodiment of the present invention. Iso-thermal transport and storage system 100 is preferably designed to protect sensitive and perishable sensitive goods 139 (see FIG. 4, FIG. 5 and FIG. 6), preferably mammal biological matter, preferably mammal reproductive cells and/or tissues, preferably horse semen (at least embodying herein a thermal protection system, relating to thermally protecting temperature-sensitive goods). Upon reading the teachings of this specification, those with ordinary skill in the art will now appreciate that, under appropriate circumstances, considering issues such as changes in technology, user requirements, etc., other sensitive and perishable sensitive goods, such as cell and tissue cultures, nucleic acids, semen, stem-cells, ovaries, equine reproductive matter, bodily fluids, tissues, organs, and/or embryos plant tissues, blood, platelets, fruits, vegetables, seeds, live insects and other live samples, barely-frozen foods, pharmaceuticals, vaccines, chemicals, sensitive goods yet to be developed, etc., may suffice.

Outer enclosure 105 preferably comprises a rectangular-box construction, as shown. Outer enclosure 105 preferably includes lid portion 150, enclosure portion 180, and base portion 190, as shown. External dimensions of outer enclosure 105 preferably are about 14 inches in length with a cross-section of about 9-inches square, as shown.

Lid portion 150 preferably attaches to enclosure portion 180, preferably with at least one thumbscrew 151 and preferably at least one fibrous washer 152, as shown and explained herein. When lid portion 150 attaches to enclosure portion 180, such attachment preferably provides an airtight seal, as shown, preferably preventing contamination of enclosure portion 180 from external contaminants. Leakages of external contaminants, including microorganisms, into enclosure portion 180 are preferably prevented by applying pressure between at least one raised inner-portion 158, of lid portion 150, and threaded cap 142, as shown (also see FIG. 2 and FIG. 3) (at least herein embodying wherein said at least one vessel comprises at least one re-sealable surface structured and arranged to ingress and egress the temperature sensitive goods to and from said at least one thermal isolator) (at least herein embodying wherein said at least one re-sealable surface comprises at least one seal structured and arranged to exclude at least one microorganism from said at least one vessel). Upper-lid raised inner-portion 158 of lid portion 150 preferably is shaped, as shown, preferably by milling alternately preferably molding. Upper-lid raised inner-portion 158 preferably seals to the top of threaded cap 142 (see FIG. 2 and FIG. 3).

Fibrous washer 152 preferably comprises an outside diameter of about ½ inch, an inner diameter of about ¼ inch, and a thickness of about 0.08 inch. Over-tightening of thumb-screw 151 may cause cracking or distortion of lid portion 150 or degradation of fibrous washer 152. Fibrous washer 152 preferably protects at least one lid portion 150 from at least one user 200 damaging lid portion 150, due to over-tightening of thumbscrew 151. Fibrous washer 152 preferably withstands high compression loads, preferably up to 2000 pounds per square inch (psi) and preferably prevents vibration between mating surfaces of lid portion 150 and enclosure portion 180. Also, each fibrous washer 152 preferably provides sufficient friction to prevent loosening of each respective thumbscrew 151, as shown. Further, fibrous washer 152 preferably comprises a flat, deformable, inexpensive-to-produce, readily available, vulcanized, fibrous material, preferably adhering to ANSI/ASME B18.22.1 (1965 R1998). Upon reading the teachings of this specification, those with ordinary skill in the art will now appreciate that, under appropriate circumstances, considering issues such as changes in technology, user requirements, etc., other washer materials, such as gasket paper, rubber, silicone, metal, cork, felt, Neoprene, fiberglass, a plastic polymer (such as polychlorotrifluoroethylene), etc., may suffice.

Thumbscrew 151 preferably features at least one plastic grip 163, preferably with at least one tang 164, as shown. User 200 preferably grasps plastic grip 163 to tighten or loosen thumbscrew 151, preferably using at least three fingers. User 200 preferably uses tang 164 to apply rotary pressure to plastic grip 163 for tightening or loosening of thumbscrew 151, as shown. Upon reading this specification, those skilled in the art will now appreciate that, under appropriate circumstances, considering such issues as future technology, cost, application requirements, etc., other grips, such as, for example, interlocking heads, wings, friction, etc., may suffice.

Thumbscrew 151 preferably comprises at least one 300-series stainless-steel stud with preferably about ¼-20 inch threads, preferably mounted in phenolic thermosetting resin (preferably reinforced laminate produced from a medium weave cotton cloth impregnated with a phenolic resin binder, preferably MIL-i-24768/14 FBG). Plastic grip 163 preferably has about a 1½ inch wide top, preferably is about ⅝ inch thick, and preferably has about a ¼-inch offset between top portion of screw thread 148 and plastic grip 163. Screw thread 148 preferably is about ¾ inch long. Thumbscrew 151 preferably comprises part number 57715K55 marketed by McMaster-Carr. Upon reading the teachings of this specification, those with ordinary skill in the art will now appreciate that, under appropriate circumstances, considering issues such as changes in technology, user requirements, etc., other thermosetting composites, such as polyester, epoxy, vinyl ester matrices with reinforcement fibers of glass, carbon, aramid, etc., may suffice.

Stainless steel possesses wear resistance properties appropriate to withstand rough treatment during commercial transport and storage. Stainless steel also provides corrosion proofing to ensure longevity of thumbscrew 151 for applications when embodiment 102 of iso-thermal transport and storage system 100 experiences moisture or corrosive environments. Upon reading this specification, those skilled in the art will now appreciate that, under appropriate circumstances, considering such issues as future technology, cost, application requirements, etc., other screw materials, such as, for example, plastics, other metals, cermets, etc., may suffice.

Upon reading the teachings of this specification, those with ordinary skill in the art will now appreciate that, under appropriate circumstances, considering issues such as changes in technology, user requirements, etc., other fastening means, such as adhesives, fusion processes, other mechanical fastening devices including screws, nails, bolt, buckle, button, catch, clasp, fastening, latch, lock, rivet, screw, snap, and other fastening means yet to be developed, etc., may suffice.

At least one raised section 165 of lid portion 150 preferably substantially surrounds thumbscrew 151, as a protective guard, to protect thumbscrew 151 from damage or accidental adjustment, as shown. Raised section 165 preferably is about 1¼ inch tall, about 3¼ inches wide, and about 3¼ inches long, and preferably is located at each of the four corners of lid portion 150, as shown. Upon reading the teachings of this specification, those with ordinary skill in the art will now appreciate that, under appropriate circumstances, considering issues such as changes in technology, user requirements, etc., other protective guards, such as, for example, protective rims, gratings, handles, blocks, buffers, bulwarks, pads, protections, ramparts, screens, shields, wards and other such protective guards yet to be developed, etc., may suffice.

Figure 3:
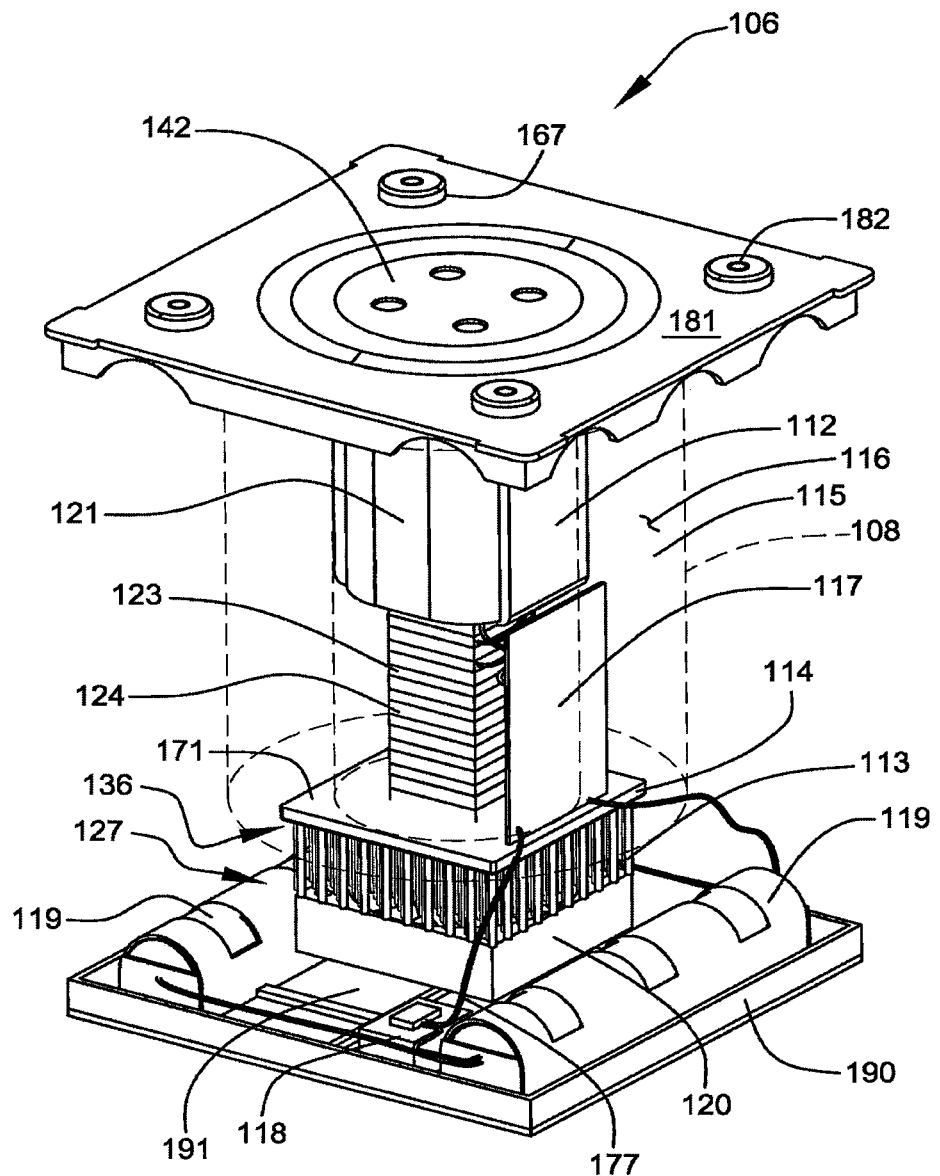
FIG. 3 shows a partially disassembled perspective view, illustrating arrangement of interior components of the embodiment of iso-thermal transport and storage system, according to the preferred embodiment of the present invention in FIG. 1.
Figure 4:
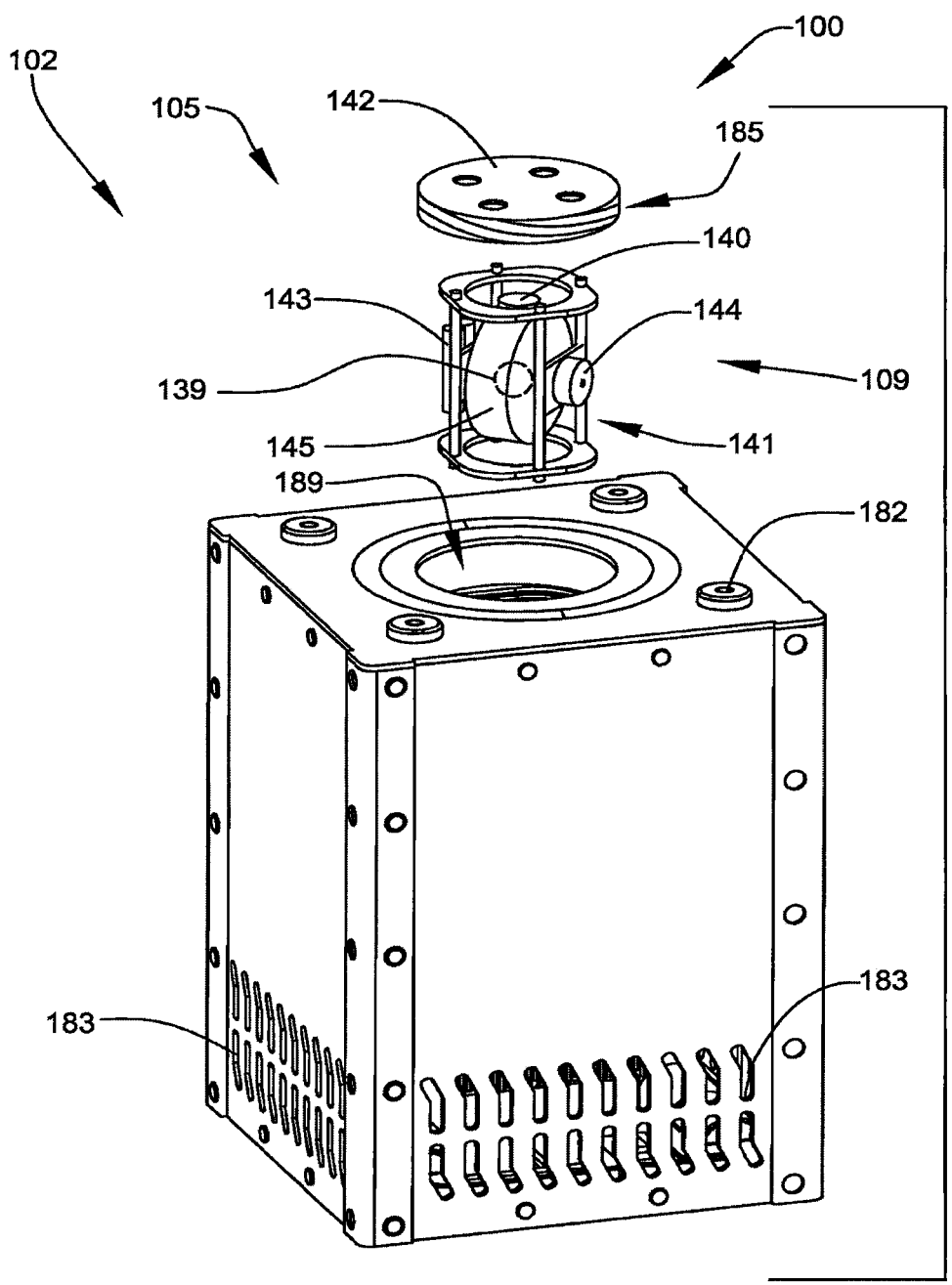
FIG. 4 shows an exploded perspective view, illustrating a mating assembly relationship between a sample rotating assembly and the outer enclosure of the iso-thermal transport and storage system, according to the preferred embodiment of the present invention in FIG. 1.

Enclosure portion 180 preferably contains a means to accept at least one screw thread 148 on thumbscrew 151, preferably threaded insert 182, as shown in FIG. 3 and FIG. 4. Internal thread size of threaded insert 182 is preferably about ¼-20 with a barrel diameter of about ⅓ inch, and a flange thickness of about 1/12 inch. Length of threaded insert 182 preferably is about 9/16 inch. Threaded insert 182 preferably is molded into, or, alternately preferably, swaged into, enclosure portion 180, as shown in FIG. 3 and FIG. 4. Threaded insert 182 is preferably made of die-cast zinc to provide rust and weather resistance. Threaded insert 182, as used in embodiment 102, preferably comprises part number 91316A200 sold by McMaster-Carr. Upon reading the teachings of this specification, those with ordinary skill in the art will now appreciate that, under appropriate circumstances, considering issues such as changes in technology, user requirements, etc., other threaded inserts, such as self-tapping, ultrasonic inserts for use on plastic, metal, or wood-base materials yet to be developed, etc., may suffice.

Inner-layer 155, located within lid portion 150, preferably is formed from urethane, as shown. Inner-layer 155 preferably is about 1¼ inches thick. Inner-layer 155 preferably is formed from expanded-urethane semi-rigid foam having a density of about of 2 pounds per cubic foot (lb/cu. ft.). Inner-layer 155 preferably utilizes part number SWD-890 as produced by SWD Urethane Company. Urethane is a thermoplastic elastomer that combines positive properties of plastic and rubber. Urethane-foam cells preferably are created by bubbling action of gases that create small air-filled pockets (preferably no more than 1/10 inch in diameter) that are preferable for creating both resistance to thermal transfer and structural integrity. Further, the urethane foam preferably acts as an impact absorber to protect components of iso-thermal transport and storage system 100 and sensitive and perishable sensitive goods 139 from mechanical shock and vibration during storage and transport, as shown. Upon reading the teachings of this specification, those with ordinary skill in the art will now appreciate that, under appropriate circumstances, considering issues such as changes in technology, user requirements, etc., other forming means, such as other urethane foaming techniques/materials, plastic or other material, for example, polyvinyl chloride, polyethylene, polymethyl methacrylate, and other acrylics, silicones, polyurethanes, or materials such as composites, metals or alloys yet to be developed, etc., may suffice.

Inner-layer 155 of lid portion 150 preferably is encapsulated in outer-surfacing layer 156 that preferably comprises a tough semi-rigid-urethane plastic, as shown. Outer-surfacing layer 156 preferably provides durability and protection for embodiment 102 of iso-thermal transport and storage system 100 during rough handling and incidents of mechanical shock and vibration. Outer-surfacing layer 156 preferably is tough but preferably amply flexible to withstand direct impact loads associated with normal commercial storage and transportation, as defined by ASTM D3951-98 (2004) Standard Practice for Commercial Packaging. Outer-surfacing layer 156 preferably is about ⅛ inch thick, as shown, and is preferably about 7 lb/cu. ft. density. Outer-surfacing layer 156 preferably utilizes part number SWD-890 as produced by SWD Urethane Company.

Vacuum insulated panels (VIPs) preferably are incorporated within lid portion 150 as VIP vacuum-panel 157 and in VIP insulation 108, as shown (also see FIG. 7) (at least embodying herein at least one thermal isolator for thermally isolating the temperature sensitive goods) (at least herein embodying wherein said at least one thermal isolator comprises at least one vacuum insulator for vacuum-insulating the temperature sensitive goods). VIPs preferably use the thermal insulating effects of a vacuum to produce highly efficient thermal insulation thermal insulation values (R-values) as compared to conventional thermal insulation, as shown. VIP vacuum-panel 157 and VIP insulation 108 preferably comprise NanoPore HP-150 core as made by NanoPore, Incorporated. NanoPore HP-150 core, which comprises a preferred thermal insulation for embodiment 102 of iso-thermal transport and storage system 100, has an R-value of about R-30 per inch and operates over a temperature range from about −200 degrees centigrade (° C.) to about 125° C. VIP vacuum-panel 157 and VIP insulation 108 preferably comprise layers of reflective film, having less than about 0.1, in the infrared spectrum from about one micron to about one millimeter wavelength, separating evacuated volumes, having pressure levels of less then 10 Torr. (at least herein embodying wherein said at least one vacuum insulator comprises at least one layer of reflective material; and at least herein embodying wherein infrared emittance of said reflective material is less than about 0.1, in the infrared spectrum from about one micron to about one millimeter wavelength; and at least herein embodying wherein absolute pressure of said least one evacuated volume is less than about 10 Torr).

VIP vacuum-panel 157, as used in the present invention, preferably is encased in urethane foam to protect VIP vacuum-panel 157 from mechanical damage during usage of embodiment 102 of iso-thermal transport and storage system 100, as shown. The thermal insulation of VIP vacuum-panel 157 becomes more effective when lid-horizontal decking-surface 153 (see FIG. 2) is in full contact with enclosure upper-horizontal decking-surface 181 (see FIG. 3), as shown.

Lid portion 150 also preferably provides at least one substantially flat-surface 159 that serves as a location for preferably displaying at least one indicia 160, as shown. User 200 preferably may place indicia 160 on at least one flat-surface 159, as shown. Indicia 160 preferably may aid in designating ownership, advertising, or warnings for embodiment 102 of iso-thermal transport and storage system 100 and/or the contents contained in embodiment 102 of iso-thermal transport and storage system 100, as shown.

At least one rivet 162 preferably is used when enclosure portion 180 is formed from at least one wall section 201 and at least one corner section 202, which require a fastening means to join the sections together, as shown. Wall section 201 preferably is about ⅛ inch thick, preferably made from aluminum alloy 6061, preferably T6 tempering, preferably anodized coated. Corner section 202 preferably is about ⅛ inch thick, preferably made from aluminum alloy 6061, preferably T6 tempering, preferably anodize coated. At least one rivet 162 preferably is used to hold at least one wall section 201 attach to at least one corner section 202. Rivet 162 preferably is selected to withstand tension loads parallel to the longitudinal axis of rivet 162 and sheer loads perpendicular to the longitudinal axis of rivet 162.

Rivet 162 preferably comprises a blind rivet, alternately preferably a solid rivet. Rivet 162 preferably is made from aluminum alloy 2024, as shown. Rivet 162 preferably has a head of about ⅓ inch diameter and preferably has a shaft of about ⁵⁄₃₂ inch diameter. Rivet 162 preferably comprises part number 97525A470 from McMaster-Carr. Hole size (in wall section 201 and corner section 202) for rivet 162 preferably may range from about 0.16 inch to about 0.17 inch in diameter. The shaft of rivet 162 preferably is about ½ inch diameter and preferably is upset to form a buck-tail head about ⅓ inch diameter after being inserted through holes, in wall section 201 and corner section 202, located near at least one corner of outer enclosure 105, as shown herein. Upon reading the teachings of this specification, those with ordinary skill in the art will now appreciate that, under appropriate circumstances, considering issues such as changes in technology, user requirements, etc., other securing means, such as bolts, buckles, buttons, catches, clasps, fastenings, latches, locks, rivets, screws, snaps, adapters, bonds, clamps, connections, connectors, couplings, joints, junctions, links, ties yet to be developed, etc., may suffice.

User 200 may impart rough treatment to embodiment 102; thus, the design preferably employs plastic material capable of absorbing impact forces. The nature of the construction of embodiment 102, in combination with expandable urethane 115 as insulation, assists isolation of thermo-electric assembly 123, as shown in FIG. 3, which is prone to damage from mechanical shock and/or vibration, from mechanical shock. Upon reading the teachings of this specification, those with ordinary skill in the art will now appreciate that, under appropriate circumstances, considering issues such as changes in technology, user requirements, etc., other impact absorption materials, for example, polyvinyl chloride, polyethylene, polymethyl methacrylate, and other acrylics, silicones, polyurethanes, composites, rubbers, soft metals or other such materials yet to be developed, etc., may suffice.

Enclosure portion 180 comprises at least one vent 183, preferably located on at least one vertical surface 161, preferably in close proximity to base portion 190, as shown. Vent 183 preferably allows ambient air to freely enter and circulate throughout at least one interior portion of outer enclosure 105, preferably using at least one fan 120, as shown (also see FIG. 7). Vent 183 preferably provides about a 25% free flow opening (of the lower portion of wall section 201), through which air preferably may be drawn in or exhausted, as shown. Vent 183 preferably comprises about 80 slots 184, each about ⅓ inch wide and about 1 inch high, as shown. Upon reading the teachings of this specification, those with ordinary skill in the art will now appreciate that, under appropriate circumstances, considering issues such as changes in technology, user requirements, etc., other opening means, such as holes, apertures, perforations, slits, or windows yet to be developed but which are capable of ambient air ingress and egress, etc., may suffice.

Base portion 190 preferably may use at least one rivet 162 preferably to connect to enclosure portion 180, thereby providing structural integrity for embodiment 102, as shown (also see FIG. 3). Upon reading the teachings of this specification, those with ordinary skill in the art will now understand that, under appropriate circumstances, considering issues such as changes in technology, user requirements, etc., other fastening devices, such as bolts, buckles, clasps, latches, locks, screws, snaps, clamps, connectors, couplings, ties or other fastening means yet to be developed, or fusion welding, adhesives, etc., may suffice.

Base portion 190 further preferably provides a mounting surface for at least one battery system 119 and preferably a means for enclosing enclosure portion 180 from the bottom, as shown (also see FIG. 3). Upon reading the teachings of this specification, those with ordinary skill in the art will now appreciate that, under appropriate circumstances, considering issues such as changes in technology, user requirements, etc., other enclosing means, such as lids, caps, covers, hoods, floors, bottoms or other such enclosing device yet to be developed, etc., may suffice.

Figure 2:
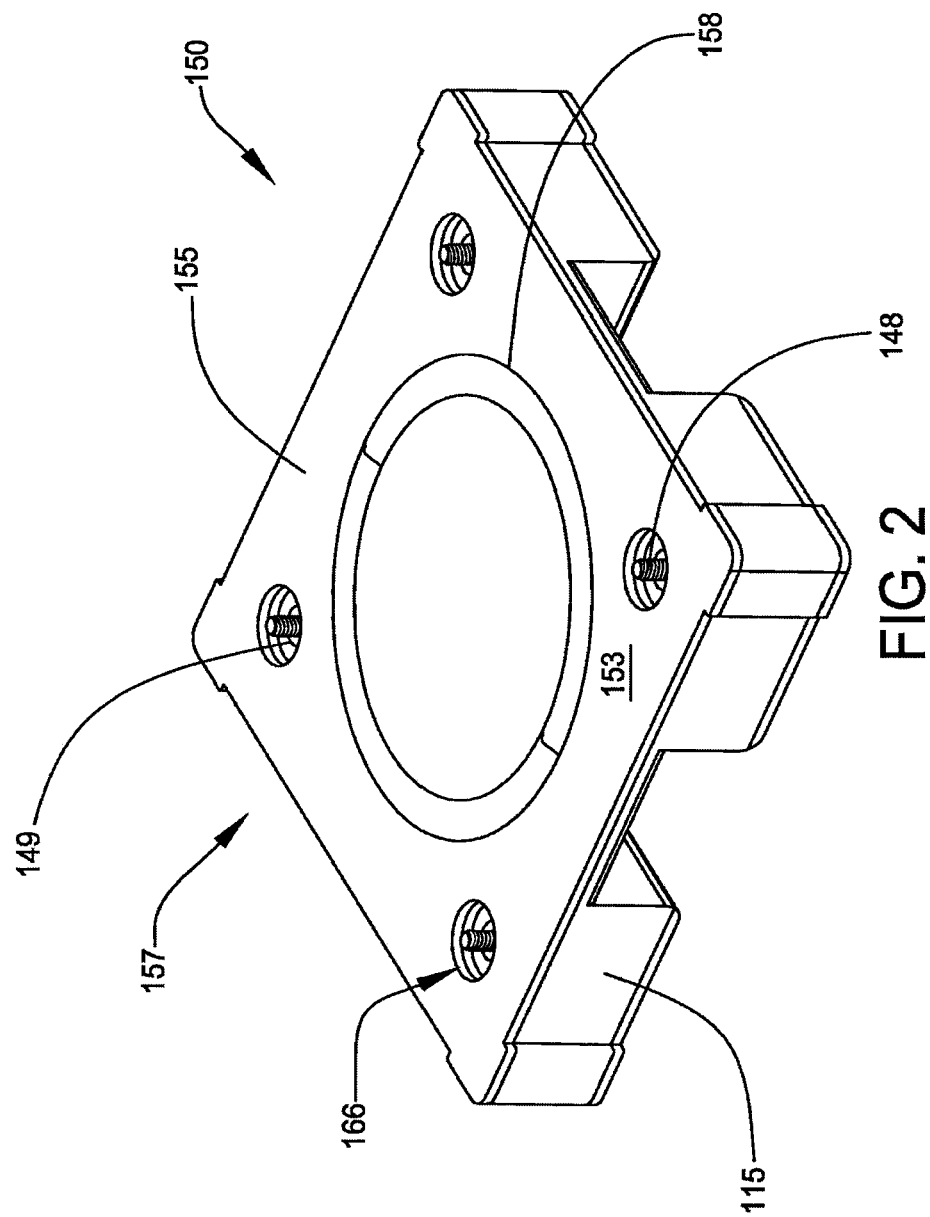
FIG. 2 shows a bottom-side perspective view, illustrating a lid portion of the embodiment of the iso-thermal transport and storage system, according to the preferred embodiment of the present invention in FIG. 1.

FIG. 2 shows a bottom-side perspective view, illustrating lid portion 150 of embodiment 102 of iso-thermal transport and storage system 100, according to the preferred embodiment of FIG. 1. Lid-horizontal decking-surface 153 preferably is molded, alternately preferably machined, to be a mating and sealing surface with enclosure upper-horizontal decking-surface 181, as shown (also see FIG. 3). Lid-horizontal decking-surface 153 and enclosure upper-horizontal decking-surface 181 preferably come into complete contact with each other, as shown in FIG. 1, preferably forming one of two barriers between the external environment and the contents of vessel 121, as shown (at least embodying herein wherein said at least one thermal isolator comprises at least one vessel structured and arranged to contain the temperature sensitive goods). Upon reading the teachings of this specification, those with ordinary skill in the art will now understand that, under appropriate circumstances, considering issues such as changes in technology, user requirements, etc., other enclosure means, such as lids, caps, covers, hoods, or floors, yet to be developed, etc., may suffice.

VIP vacuum-panel 157 preferably is embedded in lid portion 150 and preferably provides thermal insulation within embodiment 102, as shown. VIP vacuum-panel 157 preferably is about 4 inches wide, about 4 inches long and about 1 inch thick, as shown. Upon reading this specification, those skilled in the art will now appreciate that, under appropriate circumstances, considering such issues as future technologies, application requirements, etc., other VIP vacuum panel sizes, may suffice.

At least one retainer 149 preferably holds thumbscrew 151 and fibrous washer 152 from becoming detached from lid portion 150, as shown. Retainer 149 preferably slides smoothly down the threads when installed, such that thumbscrew 151 and fibrous washer 152 preferably are retained within at least one lid alignment well 166 in lid portion 150, as shown. Retainer 149 preferably is about 5/16 inch inner diameter, about 5/8 inch outer diameter, and is preferably made of black phosphate spring steel, as shown. Retainer 149 preferably comprises part number 94800A730 from McMaster-Carr. Upon reading the teachings of this specification, those with ordinary skill in the art will now appreciate that, under appropriate circumstances, considering issues such as changes in technology, user requirements, etc., other retaining means, such as clasps, clamps, holders, ties and other retaining means yet to be developed, etc., may suffice.

Lid alignment well 166 preferably aligns with at least one lid alignment post 167 (see FIG. 3). Lid alignment well 166 and lid alignment post 167 preferably allow quick alignment of lid portion 150 to enclosure portion 180.

FIG. 3 shows a partially disassembled perspective view, illustrating arrangement of inner-workings assembly 106 of embodiment 102 of iso-thermal transport and storage system 100, according to the preferred embodiment of the present invention in FIG. 1. FIG. 3 also shows threaded cap 142, which preferably is about 7½ inches in diameter and about ¾ inch thick. Threaded cap 142 preferably assists isolation of sensitive and perishable sensitive goods 139 from its surroundings, as shown. Upon reading the teachings of this specification, those with ordinary skill in the art will now appreciate that, under appropriate circumstances, considering issues such as changes in technology, user requirements, etc., other methods of isolation, such as caps, coverings, packings, gaskets, stoppers yet to be developed, etc., may suffice.

FIG. 3 also shows at least one battery system 119, preferably mounted on base portion 190. Battery system 119 preferably provides a portable, reliable power source for long durations while sensitive and perishable sensitive goods 139 are being transported in embodiment 102. At least one circuit board 117 preferably is wired to, and powered by, battery system 119 using at least one wire 177, as shown. Battery system 119 of the present invention preferably is about 3.6 volt DC supply. Battery system 119 preferably is rechargeable, preferably provides a source of power for thermo-electric assembly 123, and preferably is controlled by at least one safety on/off switch 118, as shown. Where an external power source is available, battery system 119 preferably may be recharged while embodiment 102 is in storage or transport.

Figure 5:
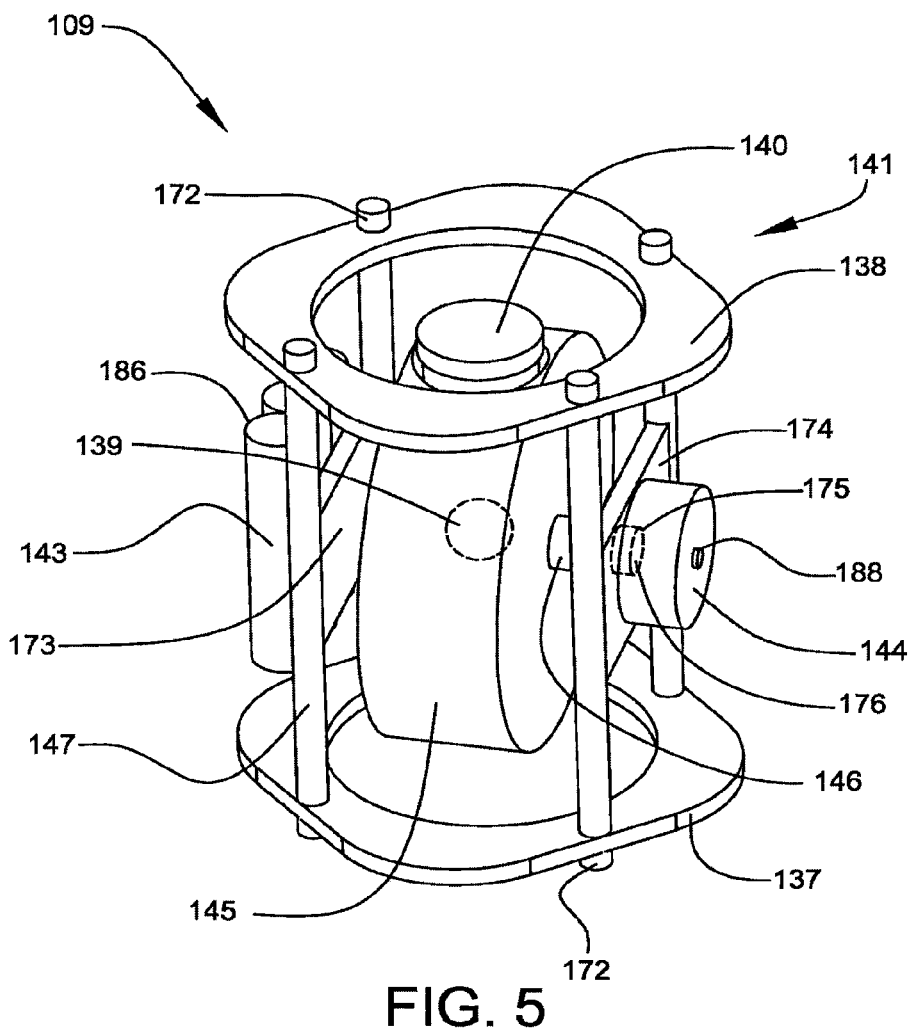
FIG. 5 shows a perspective view, illustrating the sample rotating assembly, according to the preferred embodiment of the present invention in FIG. 1.

In addition, at least one sample battery pack 143 preferably may be mounted on sample assembly frame 141, as shown in FIGS. 4 and 5. Upon reading the teachings of this specification, those with ordinary skill in the art will now appreciate that, under appropriate circumstances, considering issues such as changes in technology, user requirements, etc., other power sources, such as accumulators, dry batteries, secondary batteries, secondary cells, storage cells, storage devices, wet batteries or other such storage means yet to be developed, or a fixed power source, etc., may suffice.

Wire 177 as shown comprises about 16 AWG coated 26/30 gage copper stranded-conductors with an insulation thickness of about 1/64 inches and a diameter of about 1/12 inches, as shown. Operating temperature range of wire 177 preferably is from about −40° C. to about 105° C. Insulation covering conductors of wire 177 preferably is color-coded polyvinyl chloride (PVC). Voltage rating of wire 177 is about 300V. Wire 177 preferably is marketed by Alpha Wire Company part number 3057. Upon reading the teachings of this specification, those with ordinary skill in the art will now appreciate that, under appropriate circumstances, considering issues such as changes in technology, user requirements, etc., other wiring configurations for example parallel, other series/parallel connections, other size wire, etc., may suffice.

FIG. 3 also shows thermo-electric assembly 123, preferably comprising at least one thermo-electric semi-conductor node 133 (see FIG. 8) preferably capable of being wired in at least one series and/or parallel configuration to at least one battery system 119. Thermoelectric semi-conductor node 133 preferably provides an incremental temperature staging means (at least embodying herein at least one thermo-electric heat pump adapted to control-at least one temperature of the temperature-sensitive goods; wherein said at least one thermoelectric heat pump comprises at least one thermo-electric device adapted to active use of the Peltier effect). Thermoelectric assembly 123 preferably is about 7⅝ inches high, about 5 inches long and about 5 inches wide when stacked, as shown. Upon reading the teachings of this specification, those with ordinary skill in the art will now appreciate that, under appropriate circumstances, considering issues such as changes in technology, user requirements, etc., other heat-transferring effects, such as induction, thermal radiation means yet to be developed, etc., may suffice.

In embodiment 102, user 200 may select at least one set-point temperature for sensitive and perishable sensitive goods 139. Embodiment 102 preferably then automatically maintains the at least one set-point temperature for sensitive and perishable sensitive goods 139, preferably for a duration necessary to store or transport sensitive and perishable sensitive goods 139 to at least one predetermined destination. Embodiment 102 preferably uses thermo-electric assembly 123, preferably in conjunction with fan 120, preferably in at least one closed-loop feedback sensing of at least one thermocouple 124, as shown. Thermocouple 124 preferably comprises at least one temperature-sensing chip, such as produced by Dallas Semiconductor part number DS18B20. Thermocouple 124 preferably is used as a single-wire programmable digital-thermometer to measure temperatures at thermocouple 124, as shown. Upon reading the teachings of this specification, those with ordinary skill in the art will now appreciate that, under appropriate circumstances, considering issues such as changes in technology, user requirements, etc., other temperature tuning means, such as adjusters, dials, knobs, on/off power switches, switches, toggles, tuners, thermo-conductive means or other temperature tuning means yet to be developed, etc., may suffice.

Figure 6:
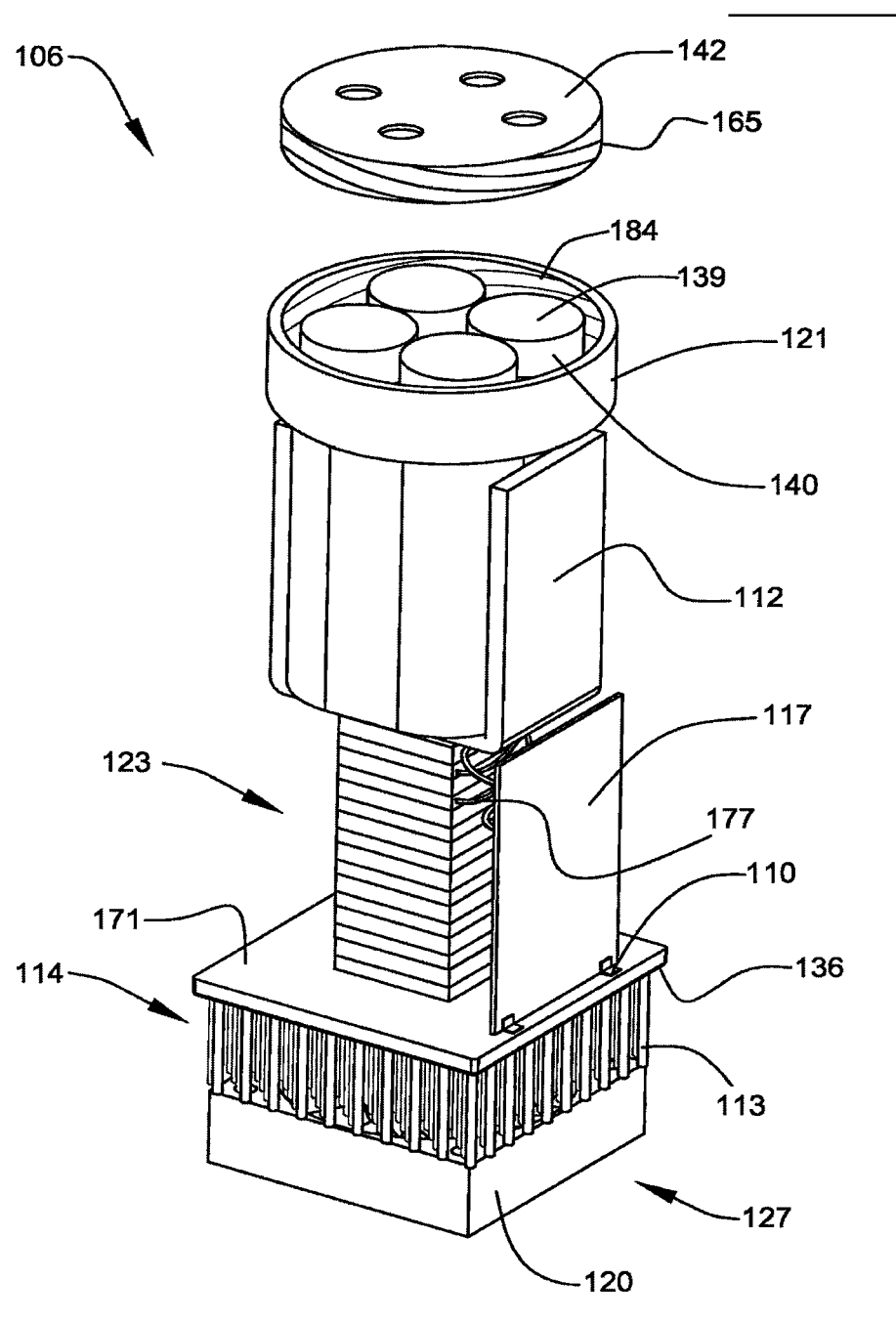
FIG. 6 shows a partially exploded perspective view, illustrating the order and arrangement of the inner working assembly and sample placements of the iso-thermal transport and storage system, according to the preferred embodiment of the present invention in FIG. 1.

Embodiment 102 preferably comprises at least one vessel 121 preferably designed to store and contain sensitive and perishable sensitive goods 139, as shown. Vessel 121 preferably is made from urethane or, alternately preferably, aluminum. Upper section of vessel 121 preferably comprises at least one inner threaded portion 189 that permits vessel lid 122, having an external threaded portion 185, to be threaded together (also see FIG. 4). Threading together of upper section of vessel 121 and vessel lid 122, as shown in FIG. 6, preferably provides a seal that isolates sensitive and perishable sensitive goods 139 from the local environment. Vessel lid 122 alternately preferably may have a friction fit sealing relationship with vessel 121, as shown. Tolerances for friction fit will depend on pressure required to be maintained within vessel 121. Upon reading the teachings of this specification, those with ordinary skill in the art will now appreciate that, under appropriate circumstances, considering issues such as changes in technology, user requirements, etc., other means of attaching, such as, clamped-lid mechanisms, bolted lids, joined by adhesives and other means yet to be developed, etc., may suffice.

Aluminum 6069-T4 may preferably be used, due to its light weight and ability to withstand high pressure, should sensitive and perishable sensitive goods 139 need to be maintained at a high pressure. Aluminum preferably is used because of its high thermal conductivity of about, at about 300° Kelvin (300° K), 237 watts-per meter-degree Kelvin (W·m$^{-1}$·K$^{-1}$), manufacturability, light weight, resistance to corrosion, and relative dimensional stability (low thermal expansion rate) over a substantial working temperature range. During the heat transfer processes, materials store energy in the intermolecular bonds between the atoms. [When the stored energy increases (rising temperatures of the material), so does the length of the molecular bond. This causes the material to expand in response to being heated, and causes contraction when cooled.] Embodiment 102 preferably overcomes this problem by using aluminum due to the relatively low thermal expansion rate of about 23.1 micro-meters per meter per degree Kelvin (μm·m$^{-1}$·K$^{-1}$) (300° K). This property preferably allows embodiment 102 to effectively manage thermally induced linear, area, and volumetric expansions throughout a wide range of ambient temperatures and desired set-point temperatures for sensitive and perishable sensitive goods 139. Upon reading the teachings of this specification, those with ordinary skill in the art will now appreciate that, under appropriate circumstances, considering issues such as changes in technology, user requirements, etc., other materials, such as, for example, copper, copper alloys, other aluminum alloys, low-thermal-expansion-composite constructions, etc., may suffice.

At least one volume 116 exists between VIP vacuum-panel 157 and vessel 121 mounted above thermo-electric assembly 123, as shown. Volume 116 preferably is filled with expandable urethane 115, as shown. Preferably, the expandable urethane 115 foam has a density of about 2 lb/cu. ft. Expandable urethane 115 preferably secures all components within the upper portion of embodiment 102, as shown. Expandable urethane 115 foam preferably is only allowed to fill the portion shown within the illustration so as to preferably allow ample available space for heat sink 114, at least one fan assembly 127, and at least one battery system 119 to operate in a non-restricted manner, as shown (also see FIG. 6).

Alternately preferably, volume 116 between VIP vacuum-panel 157 and vessel 121 preferably is filled up to three layers of about ½ inch thick VIPs. Such VIPs preferably are curved around vessel 121 and thermo-electric assembly 123, preferably creating a total minimum thickness of about 1½ inches, as shown. Square-box style VIPs may also be used depending on specific geometries associated with embodiment 102. After such VIPs are positioned around vessel 121 and thermo-electric assembly 123, preferably the remaining cavity areas are filled with expandable urethane 115. Upon reading the teachings of this specification, those with ordinary skill in the art will now understand that, under appropriate circumstances, considering issues such as changes in technology, user requirements, etc., other surface cooling means, such as appendages, projections, extensions, fluid heat-extraction means and others yet to be developed, etc., may suffice.

All of the mentioned items within inner-workings assembly 106 lose efficiency if not cooled. Fan 120 preferably circulates ambient air through vent 183, preferably impinging on at least one fin 113, as shown. Fin 113 preferably absorbs heat from the air (in heating mode) or preferably rejects heat to the air (cooling mode). Fin 113 further preferably transports heat from/to its surface into heat sink 114, preferably through conductive means. Fin 113 and heat sink 114 preferably are comprised of 3000 series aluminum. Aluminum alloys have the significant advantage that they are easily and cost-effectively formed by extrusion processes. Upon reading this specification, those skilled in the art will now appreciate that, under appropriate circumstances, considering such issues as future technologies, cost, available materials, etc., other fin and heat sink materials, such as, for example, other aluminum alloys, copper, copper alloys, ceramics, cermets, etc., may suffice. Heat sink 114 preferably is designed for passive, non-forced air-cooling, as shown.

Fan 120 preferably provides necessary thermal control by creating an active means of air movement onto heat sink 114 surfaces, as shown. Fan assembly 127 preferably is about 3⅞ inches long, about 3⅞-inches wide and about 1⅓ inches high. Fan 120 preferably comprises model number GM0504PEV1-8 part number GN produced by Sunon. Fan 120, is preferably rated at about 12 VDC, however, fan 120 preferably operates at 5 VDC. Airflow preferably is about 5.9 cubic feet per minute (CFM) at a speed of about 6000 revolutions per minute (rpm) with a power consumption of about ⅜ watts (W). Noise of fan 120 preferably is limited to about 26 decibels (dB). Fan 120 preferably weighs about 7.5 grams (g).

Fan 120 alternately preferably is operated at about 5 volts with a DC/DC boost converter, not shown. The DC/DC boost converter preferably is a step-up type, preferably with a start-up of less than 0.9 VDC with about 1 mill-ampere (mA) load. The DC/DC boost converter preferably comprises part number AP1603 as marketed by Diodes Incorporated. Upon reading the teachings of this specification, those with ordinary skill in the art will now understand that, under appropriate circumstances, considering issues such as changes in technology, user requirements, etc., other conversion means, such as, for example, buck converter or buck-boost converter yet to be developed, etc., may suffice.

Heat sink 114 preferably comprises at least one heat-sink plate 136, base surface 171 (at least embodying herein wherein said at least one vessel comprises at least one heat-transferring surface structured and arranged to conductively exchange heat to and from said at least one temperature controller), and fins 113. Heat sink 114 preferably is FH-type as produced by Alpha Novatech, Inc., as shown. A preferred configuration of heat sink 114 comprises about 200 individual, fins 113, preferably shaped hexagonally, preferably with dimensions of about ⅛ inch wide across the flats and about 1⅓ inches long, as shown. Fins 113 are preferably arranged in a staggered relationship on heat-sink plate 136, as shown. Heat-sink plate 136 preferably is about ¼ inch thick, about 3⅞ inches wide and about 3-⅞ inches long, as shown. Heat-sink plate 136 and fins 113 preferably comprise a one-piece extrusion. Base surface 171 of heat sink 114 preferably is flat and smooth to ensure adequate thermal contact with the object being cooled or heated, as shown. Upon reading the teachings of this specification, those with ordinary skill in the art will now understand that, under appropriate circumstances, considering issues such as changes in technology, user requirements, etc., other heat sink materials, such as copper, gold, silver, brass, tungsten, ceramics, cermets, or metal alloys of different sizes and configurations, etc., may suffice.

FIG. 4 shows an exploded perspective view, illustrating a mating assembly relationship between at least one sample rotating assembly 109 and outer enclosure 105 of the isothermal transport and storage system 100, according to the preferred embodiment of the present invention in FIG. 1.

Vessel 121 preferably may be designed to allow rotation capability, as shown. Further, vessel 121 alternately preferably may be designed to allow at least one formed separator support sample tube 140, set in vessel 121, and preferably spaced so as to eliminate contact with any other sample tube 140, as shown in FIG. 6. Sample tube 140 preferably may be made of glass, alternately preferably metal alloy, alternately preferably plastic, alternately preferably composite material.

Sample rotating assembly 109 preferably comprises a removable assembly that preferably allows rotation of at least one sample tube 140 while sample assembly frame 141 preferably remains stationary within the confines of outer enclosure 105, as shown. Sample rotating assembly 109 preferably is located within outer enclosure 105, as shown. Sample rotating assembly 109 preferably is held securely by means of threaded cap 142 that preferably restricts any upward motion of sample rotating assembly 109 within outer enclosure 105, as shown. Sample rotating assembly 109 preferably is about 1 1 inches in diameter and about 3⁷⁄₁₆ inches wide, as shown. User 200 may preferably open, close, and reopen lid portion 150 during storage, or during transport, preferably without compromising the integrity of sensitive and perishable sensitive goods 139.

Maintaining integrity of sensitive and perishable sensitive goods 139 comprises protection from, for example, contamination by foreign gases, liquids, moisture, or solids, preferably minimizing any fluctuations in temperature, preferably preventing any spillage or degradation by ultraviolet or other forms of radiation, as shown. If integrity is not maintained, sensitive and perishable sensitive goods 139 may die, degrade through separation, denature, deform, mold, dry out, become contaminated, or be unusable or inaccurate, i.e., if not kept within a protective isolated environment. Sensitive and perishable sensitive goods 139 preferably maintain integrity due to the further sealing within vessel 121, as shown. Upon reading the teachings of this specification, those with ordinary skill in the art will now appreciate that, under appropriate circumstances, considering issues such as changes in technology, user requirements, etc., other enclosing means for example caps, covers, hoods, roofs, top and others yet to be developed, or other rotational means, etc., may suffice.

As shown in FIG. 4, sample assembly frame 141 provides a structural mount for mounting at least one sample battery pack 143, as shown. Also, sample assembly frame 141 preferably provides a suspending mount, preferably flat-bar 173, to suspend at least one rotating cylinder 145, as shown. Additionally, sample assembly frame 141 preferably provides a handle for user 200 to grasp sample rotating assembly 109 preferably for lifting-from or lowering-into outer enclosure 105, as shown.

User 200 preferably may remove sample rotating assembly 109 for accuracy of filling or dispensing from sensitive and perishable sensitive goods 139 into at least one sample tube 140, as also shown in FIG. 5. This feature preferably also permits ease of cleaning and sanitizing of embodiment 102 by user 200 at re-use intervals of embodiment 102, as shown (at least embodying herein wherein such step of providing re-use comprises at least one cleaning step). Sample rotating assembly 109 preferably requires less space when removed from outer enclosure 105, as shown, for instances when space is limited such as in laboratory settings. Upon reading the teachings of this specification, those with ordinary skill in the art will now appreciate that, under appropriate circumstances, considering issues such as changes in technology, user requirements, etc., other portable containing means, such as bags, canisters, chambers, flasks, humidors, receptacles, or vessels yet to be developed, etc., may suffice.

FIG. 5 shows a perspective view, illustrating sample-rotating assembly 109, according to the preferred embodiment of the present invention in FIG. 1. Sample battery pack 143 preferably comprises at least one battery 186, preferably three AAA-sized batteries (each preferably having about ⁷⁄₁₆-inch outer diameter and being about 1¾ inches long) as shown. These batteries preferably may be tabbed for ease of interconnection and removal, as shown. These batteries preferably are series connected to supply about 3.6 volts direct current (VDC) to supply power to sample rotating assembly 109, as shown. Upon reading the teachings of this specification, those with ordinary skill in the art will now appreciate that, under appropriate circumstances, considering issues such as changes in technology, user requirements, etc., other batteries, such as, for example, AA-sized batteries, unified battery packs, etc., may suffice.

Batteries 186 preferably comprise alkaline batteries, alternately preferably, high capacity nickel metal hydride (NiMH) batteries, alternately preferably lithium ion batteries, alternately preferably lithium polymer batteries. Upon reading the teachings of this specification, those with ordinary skill in the art will now appreciate that, under appropriate circumstances, considering issues such as changes in technology, user requirements, etc., other battery materials, such as, for example, other metal hydrides, electrolytic gels, bio-electric cells, etc., may suffice.

Sample battery pack 143 preferably provides power for at least one gear motor 144 preferably to turn at least one shaft 146, as shown (at least herein embodying wherein said at least one goods rotator is structured and arranged to self-power from at least one energy storage device) (at least herein embodying wherein said least one energy storage device comprises at least one battery). Shaft 146 preferably is connected to one end of rotating cylinder 145 and preferably connected to at least one gear motor 144 on the opposing end of rotating cylinder 145, as shown. When at least one gear motor 144 is activated, shaft 146 preferably rotates rotating cylinder 145 preferably turning about the longitudinal axis of shaft 146, as shown. The rotating motion preferably may be enabled to one direction, or, alternately preferably, in two directions for agitating, depending on application requirements to preserve sensitive and perishable sensitive goods 139. Shaft 146 preferably has an outer diameter of about ½ inch and is about 3¼ inches long, as shown. Gear motor 144 preferably has about 1-inch outer diameter and about ½ inch length, as shown (at least herein embodying wherein said at least one thermal isolator comprises at least one goods rotator structured and arranged to rotate the temperature sensitive goods within said at least one thermal isolator). Upon reading the teachings of this specification, those with ordinary skill in the art will now appreciate that, under appropriate circumstances, considering issues such as changes in technology, user requirements, etc., other rotating means, such as worm and pinion combinations, gearing combinations, sprockets and chains, pulleys and belts or chains and swing mechanical mechanisms yet to be developed, etc., may suffice.

Sample tube 140 preferably is held securely when rotating cylinder 145 to preferably allow sensitive and perishable sensitive goods 139 to remain in a fixed position or alternately preferably to rotate upon activation of at least one gear motor 144, as shown. Sample tube 140 (in the illustrated embodiment) preferably has an outer diameter of about 3⅞ inches and is about 8 inches long, as shown. Sterile centrifuge tubes as produced by Exodus Breeders Corporation code number 393 preferably may be used, as shown. Sample tube 140, preferably comprising a size of about 50 milliliter (ml), is non-free standing and has a conical end.

Sample assembly frame 141 preferably is in a closely fitted relationship within outer enclosure 105 to minimize vibrations, as shown. Sample tube 140 preferably may be in a closely fitted relationship with rotating cylinder 145 preferably minimizing vibration and the possibility of physically damaging sample tube 140, as shown. This arrangement preferably minimizes potential compromising of the integrity of sensitive and perishable sensitive goods 139, as well as preferably lessens possible dangers of exposure to user 200. Sample assembly frame 141 preferably is about 5 inches high and preferably is made of urethane preferably smooth-cast-roto-molded, as shown. Sample assembly frame 141 preferably consists of at least one upright bar 147, preferably with an outer diameter of about ½ inch and a length of about 5 inches, as shown. Upright bar 147, preferably comprising urethane preferably is friction fitted through upper frame-plate 138 and preferably lower frame-plate 137, as shown. Upright bar 147 preferably protrudes about ½ inch outwardly from upper side of upper frame-plate 138 and lower side of lower frame-plate 137, as shown. One upright bar 147 preferably is affixed with at least one connection flat-bar 173 to another upright bar 147, preferably to provide structural rigidity for sample assembly frame 141, as shown. At least one connection flat-bar 174 preferably connects two other upright bars 147. Connection flat-bar 174 preferably comprises at least one shaft pass-through 175 allowing shaft 146 to pass through with at least one bearing 176 to aid rotation, as shown.

Gear motor 144 preferably is fit on end of shaft 146 and preferably held in place with a hub 188, as shown. Connection flat-bar 173 preferably provides a mounting for sample battery pack 143, as shown. Connection flat-bar 173 preferably is attached to upright bar 147, preferably by adhesive, alternately preferably fusion welding, as shown. Connection flat-bar 173 preferably prevents twisting of sample assembly frame 141, as shown. Upon reading the teachings of this specification, those with ordinary skill in the art will now appreciate that, under appropriate circumstances, considering issues such as changes in technology, user requirements, materials, etc., other attachment methods, such as, for example, screws, epoxies, soldering, etc., may suffice.

FIG. 6 shows a partially exploded perspective view, illustrating the order and arrangement of inner-workings assembly 106 of iso-thermal transport and storage system 100, according to the preferred embodiment of FIG. 1. Embodiment 102 preferably may be used without sample rotating assembly 109, as shown, and thereby is suitable for handling sensitive and perishable sensitive goods 139 that do not need to be rotated or agitated to preserve the required quality. Fan 120 preferably blows ambient air pulled in through vent 183, as shown in FIG. 1 and FIG. 4. Heat sink 114 preferably comprises fin 113 preferably mounted or otherwise configured to be perpendicular to fan 120, as shown. Heat sink 114 preferably is configured for providing maximum surface area exposure to air currents from fan 120, preferably to maximize the rates of cooling or heating within embodiment 102, as shown. Preferably, this method of forced-convection heat-transfer creates fewer fluctuations in temperature of sensitive and perishable sensitive goods 139 over any extended time. Upon reading the teachings of this specification, those with ordinary skill in the art will now appreciate that, under appropriate circumstances, considering issues such as changes in technology, user requirements, etc., other heat sink cooling devices, such as aerators, air-conditioners, and ventilators yet to be developed, etc., may suffice.

At least one retainer 112 preferably is attached at its base to thermo-electric assembly 123, and preferably partially wraps around vessel 121 preferably permitting user 200 to lift vessel 121 out of embodiment 102. Retainer 112 preferably is a means to ensure vessel 121 is held in place, as shown. Retainer 112 preferably is formed in a U-shape, as shown, and preferably is constructed of smooth-cast-roto-molded urethane as made by Smooth-On manufacturers. Smooth-Cast ROTO™ urethane is a semi-rigid plastic and preferably is selected for its density-control, structural and insulating characteristics. Smooth-Cast ROTO™ has a shore D hardness of about 65, a tensile strength of about 3400 psi, tensile modulus of about 90,000 psi, with a minimal shrinkage of about 0.01 in/in over a seven-day period. Upon reading the teachings of this specification, those with ordinary skill in the art will now appreciate that, under appropriate circumstances, considering issues such as changes in technology, user requirements, etc., other retaining means, such as catches, clasps, clenches, grips, holds, locks, presses, snaps, vices, magnets, or mechanical attaching means yet to be developed, etc., may suffice.

Retainer 112 according to the present invention may alternately preferably be manufactured from aluminum, due to its high thermal conductivity and low mass density. The high thermal conductivity of retainer 112 preferably efficiently transports heat between thermo-electric assembly 123 and vessel 121, preferably with a minimum of temperature difference between thermo-electric assembly 123 and vessel 121. This efficient heat conduction preferably supports temperature stability for sensitive and perishable sensitive goods 139, contained within vessel 121, as shown. Upon reading the teachings of this specification, those with ordinary skill in the art will now appreciate that, under appropriate circumstances, considering issues such as changes in technology, user requirements, etc., other high thermal conductors, such as copper, brass, silver, gold, tungsten and other conductive element alloys yet to be developed, etc., may suffice.

Thermo-electric assembly 123 preferably is mounted on base surface 171 of heat sink 114 and preferably connected to retainer 112, as shown. Upon reading the teachings of this specification, those with ordinary skill in the art will now appreciate that, under appropriate circumstances, considering issues such as changes in technology, user requirements, etc., other retaining means, such as catches, clasps, clenches, grips, holds, locks, nippers, presses, snaps, vices, magnets, or mechanical attaching means yet to be developed, etc., may suffice.

Circuit board 117 preferably is mounted substantially parallel to thermo-electric assembly 123 preferably by at least one bracket 110, as shown. Also, circuit board 117 preferably mounts to flat upper surface of heat sink 114, as shown. Upon reading the teachings of this specification, those with ordinary skill in the art will now appreciate that, under appropriate circumstances, considering issues such as changes in technology, user requirements, cost, etc., other circuit board mountings, such as suspension in foam insulation, epoxies, snap-in, cable suspensions, etc., may suffice.

Figure 8:
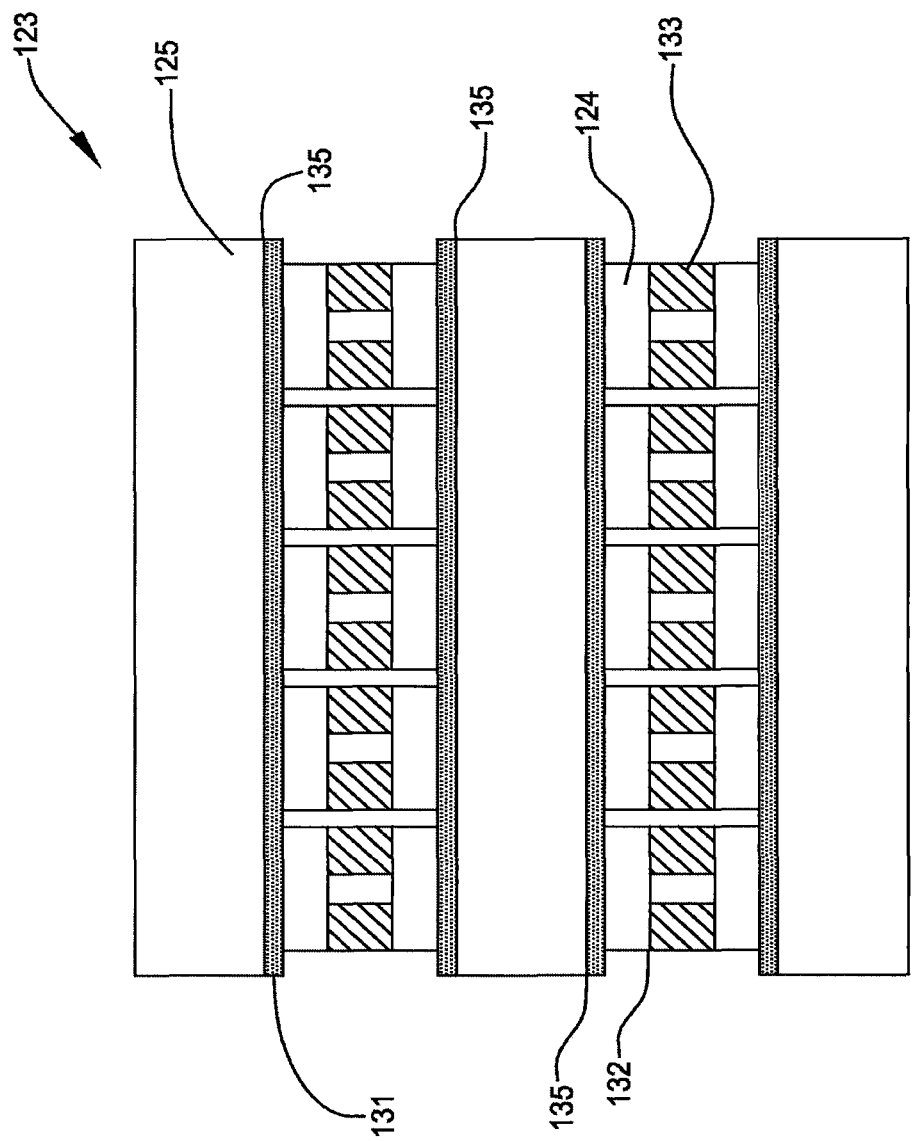
FIG. 8 shows a side profile view, illustrating a thermoelectric assembly of the iso-thermal transport and storage system, according to the preferred embodiment of the present invention in FIG. 1.

Circuit board 117 preferably controls and regulates the functioning of thermo-electric assembly 123, preferably according to electronic feedback from thermocouple 124 within thermo-electric assembly 123, as also shown in FIG. 8. At least one mounting hole preferably is present in circuit board 117 and preferably to allow mounting by bracket 110, as shown. Upon reading the teachings of this specification, those with ordinary skill in the art will now appreciate that, under appropriate circumstances, considering issues such as changes in technology, user requirements, etc., other mounting means for example hooks, magnets, mechanical fastening means yet to be developed, fusion means, etc., may suffice.

Figure 7:
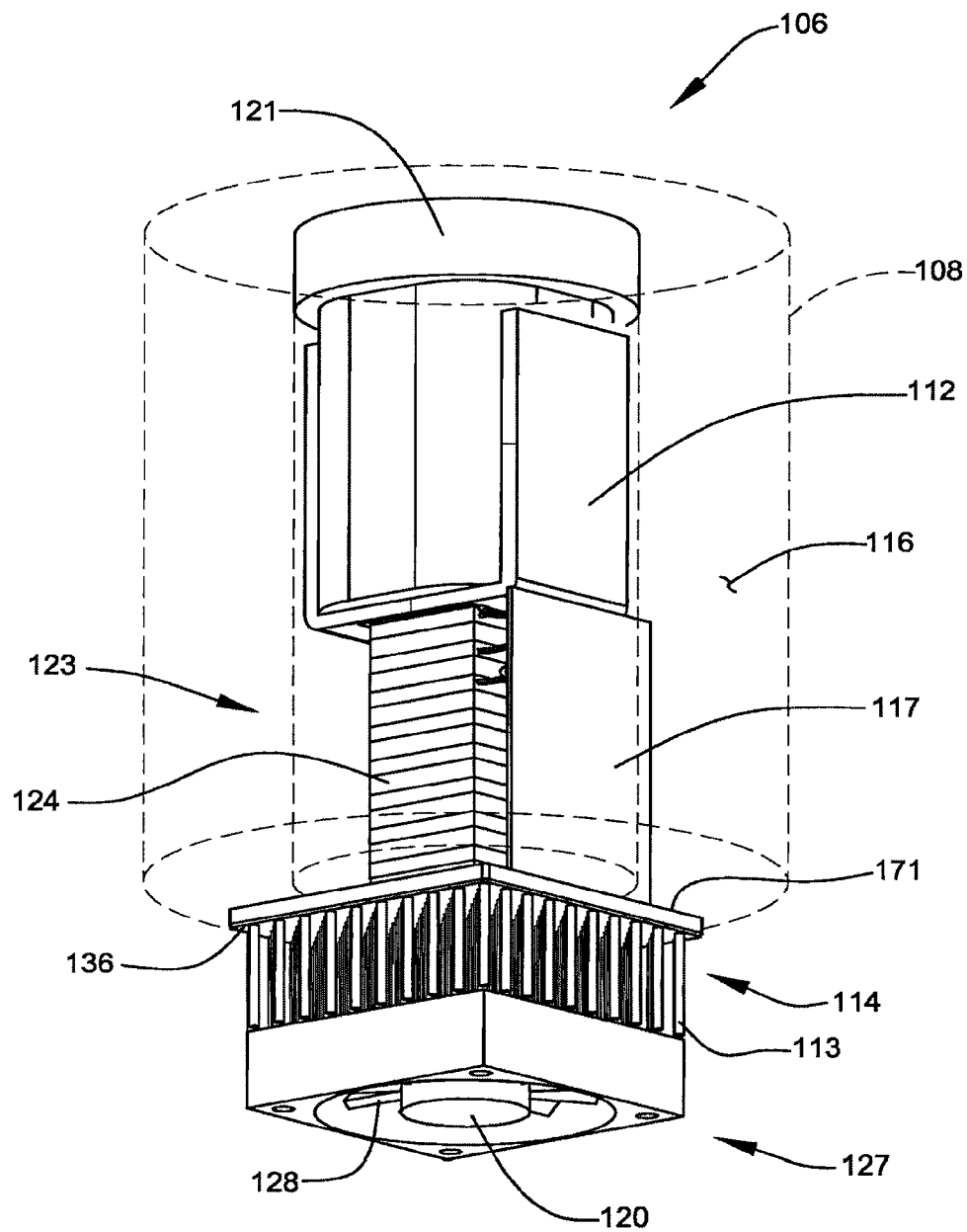
FIG. 7 shows a partially disassembled bottom perspective view, illustrating the inner working assembly of the iso-thermal transport and storage system, according to the preferred embodiment of the present invention in FIG. 1.

FIG. 7 shows a partially disassembled bottom perspective view, illustrating inner-workings assembly 106 of iso-thermal transport and storage system 100, according to the preferred embodiment of FIG. 1. Excess heat preferably is pumped into heat sink 114 from thermo-electric assembly 123 and preferably convectively transferred into ambient air by forced convection from fin 113, by at least one fan 120, as shown.

During time periods when heat must be sourced from the ambient to warm sensitive and perishable sensitive goods 139, such that the temperature of sensitive and perishable sensitive goods 139 is preferably maintained near a desired set-point temperature, fin 113, as shown, preferably may serve to collect heat from the ambient air. Under this alternate operational mode, at least one fan 120 preferably pushes relatively warm ambient air over fin 113, thereby allowing heat to be absorbed into fin 113. Such absorbed heat preferably conducts up into thermo-electric assembly 123, where the heat is preferably pumped, as needed, into vessel 121 and thus provides necessary heating to maintain the set-point temperature of sensitive and perishable sensitive goods 139.

Control circuit on circuit board 117 enables user 200 to re-set set-point temperature, of sensitive and perishable sensitive goods 139, to the desired temperature at which sensitive and perishable sensitive goods 139 are maintained (this arrangement at least herein embodying wherein such step of providing re-use comprises at least one set-point re-setting step). Upon reading the teachings of this specification, those with ordinary skill in the art will now appreciate that, under appropriate circumstances, considering issues such as changes in technology, user requirements, etc., other heat-sink heat exchanges, such as fluid cooling through internal flow of liquids, air cooling means and other passive or active cooling means yet to be developed, etc., may suffice.

Fan 120 preferably uses at least one blade 128 to pull ambient air into at least one vent 183, as shown in FIGS. 1 and 4. Further, fan 120 preferably blows the ambient air onto heat sink 114, as shown. Embodiment 102 either preferably dissipates excess heat from heat sink 114 to the ambient air or alternately preferably extracts heat from the ambient air (into heat sink 114), as needed, to maintain the at least one set-point temperature of sensitive and perishable sensitive goods 139, as shown. Also, fan 120 preferably exhausts the ambient air out through vent 183, as shown in FIGS. 1 and 4. Fan 120 preferably operates at low power to pull ambient air into at least one vent 183 and preferably exhaust the ambient air out through at least one vent 183, as shown in FIGS. 1 and 4. Blade 128 has a steep pitch for preferably sufficient air movement at the hottest rated ambient air temperature while preferably maintaining the lowest rated set-point temperature for sensitive and perishable sensitive goods 139. Input voltage to fan 120 preferably is alternately preferably determined by closed-loop feedback sensing of at least one thermocouple 124, as shown. Upon reading the teachings of this specification, those with ordinary skill in the art will now understand that, under appropriate circumstances, considering issues such as changes in technology, user requirements, etc., other controllers of forced air movers having for example heat-flux sensors, system voltage sensors yet to be developed, etc., may suffice.

The opening for blade 128 preferably to rotate within fan assembly 127 preferably is between about 5 inches and about 8 inches in diameter, depending on volume of airflow needed. Vent 183 preferably is free from any obstructions to allow proper circulation to occur, as shown in FIGS. 1 and 4. Thermo-electric assembly 123 preferably is mounted on base surface 171 of heat sink 114, as shown. Upon reading the teachings of this specification, those with ordinary skill in the art will now understand that, under appropriate circumstances, considering issues such as changes in technology, user requirements, etc., other air movers, such as, for example, turbines, propellers, etc., may suffice.

Thermo-electric assembly 123 comprises at least one thermo-electric semi-conductor node 133, as shown. More preferably, thermo-electric assembly 123 comprises a plurality of thermo-electric semi-conductor nodes 133, as shown. Even more preferably, thermo-electric assembly 123 comprises between about six and about nine thermo-electric semi-conductor nodes 133, preferably electrically connected in series, as shown in FIG. 9A (at least embodying herein wherein said at least one thermo-electric heat pump comprises a minimum of about three sandwich layers).

The quantity of thermo-electric semi-conductor nodes 133 is preferably determined by the total expected variance between a desired set-point-temperature of sensitive and perishable sensitive goods 139 and the ambient temperatures that embodiment 102 will be potentially subjected to. Once the set-point-temperature-to-ambient-temperature range of sensitive and perishable sensitive goods 139 preferably is defined, it is divided by a per-unit factor to determine the preferred number of thermo-electric semi-conductor nodes 133 that are electrically connected in series (and thermally connected in series). The per-unit factor for bismuth-telluride ($Bi_2Te_3$) based thermo-electric semi-conductor nodes, preferably ranges from about 3° C. to about 5° C. Thus, preferably, if the set-point-temperature of sensitive and perishable sensitive goods 139 is about 0° C. and the ambient temperature is expected to range up to about 27° C.; about six to about nine thermo-electric semi-conductor nodes 133 are needed. Thus, the preferred thermo-electric assembly 123 comprises about six to about nine thermo-electric semi-conductor nodes 133, that preferably are electrically connected in series (and thermally connected in series), as shown.

The per-unit factor for series-connected thermo-electric semi-conductor nodes 133, and preferably is selected to maximize the efficiency of heat pumping across thermo-electric semi-conductor nodes 133. The efficiency at which thermo-electric semi-conductor nodes 133 pump heat is largely determined by the external boundary conditions imposed on heat pumping across thermo-electric semi-conductor nodes 133. The most significant of these boundary conditions comprise the temperature gradient (change in temperature from the P-side to the N-side of the thermo-electric semi-conductor node 133) and the level of heat conductivity at the semi-conductor node boundaries.

Generally, operation that is more efficient correlates with smaller temperature gradients and with higher levels of heat conductivity at the semi-conductor node boundaries of thermo-electric semi-conductor node 133. Thus, preferably thermo-electric assembly 123 has a sufficiently large number of thermo-electric semi-conductor nodes 133 electrically connected in series (and thermally connected in series) such that no single thermo-electric semi-conductor node 133 experiences a temperature gradient greater than from about 3° C. to about 5° C. Also, preferably, thermo-electric semi-conductor nodes 133 are configured such that the level of heat conductivity at each semi-conductor node boundary preferably approximates the thermal conductivity of aluminum.

The preferred number of thermo-electric semi-conductor nodes 133 electrically connected in parallel is preferably determined by the total heat-rate that must be pumped from, or to, sensitive and perishable sensitive goods 139 such that the temperature of sensitive and perishable sensitive goods 139 preferably may be maintained at, or near, the desired set-point-temperature, preferably within from about 2 degree C. to about 8 degrees C., preferably within 1 degree C. The heat pumping capacity of each thereto-electric semi-conductor node 133, electrically connected in parallel (and thermally connected in parallel), preferably depends on specific characteristics of the specific thermo-electric semi-conductor node 133, as shown. Thus, a designer of iso-thermal transport and storage system 100 preferably would consult the manufacturer of the specific thermo-electric semi-conductor node 133 to determine its rated-heat-pumping-capacity. Additionally, the designer of iso-thermal transport and storage system 100 preferably would determine the total heat-rate that must be pumped from, or to, sensitive and perishable sensitive goods 139. Once these factors are known to the designer of iso-thermal transport and storage system 100, preferably the designer divides the total heat-rate by the rated-heat-pumping-capacity of a single series string of thermo-electric semi-conductor nodes 133, to preferably determine the required number of thermo-electric semi-conductor nodes 133, which should be electrically connected in parallel (and thermally connected in parallel).

VIP insulation 108 preferably provides a further degree of control over gradual changes in temperature by preferably decreasing heat convection, radiation and conduction and increasing thermal resistance. Preferably, about 2 lb/cu. ft. expanded urethane foam, as produced by Smooth-On model Foam-iT!™, is used for VIP insulation 108. VIP insulation 108 preferably comprises three sheets of about ½ inch thickness making a total thickness of about 1½ inches which is wrapped around inner-workings assembly 106, as shown. Height of VIP insulation 108 preferably is about 8½ inches, as shown. All VIPs preferably are encased in urethane foam to minimize damage to VIPs, making embodiment 102 more shock-resistant, as shown. Upon reading the teachings of this specification, those with ordinary skill in the art will now understand that, under appropriate circumstances, considering issues such as changes in technology, user requirements, etc., other insulating means, such as epoxies, unsaturated polyesters, phenolics, fibrous materials and foam materials yet to be developed, etc., may suffice.

FIG. 8 shows a side profile view, illustrating thermo-electric assembly 123 of iso-thermal transport and storage system 100, according to the preferred embodiment of the present invention in FIG. 1. The present invention preferably attains a high coefficient of performance (COP) using the method herein described. At least one thin non-electrically conductive layer 131 preferably electrically separates thermo-electric capacitance spacer block 125 from thermo-electric semi-conductor nodes 133, while maintaining thermal conductivity. At least one thin-film thermal epoxy 135, preferably fills microscopic imperfections between thin non-electrically conductive layer 131 and thermo-electric capacitance spacer block 125 (also see FIG. 8). Upon reading this specification, those skilled in the art will now appreciate that, under appropriate circumstances, considering such issues as future technology, cost, application needs, etc., other thermal conductivity maximizers, such as, for example, thermal greases, thermal dopes, molecularly smoothed surfaces, etc., may suffice.

Thermo-electric assembly 123 preferably comprises a plurality of thermo-electric semi-conductor nodes 133, preferably connected physically (thermally) in series and/or parallel, and electrically in series and/or parallel, and preferably using at least one battery system 119 to create at least one bidirectional heat-pump, as shown. This configuration preferably provides progressive temperature gradients and precise temperature control (at least herein embodying wherein such control of such at least one temperature comprises controlling such at least one temperature to within a tolerance of less than about one degree centigrade). Thermo-electric assembly 123 preferably is used to increase the output voltage since the voltage induced over each individual thermo-electric semi-conductor node 133 is small. Upon reading the teachings of this specification, those with ordinary skill in the art will now appreciate that, under appropriate circumstances, considering issues such as changes in technology, user requirements, etc., other heating/cooling means for example, thermoelectric refrigerators, thermo-electric generators yet to be developed, etc., may suffice.

FIG. 8 shows repetitive layers of thermo-electric capacitance spacer block 125 and thermo-electric semi-conductor node 133, which comprise thermo-electric assembly 123. Preferably, thermo-electric semi-conductor node 133 comprises bismuth-telluride that preferably is secured with electrically-conductive thermal adhesive, preferably silver-filled two-component epoxy 132, as shown. Thin-film thermal epoxy 135 preferably fills any microscopic imperfections at the interface between each layer of thermo-electric capacitance spacer block 125 and thin non-electrically conductive layer 131, as shown.

Preferably, thermo-electric semi-conductor node 133 comprises banks of electrically parallel-connected bismuth-telluride semiconductors that are in-turn electrically connected in series and interconnected to both power supply circuits and sensing/control circuits, as shown.

The overall efficiency of operation of thermo-electric assembly 123 preferably is improved with the combination of adding thermal capacitance, between each electrically series-connected (and thermally connected in series) thermo-electric semi-conductor node 133, and the ability to independently control the voltage across each series-connected thermoelectric semi-conductor node 133 (at least herein embodying wherein said at least one thermo-electric heat pump comprises at least one thermal capacitor adapted to provide at least one thermal capacitance in thermal association with said at least one thermo-electric device).

Preferably, thermo-electric capacitance spacer block 125 is the thermal capacitance added between each electrically series-connected (and thermally series-connected) thermo-electric semi-conductor node 133, as shown. Also, the voltage, across each electrically series-connected (and thermally series-connected) thermo-electric semi-conductor node 133, preferably is controlled by at least one closed-feedback loop sensory circuit, as shown. Further, preferably, the voltage, across each electrically series-connected (and thermally series-connected) thermo-electric semi-conductor node 133, preferably is independently controlled, as shown. Still further, preferably, the independently-controlled voltage impressed across each electrically series-connected (and thermally series-connected) thermoelectric semi-conductor node 133, is integrated with adjacent such independently-controlled voltages, preferably so as to ensure that under normal operational conditions, all electrically series-connected (and thermally series-connected) thermo-electric semi-conductor nodes 133 pump heat generally in the same direction, as shown. Even further, preferably, any short-term variation in voltage, impressed across each electrically series-connected (and thermally series-connected) thermo-electric semi-conductor node 133, preferably is constrained to less than about 1% of the RMS value of the voltage impressed across each electrically series-connected (and thermally series-connected) thermo-electric semi-conductor node 133.

At least one thermo-electric capacitance spacer block 125 preferably is about ¼ inch thick, and preferably is flat with parallel polished surfaces, as shown (at least embodying herein wherein such at least one thermal capacitance is user-selected to provide intended thermal association with said at least one thermo-electric device). At least one thermoelectric capacitance spacer block 125 preferably has slight indentations on parallel surfaces to allow the assembler to align thermo-electric capacitance spacer block 125 with thermo-electric semi-conductor node 133 while assembling thermo-electric assembly 123. Aluminum alloy 6061 preferably is used because of its lightweight, relatively high yield-strength of about 35000 psi, corrosion resistance, and excellent machinability. Preferred aluminum alloy 6061 is resistant to stress corrosion cracking and maintains its strength within a temperature range of about −200° C. to about +165° C. Preferred aluminum alloy 6061 is sold by McMaster-Carr as part number 9008K48. Alternately preferably, thermo-electric capacitance spacer block 125 comprises copper and copper alloys, which provide needed levels of thermal conductivity, but are not as advantageous as aluminum alloys relative to structural strength and weight considerations.

Thermo-electric capacitance spacer block 125 preferably is 'sandwiched' between each thermo-electric semi-conductor node 133 in thermo-electric assembly 123, as shown (at least embodying herein wherein each such sandwich layer comprises at least one set of said thermo-electric devices and at least one set of said thermal capacitors). Thermo-electric capacitance spacer block 125 preferably, during normal operation, provides delayed thermal reaction time (stores heat), and in conjunction with controlled operation of a plurality of thermo-electric semi-conductor nodes 133, may act to minimize variations in temperature swings for sensitive and perishable sensitive goods 139 (at least herein embodying wherein said intended thermal association of such at least one least one thermal capacitance is user-selected to provide increased energy efficiency of operation of said at least one thermoelectric device as compared to said energy efficiency of operation of said at least one thermoelectric device without addition of said at least one least one thermal capacitor).

Circuit board 117 preferably is mounted and wired to control thermo-electric assembly 123 as shown. Circuit board 117 houses circuitry (see FIG. 11) for connecting at least one thermocouple 124 such that at least one thermocouple 124 acts as a one-wire programmable digital thermometer to measure at least one temperature at thermocouple 124, as shown. Circuitry on circuit board 117 preferably also provides at least one feedback loop for control of voltage and power feeds to at least one plurality of thermo-electric semi-conductor nodes 133.

Silver-filled two-component epoxy 132 preferably is a thermal adhesive (at least embodying herein wherein each such sandwich layer is suitable for thermally-conductively connecting to at least one other such sandwich layer; and wherein thermal conductance between essentially all such attached sandwich layers is greater than 10 watts per meter per degree centigrade; and wherein thermal conductance between essentially all such attached sandwich layers is greater than 10 watts per meter per degree centigrade). Silver-filled two-component epoxy 132 preferably has a specific gravity of about 3.3, preferably is non-reactive and preferably is stable over the operating temperature range of embodiment 102. Silver-filled two-component epoxy 132 preferably is part number EG8020 from AI Technology Inc. Upon reading the teachings of this specification, those with ordinary skill in the art will now understand that, under appropriate circumstances, considering issues such as changes in technology, user requirements, etc., other materials with a high Seebeck coefficient, such as uranium dioxide, Perovskite® and other such materials yet to be developed, etc., may suffice.

Metal-to-metal contact is ideal for conducting the maximum heat transfer. However, a minute amount of thin-film thermal epoxy 135 applied provides filling of any air pockets and may increase thermal conduction between thermo-electric capacitance spacer block 125 and thermo-electric semi-conductor node 133 as shown in FIG. 8. Trapped air is about 8000 times less efficient at conducting heat than aluminum; therefore, thin-film thermal epoxy 135 preferably is used to minimize losses in interstitial thermal conductivity, as shown. The increase in efficiency is realized because the effective contact-surface-area is maximized, thereby preferably minimizing hot and cold spots that would normally occur on the surfaces. The uniformity increases the thermal conductivity as a direct result. Thin-film thermal epoxy 135 is often applied on both surfaces with a plastic spatula or similar device. Conductivity of thin-film thermal epoxy 135 is poorer than the metals it couples, therefore it preferably is important to use no more than is necessary to exclude any air gaps. Upon reading the teachings of this specification, those with ordinary skill in the art will now understand that, under appropriate circumstances, considering issues such as changes in technology, user requirements, etc., other conductor enhancements, such as, for example, other thermal adhesives, material fusion, conductive fluids or other such conductor enhancers yet to be developed, etc., may suffice.

FIG. 9A shows an electrical schematic view, illustrating electrical control of iso-thermal transport and storage system 100, according to the preferred embodiment of FIG. 1. According to preferred embodiments of the present invention, the multiple temperature staging process preferably is accomplished by having at least two thermo-electric semiconductor nodes 133 that, when wired in series, preferably combine to form thermo-electric assembly 123, as shown. Additional thermo-electric semi-conductor nodes 133 preferably may be electrically series-connected (and thermally series-connected) or electrically parallel connected (and thermally series-connected) preferably to extend the heat-pumping capabilities of thermo-electric assembly 123, as shown.

Individual battery cells in at least one battery system 119 preferably may be wired to preferably switch between combinations of series and/or parallel depending on specific power available or if user 200 desires that particular design, as shown. At least one serial/parallel conversion relay 187 preferably provides switching between combinations of series and/or parallel modes. Serial/parallel conversion relay 187 preferably comprises double pole double throw (DPDT). Serial/parallel conversion relay 187 preferably further comprises a latching type of relay, which does not require continuous power to remain in either position. Upon reading the teachings of this specification, those with ordinary skill in the art will now appreciate that, under appropriate circumstances, considering issues such as changes in technology, user requirements, etc., other relay switching means, such as dual coil, non-latching, reed relays, pole and throw relays, mercury-wetted relays, polarized relays, contactor relays, solid-state relays, Buchholz relays, or other current switching means yet to be developed, etc., may suffice.

When increased voltage is supplied to selected layers of thermo-electric assembly 123 these sandwiched layers preferably are capable of pumping heat at higher rates, as required to ensure that the temperature of sensitive and perishable sensitive goods 139 preferably is maintained over a wide range of ambient conditions, as shown. This variation in heat pumping rate with each sandwiched layer of thermo-electric assembly 123 is allowed since at least one thermo-electric capacitance spacer block 125 preferably is provided between each thermo-electric semi-conductor node 133, as shown. Each at least one thermo-electric capacitance spacer block 125 preferably allows a buffering (momentary storage) of heat between adjacent thermo-electric semi-conductor nodes 133, as shown. This buffering preferably allows each thermo-electric semi-conductor node 133 flexibility to preferably pump heat at varying rates while preferably maintaining overall heating or cooling rates as required so as to preferably maintain sensitive and perishable sensitive goods 139 at or near its desired temperature set-point. Upon reading the teachings of this specification, those with ordinary skill in the art will now understand that, under appropriate circumstances, considering issues such as changes in technology, user requirements, etc., other isolating means for example shims, blocks, chocks, chunks, cleats, cotters, cusps, keystones, lumps, prongs, tapers made of metallic and non-metallic materials yet to be developed, etc., may suffice.

Battery system 119 preferably may comprise three each about 1.2 volt DC rechargeable batteries wired in series to thermo-electric assembly 123. Nominal capacity of this preferred configuration of battery system 119 is about 10000 ampere-hour (Ah) with a minimum capacity of about 9500 milliampere-hour (mAh) per 1.2 VDC rechargeable battery. Maximum charging current of this preferred configuration of battery system 119 is about of about 5 A. Battery system 119 preferably comprises Powerizer rechargeable battery part number MH-D10000APZ, preferably having a maximum discharging current of about 30 A. Preferably, dimensions of each battery are about 1.24 inches by about 2.36 inches. Preferably, each battery weighs about 5.7 ounces and has a cycle performance of above about 80% of initial capacity at 1000 cycles at about 0.1° C. discharge rate.

Heat pumping rates, between sensitive and perishable sensitive goods 139 and the ambient air surrounding iso-thermal transport and storage system 100, preferably may be actively increased or decreased by thermo-electric assembly 123 within iso-thermal transport and storage system 100, as shown. The direction of the heat pumping within this system preferably is fully reversible and available upon instant demand. Changing the polarity of the voltage of battery system 119, as applied across thermo-electric assembly 123, preferably causes heat to be pumped in opposite directions (either from the ambient surrounding iso-thermal transport and storage system 100 to sensitive and perishable sensitive goods 139, or from sensitive and perishable sensitive goods 139 to the ambient surrounding iso-thermal transport and storage system 100). Changes in the level of voltage, at which power from battery system 119 is applied across thermo-electric assembly 123, preferably cause heat to be pumped, by thermo-electric assembly 123, at greater or lesser rates. The combination of controlling the polarity, and the magnitude, of voltage from battery system 119 preferably allows sensitive and perishable sensitive goods 139 preferably to be maintained near a predetermined set-point temperature. The predetermined set-point temperature preferably is maintained as the ambient temperature varies widely. This allows the integrity of sensitive and perishable sensitive goods 139 preferably to be maintained over a wide range of ambient conditions. Also, this allows the integrity of sensitive and perishable sensitive goods 139 preferably to be maintained for long transporting-distances, or long storage-time periods, or both. The duration of the long transporting-distances or the long storage-time periods is largely determined by a combination of the total stored energy in battery system 119 and the rate at which that energy is dissipated into thermo-electric assembly 123, as shown. Upon reading the teachings of this specification, those with ordinary skill in the art will now appreciate that, under appropriate circumstances, considering issues such as changes in technology, user requirements, etc., other voltage regulating means for example multi-output pulse-width modulation power supplies, flyback-regulated converters, magnetic amplifier/switching power supplies yet to be developed, etc., may suffice.

Figure 9B:
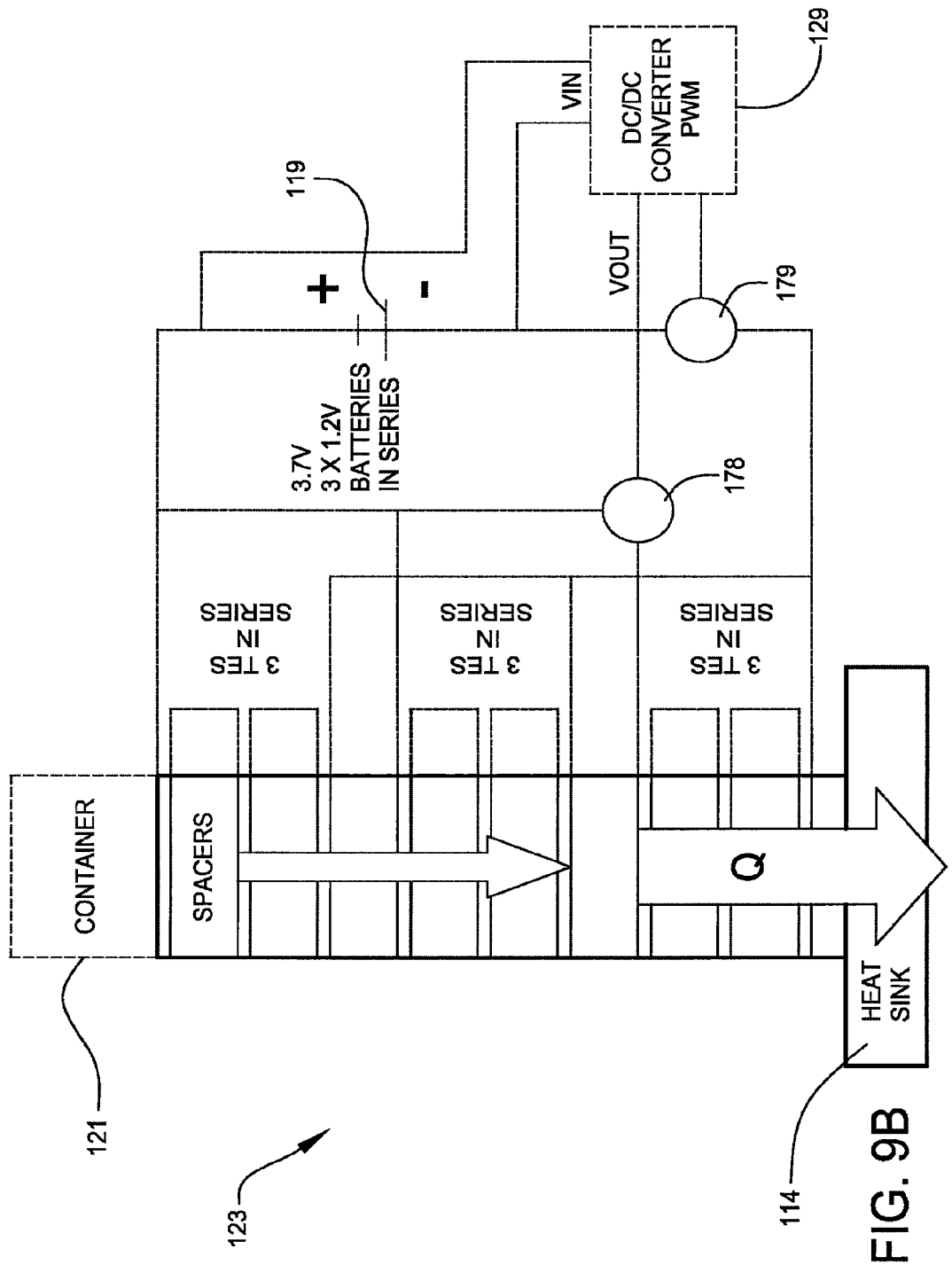
FIG. 9B shows an electrical schematic view, illustrating an alternately preferred electrical control of the iso-thermal transport and storage system, according to the preferred embodiment of FIG. 1.

FIG. 9B shows an electrical schematic view, illustrating an alternately preferred electrical control of iso-thermal transport and storage system 100, according to the preferred embodiment of FIG. 1.

Thermo-electric assembly 123 alternately preferably may operate with pulse-width modulation based voltage control, as shown. Such pulse-width modulation voltage control is not limited to about 1.2, 2.4, 3.6, 4.8 or 12 VDC battery-string voltages. Rather, the pulse-width modulation based voltage control preferably can be varied as needed to achieve intermediate voltages consistent with maintaining constant temperature within at least about 1° C., as shown in FIG. 9B (at least herein embodying wherein such control of such at least one temperature comprises controlling such at least one temperature to within a tolerance of less then one degree centigrade).

Pulse-width modulation preferably uses a square wave, wherein the duty cycle is modulated, so as to vary the average value of the resulting voltage waveform. The output voltage of the pulse-width modulation voltage-control preferably is smooth, as shown. The output voltage preferably has a ripple factor of less than about 10% of the RMS (root mean square) output voltage, and preferably results in less than about 1% variation in the change in temperature across thermo-electric assembly 123 (at least herein embodying wherein said intended thermal association is user-selected to control usage of proportional control circuitry in combination with at least one energy store to power said at least one thermo-electric heat pump to control such at least one temperature of the temperature-sensitive goods).

At least one DC/DC converter 129 preferably is a switch-mode converter, which preferably provides output voltages that are greater than its input voltage, as shown. Input voltage for DC/DC converter 129, as preferably utilized in iso-thermal transport and storage system 100, preferably is sourced from at least one battery system 119. DC/DC converter 129 preferably provides output power at voltages in excess of battery system 119, as shown. This attribute of DC/DC converter 129 preferably allows substantial flexibility in the operation of iso-thermal transport and storage system 100, particularly the operation of fan 120, as shown. Powering fan 120 at higher input voltages, are available directly from battery system 119, results in fan 120 operating at higher speeds (revolutions per minute) and thus higher cooling rates. Thus, varying the input voltage into fan 120 also preferably varies the ability of iso-thermal transport and storage system 100 to dissipate heat. Increasing input voltage into fan 120, above the output voltage available from battery system 119, also preferably increases the highest ambient temperatures at which iso-thermal transport and storage system 100 can operate. Additionally, increasing the voltage across thermo-electric assembly 123 also preferably increases the rate at which thermo-electric assembly 123 pumps heat from sensitive and perishable sensitive goods 139 to the ambient (when operating in cooling mode), or from the ambient to sensitive and perishable sensitive goods 139 (when operating in heating mode). Thus, the addition of DC/DC converter 129 preferably is highly useful for extending the operational flexibility iso-thermal transport and storage system 100.

Power from battery system 119, entering into DC/DC converter 129 or directly into at least one thermo-electric semi-conductor node 133, preferably exits passing through at least one relay 178 and at least one relay 179. Relay 178 and relay 179 preferably are momentary latching relay(s) that preferably perform as electrical switches that preferably open and close under of at least one control of monitoring circuitry on circuit board 117. Relay 178 and relay 179 are preferably latching relays, meaning they require control power only during the time that they switch from their on-to-off state or switch from off-to-on state, thus minimizing control power usage (at least embodying herein wherein said intended thermal association of such at least one thermal capacitance is user-selected to allow usage of momentary-relay-based control circuitry in combination with at least two energy stores to power said at least one thermo-electric device to achieve control of at least one temperature of the temperature-sensitive goods).

Relay 178 and relay 179 preferably are double pole, double throw (DPDT), preferably latching-style relays. Relay 178 and relay 179 preferably are digital, high-sensitivity low-profile designs, which may withstand voltage surges meeting FCC Part 68 regulation. Relay 178 and relay 179 preferably are a low-signal style G6A as manufactured by Omron. A standard dual-coil latching relay 178 and relay 179 preferably are part number G6AK-234P-ST-US. Specifications on this preferred relay include a rated voltage of about 5 VDC, a rated current of about 36 mA and a coil resistance of about 139 ohm ($\Omega$). A minimal power preferably is consumed during the latching operation of relay 178 and relay 179. Upon reading the teachings of this specification, those with ordinary skill in the art will now appreciate that, under appropriate circumstances, considering issues such as changes in technology, user requirements, etc., other relay switching means, such as dual coil, non-latching, reed relays, pole and throw relays, mercury-wetted relays, polarized relays, contactor relays, solid-state relays, Buchholz relays, or other current switching means yet to be developed, etc., may suffice.

Iso-thermal transport and storage system 100 preferably operates most efficiently when thermo-electric assembly 123 is electrically wired in series, as shown. However, thermo-electric assembly 123 preferably may be wired in various combinations of series and parallel, as a means of adjusting the heat-pumping rate, as shown. Thus, iso-thermal transport and storage system 100 preferably operates efficiently when the wiring of thermoelectric assembly 123 preferably can be switched as needed to mirror the heat-pumping demand, as that demand changes with time, as shown. Iso-thermal transport and storage system 100 preferably provides such operational efficienctly by switching the input voltages into thermo-electric assembly 123 using at least one relay 178 and at least one relay 179. At least one relay 178 and at least one relay 179 preferably switch available voltages, from battery system 119, without continuously dissipating energy. Monitoring circuitry on circuit board 117 preferably monitors the status of at least one relay 178 and at least one relay 179 to preferably prevent unnecessary energizing of outputs if at least one relay 178 and at least one relay 179 are already at a desirable position (at least herein embodying wherein said at least one thermo-electric heat pump comprises at least one first such sandwich layer comprising such set of said thermo-electric devices; wherein each thermo-electric device comprising said plurality is electrically connected in parallel with each other each thermo-electric device comprising said plurality; and wherein each of set of said thermo-electric devices comprising such first sandwich layer is thermally connected in series with each other sandwich layer). Upon reading the teachings of this specification, those with ordinary skill in the art will now appreciate that, under appropriate circumstances, considering issues such as changes in technology, user requirements, etc., other power conservation means other energy-efficient switching means, such as control devices, incremental power storage means yet to be developed, etc., may suffice.

At least one DC/DC converter 129 preferably utilizing pulse-width modulation (hereinafter "PWM") may be incorporated into circuitry on circuit board 117 preferably to boost voltage to thermo-electric semi-conductor nodes 133 preferably when higher rates of heat pumping is required. Such higher voltages, applied to thermo-electric semi-conductor nodes 133, preferably permit higher rates-of-change in temperature, thus preferably increasing the heat transfer rate in that portion of thermo-electric assembly 123, as shown. This preferably acts to remove excessive heat from the portions of thermo-electric assembly 123, as shown. Once the temperature of sensitive and perishable sensitive goods 139 is normalized, the system may preferably return to normal high efficiency operation.

Figure 10:
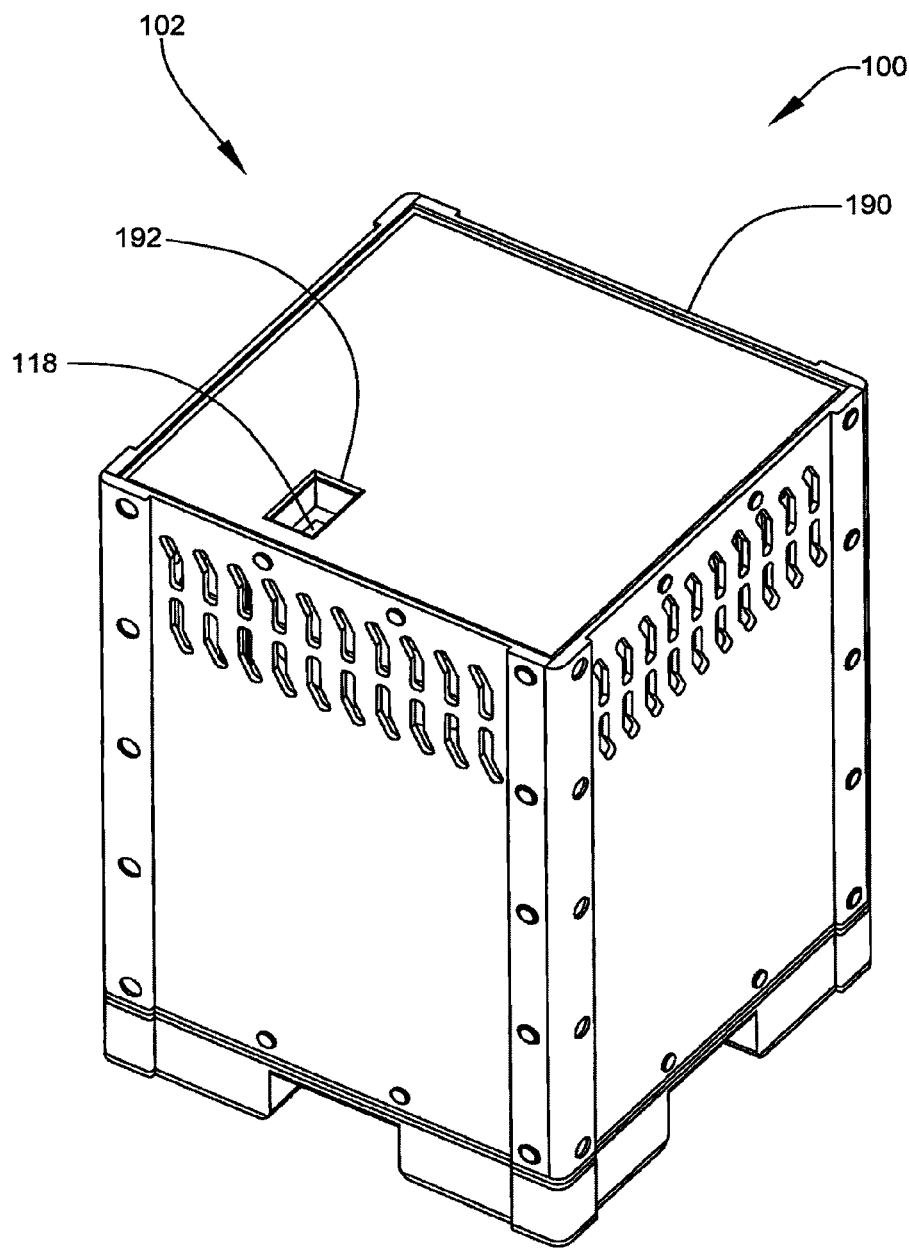
FIG. 10 shows a perspective view illustrating the preferred embodiment, of the iso-thermal transport and storage system as viewed from underneath, of the present invention of FIG. 11 shows a schematic view, illustrating a control circuit board, according to the preferred embodiment of the present invention in FIG. 1.

FIG. 10 shows a perspective view illustrating preferred embodiment 102, of iso-thermal transport and storage system 100 as viewed from underneath, of the present invention in FIG. 1. Safety on/off switch 118 preferably is mounted on horizontal upper-surface 191 (see FIG. 3) of base portion 190. Base portion 190 preferably measures about 9 inches wide by about 9 inches long. User 200 preferably activates or deactivates safety on/off switch 118 on iso-thermal transport and storage system 100, preferably by moving it to the appropriate position. At least one recess 192 preferably is provided, as shown, preferably to allow safety on/off switch 118 to be protected from accidental switching causing iso-thermal transport and storage system 100 to cease operation. This recessed design of safety on/off switch 118 preferably serves to prevent iso-thermal transport and storage system 100 from operating when not required or, more dangerously, preferably not operating when necessary. A simple mishap such as inadvertently bumping the switch to the off position may allow iso-thermal transport and storage system 100 to return to ambient environmental temperature, which may damage or destroy sensitive and perishable sensitive goods 139. The danger in accidental shutoff of safety on/off switch 118 is that at least one required temperature-range of sensitive and perishable sensitive goods 139 protected in vessel 121 is compromised. Recess 192 preferably is about 1⅓ inches wide, about ⅞ inch long and about 1 inch deep. Upon reading the teachings of this specification, those with ordinary skill in the art will now appreciate that, under appropriate circumstances, considering issues such as changes in technology, user requirements, etc., other switching means for example, actuators, triggers, activators or other such switching means yet to be developed, etc., may suffice.

Embodiment 102 is designed to be hardened relative to mechanical shock, thereby creating extended expected usable-life and cost-effectiveness for user 200, during normal transport and storage conditions, as shown. Upon reading the teachings of this specification, those with ordinary skill in the art will now understand that, under appropriate circumstances, considering issues such as changes in technology, user requirements, etc., other shock protectors, such as, for example, pads, buffers, fillings, packings or other such shock protecting means yet to be developed, etc., may suffice.

Figure 11:
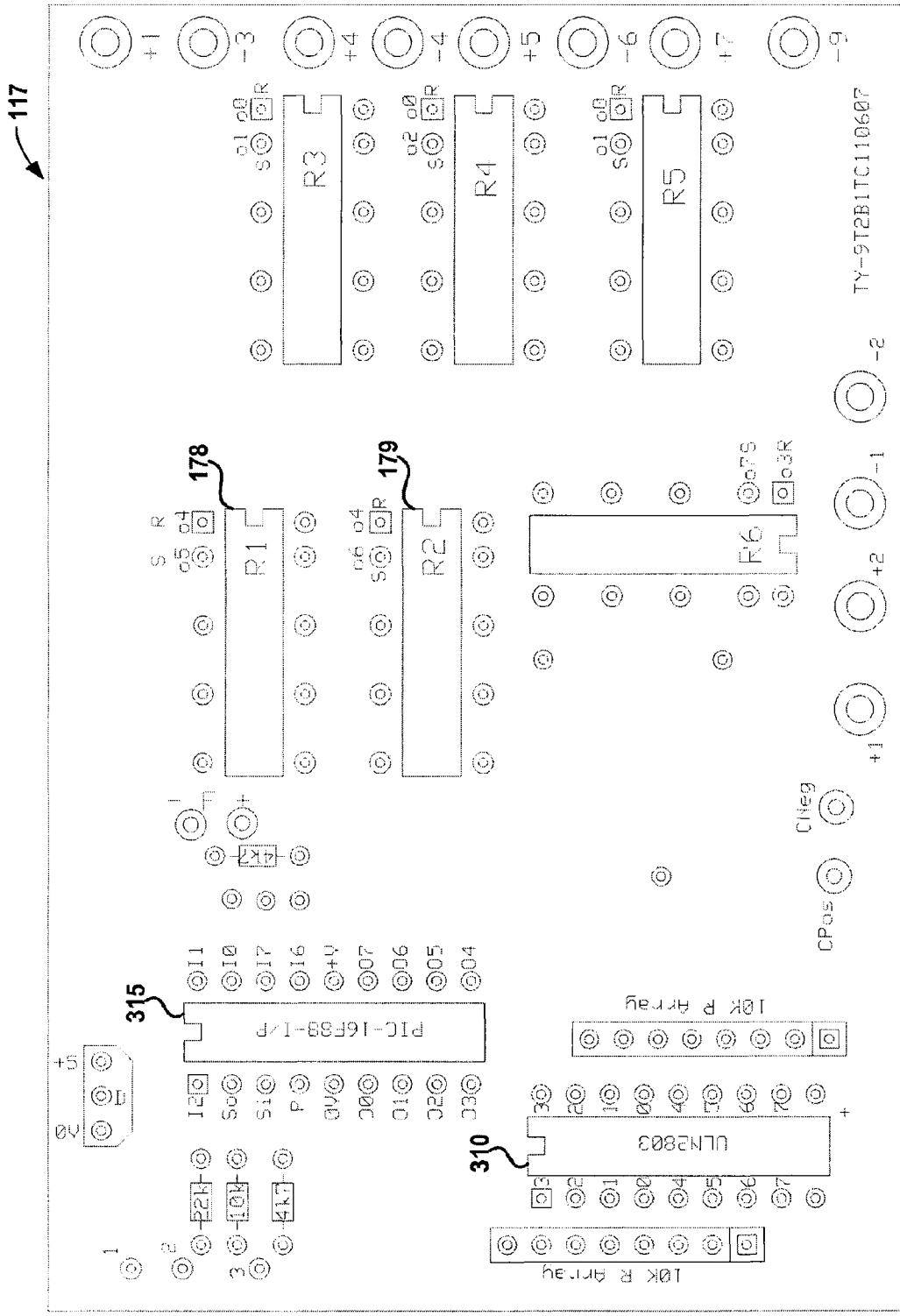

FIG. 11 shows a schematic view, illustrating a control circuit board, according to the preferred embodiment of the present invention in FIG. 1. Circuit board 117 preferably uses a series P-1 linear analog controller 315, preferably PIC-16F88-1/P, with an output of 0-5 VDC, corresponding to a thermistor range of about 0-50 thousand ohms (KΩ) or about 0-500 KΩ. Series P-1 linear analog controller 315 preferably is provided with temperature set-point, maximum current set-point, loop gain and integral-time single-turn adjustment potentiometers. High current-levels may be applied to control actuators, preferably relay 178 and relay 179, while preferably maintaining low power on circuit board 117. Heat preferably may be pumped in either direction, to or away from, sensitive and perishable sensitive goods 139, as shown in FIG. 6 according to desired temperature setting (set-point temperature of sensitive and perishable sensitive goods 139). Upon reading the teachings of this specification, those with ordinary skill in the art will now appreciate that, under appropriate circumstances, considering issues such as changes in technology, user requirements, etc., other controller means, such as other circuit boards, temperature monitors yet to be developed, etc., may suffice.

FIG. 11 shows the control circuit board physical layout for circuit board 117. FIG. 11 shows a preferable pin-configuration for relay-driver device ULN2803 310. FIG. 11 also shows a preferable pin-configuration for series P-1 linear analog controller 315. Additionally, FIG. 11 further shows preferred pin-configurations for relay 178 and relay 179. Potential additional control relays R3, R4, R5, and R6 are also shown in FIG. 11. Upon reading this specification, those skilled in the art will now appreciate that, under appropriate circumstances, considering such issues as future technologies, cost, space limitations, etc., other circuit board layouts, such as, for example, single integrated chip layouts, size variant layouts (longer, wider, shorter, etc.), stacked layouts, multi-board layouts, etc., may suffice.

The wiring connections between thermo-electric assembly 123 and at least one battery system 119 preferably use soldered connections, as shown. Circuit board 117 preferably comprises G10 epoxy-glass board, preferably about 1/16 inches thick, about 2½ inches wide and about 3⅞ inches long, preferably with one-ounce etched-copper conductors on at least one side, as shown.

Solder comprises a fusible metal alloy, preferably with a melting range of about 90° C. to about 450° C. Solder preferably is melted to join the metallic surfaces of the wire 177 to circuit board 117. Flux cored wire solder preferably is used, such as Glow Core, marketed by AIM. Solder preferably is lead-free compatible, preferably has excellent wetting properties, preferably has a wide process-time window and preferably is cleanable with a CFC-free cleaning solution, designed for use in ultrasonic cleaning or spray and immersion systems, preferably Total Clean 505 as manufactured by Warton Metals Limited. Alternately preferably, other metals such as tin, copper, silver, bismuth, indium, zinc, antimony, or traces of other metals may be used within the solder mixture. Also, lead-free solder replacements for conventional tine-lead (Sn60/Pb40 and Sn63/Pb37) solders, preferably having melting points ranging from about 118° C. to about 340° C., which do not damage or overheat circuit board 117 during soldering processes, are utilized.

Alternately preferably, other alloys, such as, for example, tin-silver-copper solder ($SnAg_{3.9}Cu_{0.6}$) may be used, because it is not prone to corrosion or oxidation and has resistance to fatigue. Additionally, preferably, mixtures of copper within the solder formulations lowers the melting point, improves the resistance to thermal cycle fatigue and improves wetting properties when in a molten state. Mixtures of copper also retard the dissolution of copper from circuit board 117. Upon reading the teachings of this specification, those with ordinary skill in the art will now appreciate that, under appropriate circumstances, considering issues such as changes in technology, user requirements, etc., other wiring controlling means, such as boards, cards, circuit cards, motherboards yet to be developed, or other combinations of solder including $SnAg_{3.0}Cu_{0.5}$, $SnCu_{0.7}$, $SnZn_9$, $SnIn_{8.0}Ag_{3.5}Bi_{0.5}$, $SnBi_{57}Ag_1$, $SnBi_{58}$, $SnIn_{52}$ and other possible flux and alloy solder formulations, etc., may suffice.

Figure 12A:
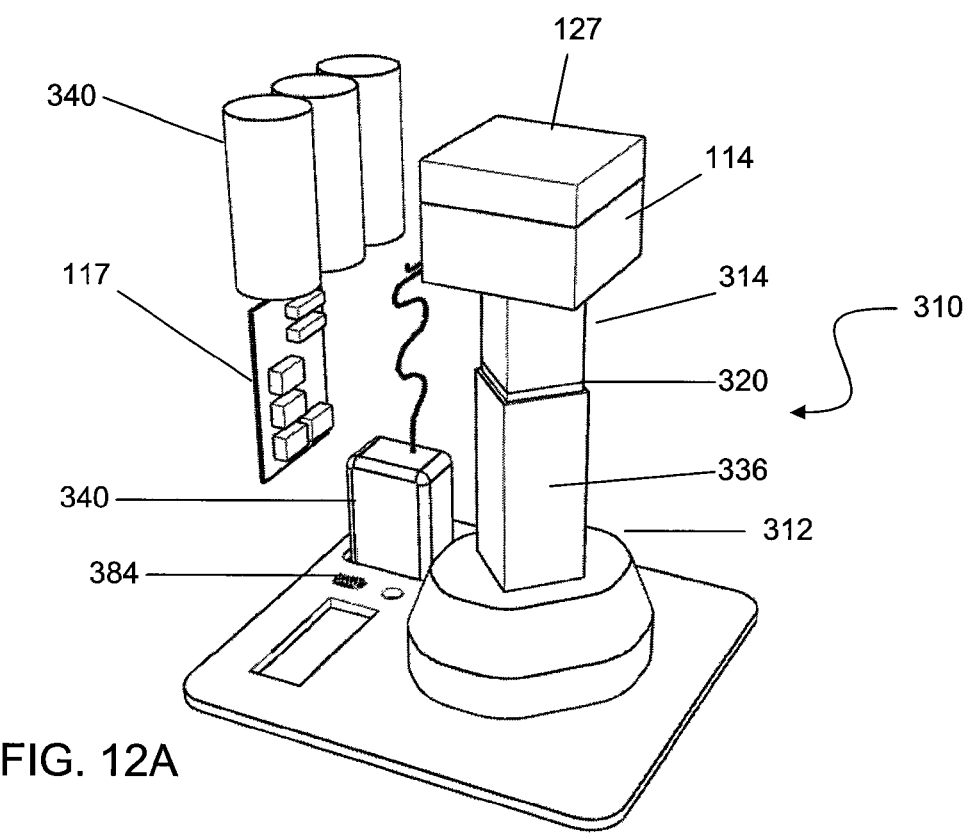
FIGS. 12A-B shows perspective views, illustrating a thermoelectric transport and storage device, according to a preferred embodiment of the present invention.

FIG. 12A illustrates a preferred embodiment of thermoelectric heat pump assembly 310. In this preferred embodiment, thermoelectric heat pump assembly 310 has a top end 312 and a bottom end 314, thermoelectric heat pump assembly 310 comprising at least one thermoelectric unit layer 320 capable of active use of the Peltier effect. Thermoelectric heat pump assembly 310 further comprises a capacitance spacer block 125 suitable for storing heat and providing a delayed thermal reaction time of the assembly 310, wherein the capacitance spacer block 125 is thermally connected to thermoelectric unit layer 320. Assembly 310 further comprises: at least one energy source 340 operably connected to the at least one thermoelectric unit layer 320, wherein the energy source 340 is suitable to provide a current; a heat sink 114 associated with a fan assembly 127, wherein in the heat sink 114 is thermally connected at the bottom end of the heat pump assembly 310, the heat pump assembly 310 being thermally connected to an isolation chamber 336, and wherein the thermoelectric heat pump assembly 310 further comprises a circuit board 117.

Figure 12B:
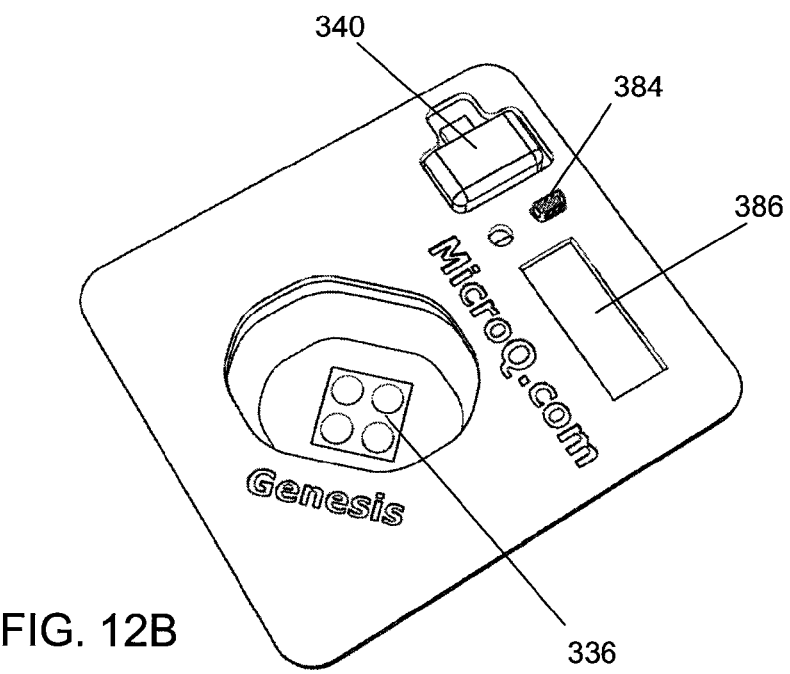

FIG. 12B shows a top view of another preferred embodiment of thermoelectric transport and storage device 102, showing: a thermal isolation chamber 336, an LCD display 386, at least one energy source 340, and a DB connector 384.

Figure 13A:
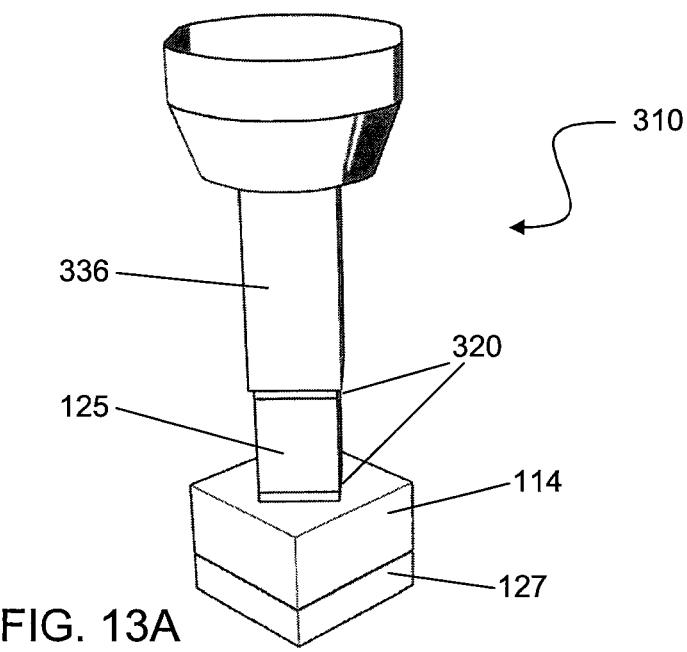
FIGS. 13A-B shows perspective views, illustrating a thermoelectric heat pump assembly with two thermoelectric unit layers, according to a preferred embodiment of the present invention, and a thermoelectric transport and storage device with a robust shock proof exterior, according to a preferred embodiment of the present invention.

FIG. 13A shows another preferred embodiment of thermoelectric heat pump assembly 310, the assembly 310 comprising: two thermoelectric unit layers 320 capable of active use of the Peltier effect, each thermoelectric unit layer 320 having a cold side 322 and a hot side 324 (See FIG. 15); at least one capacitance spacer block 125 suitable for storing heat and providing a delayed thermal reaction time of the assembly 310, the capacitance spacer block 125 being between a first thermoelectric unit layer 332 and a second thermoelectric layer 334 (See FIG. 15), wherein the top portion 326 of the capacitance spacer block 125 is thermally connected to the hot side 324 of the first thermoelectric unit layer 332 and the bottom portion 328 is thermally connected to the cold side 322 of the second thermoelectric unit layer 334 (See FIG. 15), thereby forming a sandwich layer 330 suitable to pump heat from the first thermoelectric unit layer 332 to the second thermoelectric layer 334 (See FIG. 15); and a heat sink 114 associated with a fan assembly 127, wherein the heat sink 114 is thermally connected at the bottom end 314 of the heat pump assembly 310.

Figure 13B:
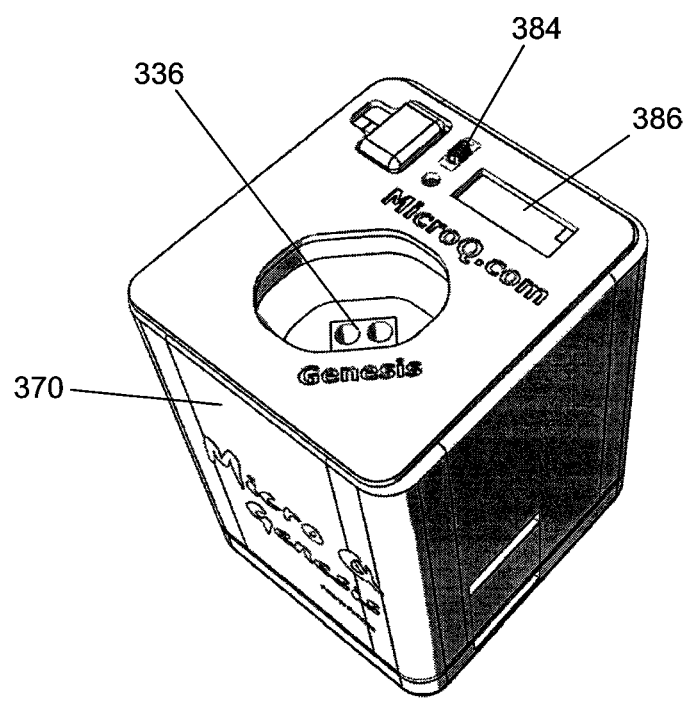

FIG. 13B shows a perspective view of another preferred embodiment of thermoelectric transport and storage device 102, wherein the transport and storage device 102 includes: a thermal isolation chamber 336, a robust shock proof exterior 370, an LCD display 386, at least one energy source 340, and a DB connector 384.

Figure 14:
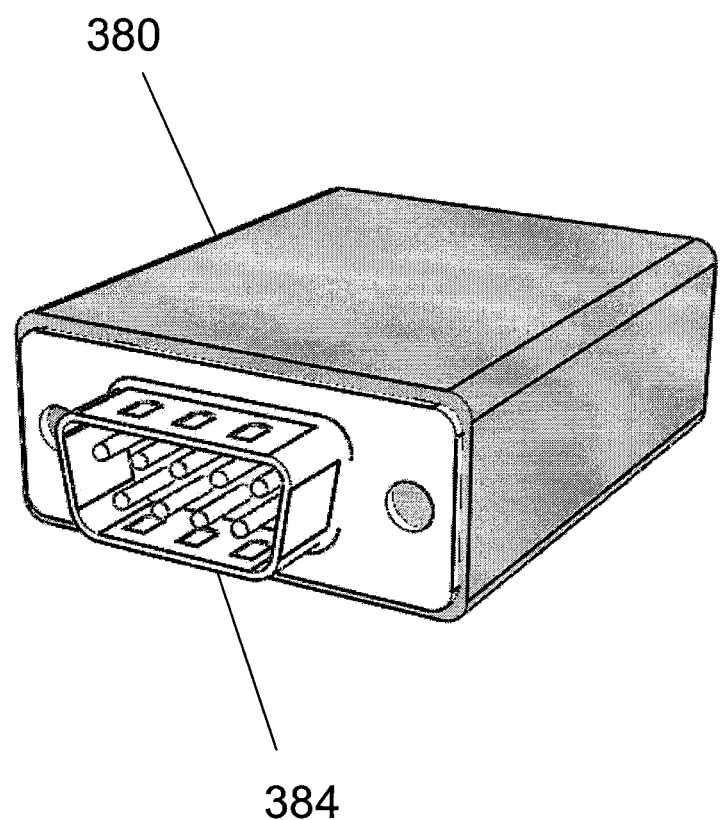
FIG. 14 shows a perspective view, illustrating a portable microprocessor, according to a preferred embodiment of the present invention.

FIG. 14 shows a perspective view, illustrating a portable microprocessor 380, according to a preferred embodiment of the present invention. In one embodiment, a portable microprocessor 380 may be utilized to communicate with the thermoelectric transport or storage device 102 (See FIG. 13B) to send and receive time and temperature profiles related to the thermoelectric heat pump 310. The sending and receiving of time and temperature profiles between the portable microprocessor 380 and thermoelectric transport or storage device 102 may either be directly through DB connectors 384 or alternatively through radio-frequency identification (RFID) tags. When the portable microprocessor 380 is sending or receiving time and temperature profiles directly through the DB connectors 384 or RFID tag the thermoelectric transport or storage device's 102 energy source 340 may supply the needed power to activate the portable microprocessor 380. The amount of power generally needed to activate the portable microprocessor 380 is 5 volts. Upon activation, the portable microprocessor 380 may then communicate with an electrically-erasable programmable ROM (EEPROM) rewritable memory chip 382 operatively associated with the thermoelectric transport or storage device 102. Such communication between the portable microprocessor 380 and EEPROM rewritable memory chip 382 may be through a serial protocol by way of a multi-master serial computer bus. During communication the portable microprocessor 380 may also receive the time and temperature profiles from the EEPROM rewritable memory chip 382 and configure new time and temperature profiles for the EEPROM rewritable memory chip 382 relating to the thermoelectric heat pump 310. For instance, the portable microprocessor 380 may reconfigure the time for activating a series of thermoelectric unit layers 320 upon reaching a specified temperature.

Figure 15:
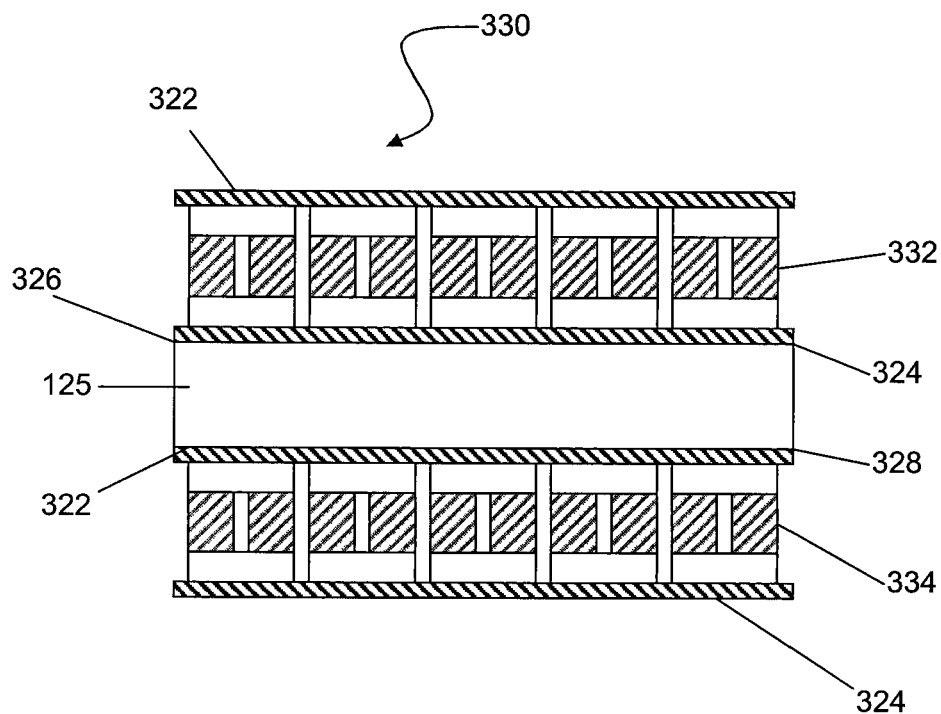
FIG. 15 shows a side profile view, illustrating a sandwich layer, according to a preferred embodiment of the present invention.

FIG. 15 shows a side profile view, illustrating a sandwich layer 330, according to a preferred embodiment of the present invention. The sandwich layer 330 comprises at least one capacitance spacer block 125 suitable for storing heat and providing a delayed thermal reaction time of the assembly 310, the capacitance spacer block 125 having a top portion 326 and a bottom portion 328 and being between a first thermoelectric unit layer 332 and a second thermoelectric layer 334, wherein the top portion of the capacitance spacer block 125 is thermally connected to the hot side 324 of the first thermoelectric unit layer 332 and the bottom portion 328 is thermally connected to the cold side 322 of the second thermoelectric unit layer 334, thereby forming a sandwich layer 330 suitable to pump heat from the first thermoelectric unit layer 332 to the second thermoelectric layer 334.

Figure 16:
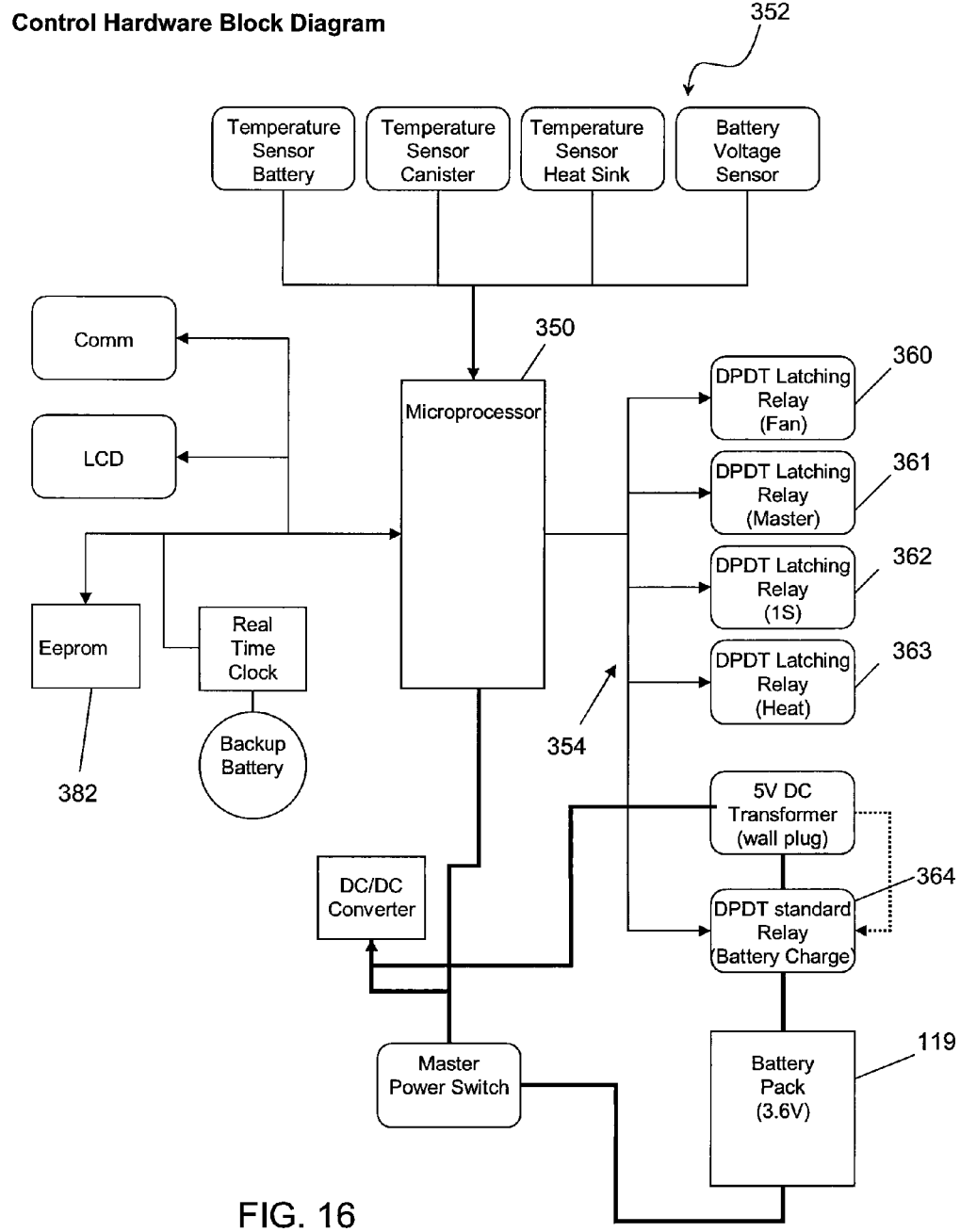
FIG. 16 shows a schematic view of a control hardware block diagram, illustrating momentary relay based circuitry programmable by a microprocessor adapted to control the temperature of temperature sensitive goods based on a preferred temperature profile, according to a preferred embodiment of the present invention.

FIG. 16 shows a microprocessor 350 operatively associated with the thermoelectric heat pump assembly 310. As shown, microprocessor 350 communicates with EEPROM chip 382 to obtain instructions for operating at least one double-pole double-throw (DPDT) relay 360-364. The communication between microprocessor 350 and EEPROM chip 382 may include the sequencing of DPDT relays 360-364. For instance, microprocessor 350 may communicate with relays 360-364 to place thermoelectric unit layers 320 in series or parallel depending on the temperature of a canister, wherein the canister is comprised of the thermal isolation chamber 336 (see FIG. 12A).

Other communication between microprocessor 350 and DPDT relays 360-364 may include allocating power from battery 119 or alternative 5 volt direct-current (DC) transformer to various parts of the thermoelectric transport or storage device 102, such as fan assembly 127 (see FIG. 12A). A DC-to-DC converter, consisting of an inverter followed by a step-up or step-down transformer and rectifier may also be used to supply direct-current to microprocessor 350. In addition, microprocessor 350 communicates with LCD display 386 (see FIG. 12B) to convey information wherein microprocessor 350 is powered by a 3.6 volt battery pack which is connected by way of a master power switch.

Figure 17:
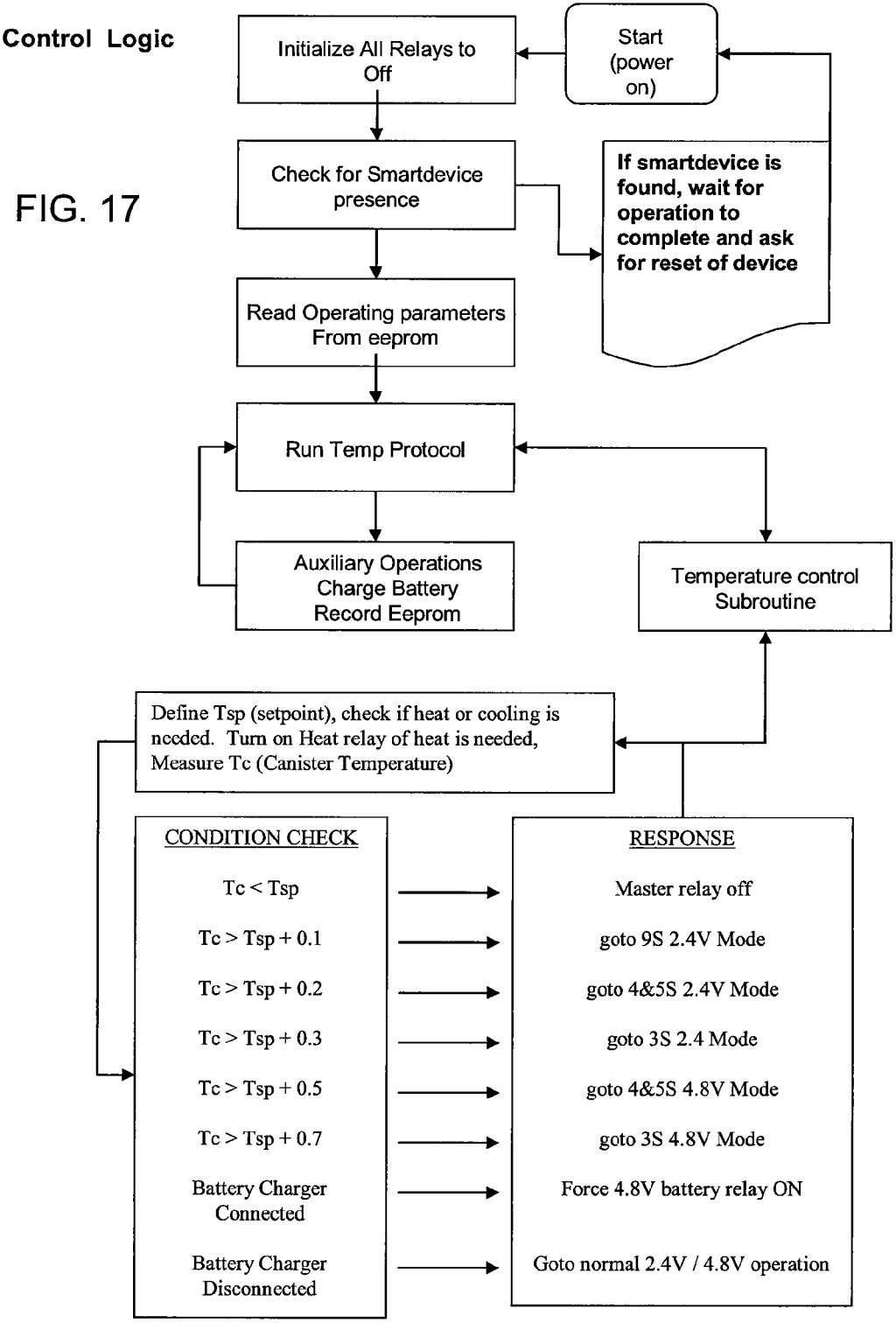
FIG. 17 shows a schematic view of a control logic diagram, illustrating a control illustrating

In another embodiment, as shown in FIG. 17, a portable microprocessor 380 i.e., "Smartdevice" (see FIG. 14) communicates with EEPROM chip 382 through a multi-master serial computer bus using I2C protocol to convey time and temperature profiles relating to the thermoelectric unit layers 320. Initially, as the power is turned on for the thermoelectric transport or storage device 102, all relays 360-364 are initially off. Next, microprocessor 350 of thermoelectric transport or storage device 102 checks for the presence of a portable microprocessor 380. If a portable microprocessor 380 is found the microprocessor 350 waits for operations to complete and ask user to reset. From this point, microprocessor 350 reads operating parameters from EEPROM chip 382. Microprocessor 350 may then receive temperature protocols and auxiliary operations of charging battery and recording EEPROM chip 382.

As shown in FIG. 17 and FIG. 18, temperature control subroutines are conveyed by microprocessor 350 to relays 360-364. The subroutines, define a setpoint temperature (Tsp) and control relays 360-364 to place thermoelectric unit layers 320 in series or parallel depending on Tsp and canister temperature (Tc), wherein the canister is comprised of the thermal isolation chamber 336 (see FIG. 12A). For instances, in one embodiment the subroutines may include the following instructions: 1) if Tc<Tsp, then turn relay off; 2) if Tc>(Tsp+0.1° C.), then switch to 9S and 2.4 volt mode; 3) if Tc>(Tsp+0.2° C.), then switch to 4&5S and 2.4 volt mode; 4) if Tc>(Tsp+0.3° C.), then switch to 3S and 2.4 volt mode; 4) if Tc>(Tsp+0.5° C.), then switch to 4&5S and 4.8 volt mode; 5) if Tc>(Tsp+0.7° C.), then switch to 3S and 4.8 volt mode; 6) if the battery charger is connected, then force 4.8 volt battery relay on; and 7) if batter charger is disconnected; then switch to normal 2.4 volt/4.8 volt operation.

As shown in FIG. 18, in another embodiment the subroutines may include the following instructions: 1) if Tc<Tsp, then turn relay off; 2) if Tc>(Tsp+0.1° C.), then switch to 6S and 3.6 volt mode; 3) if Tc>(Tsp+0.2° C.), then switch to 3S and 3.6 volt mode; 4) if Tc>(Tsp+0.3° C.), then switch to 2S and 3.6 volt mode; and 5) if Tc>(Tsp+0.5° C.), then switch to 1S and 3.6 volt mode. In yet another embodiment, the subroutines may include the following instructions: 1) if Tc<Tsp, then turn relay off; 2) if Tc>(Tsp+0.2° C.), then switch to 2S and 3.6 volt mode; and 3) if Tc>(Tsp+0.5° C.), then switch to 1S and 3.6 volt mode.

Figure 19:
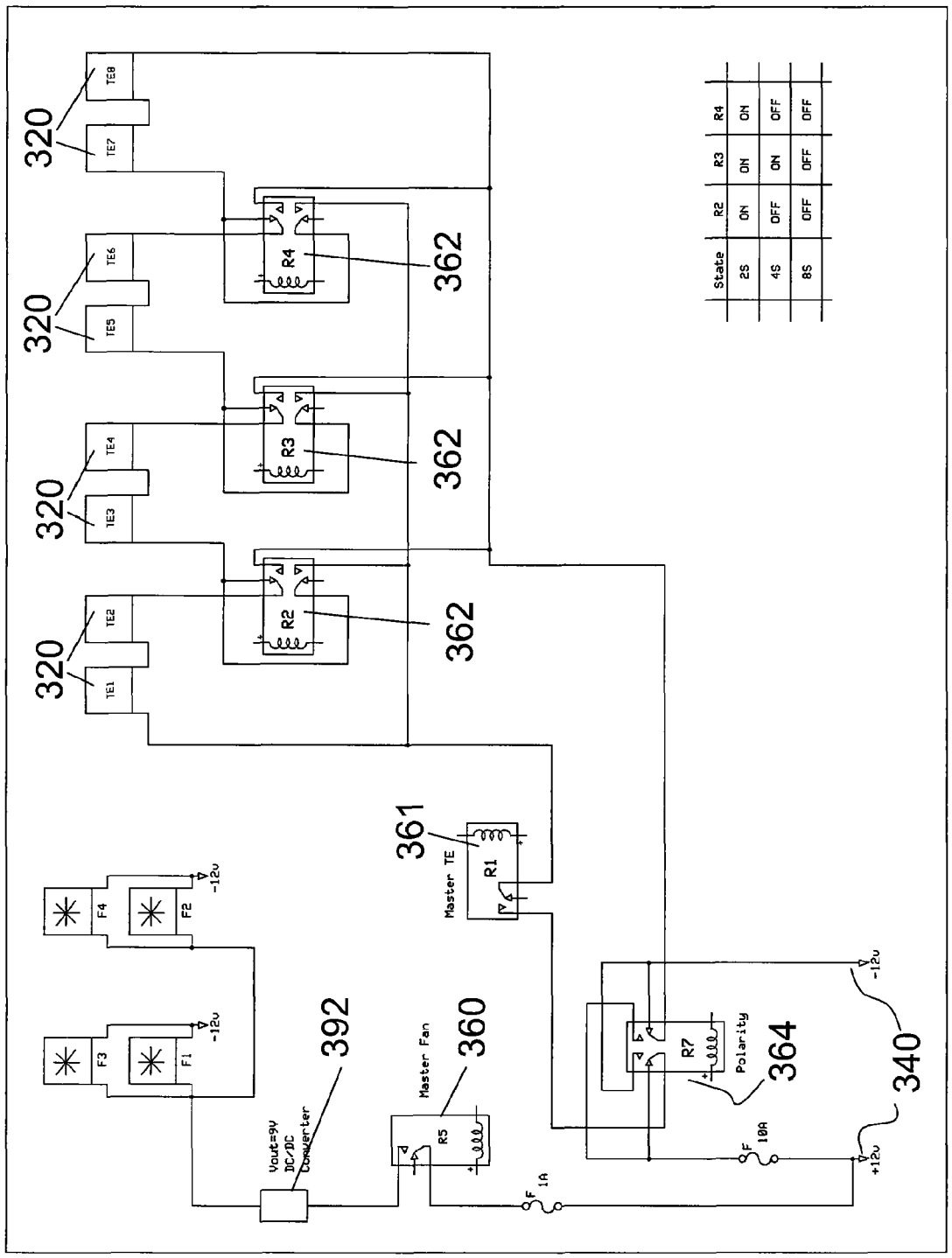
FIG. 19 shows an electrical schematic view, illustrating an alternately preferred electrical control of a thermoelectric heat pump assembly, according to the preferred embodiment of the invention.

FIGS. 19-22 show wiring diagrams for the temperature control subroutines conveyed by microprocessor 350 to relays 360-364 for thermoelectric transport or storage device 102. For example, FIG. 19 shows DPDT master relay 361 and multiple DPDT relays 362 configured in a 2S-2.4 volt mode such as when Tc>(Tsp+0.3° C.) and wherein one relay 362 is in the on-position for 4S mode. In addition, FIG. 19 shows DC-to-DC converter 392 in connection with fan DPDT latching relay 361 which is in connection with battery charge DPDT standard relay 364. DPDT relays 362 receive instructions from master DPDT latching relay 361 which places DPDT relays 362 in 2S&4S mode as well as thermoelectric unit layers 320, wherein the thermoelectric transport or storage device 102 comprises 8 thermoelectric unit layers 320.

Figure 20:
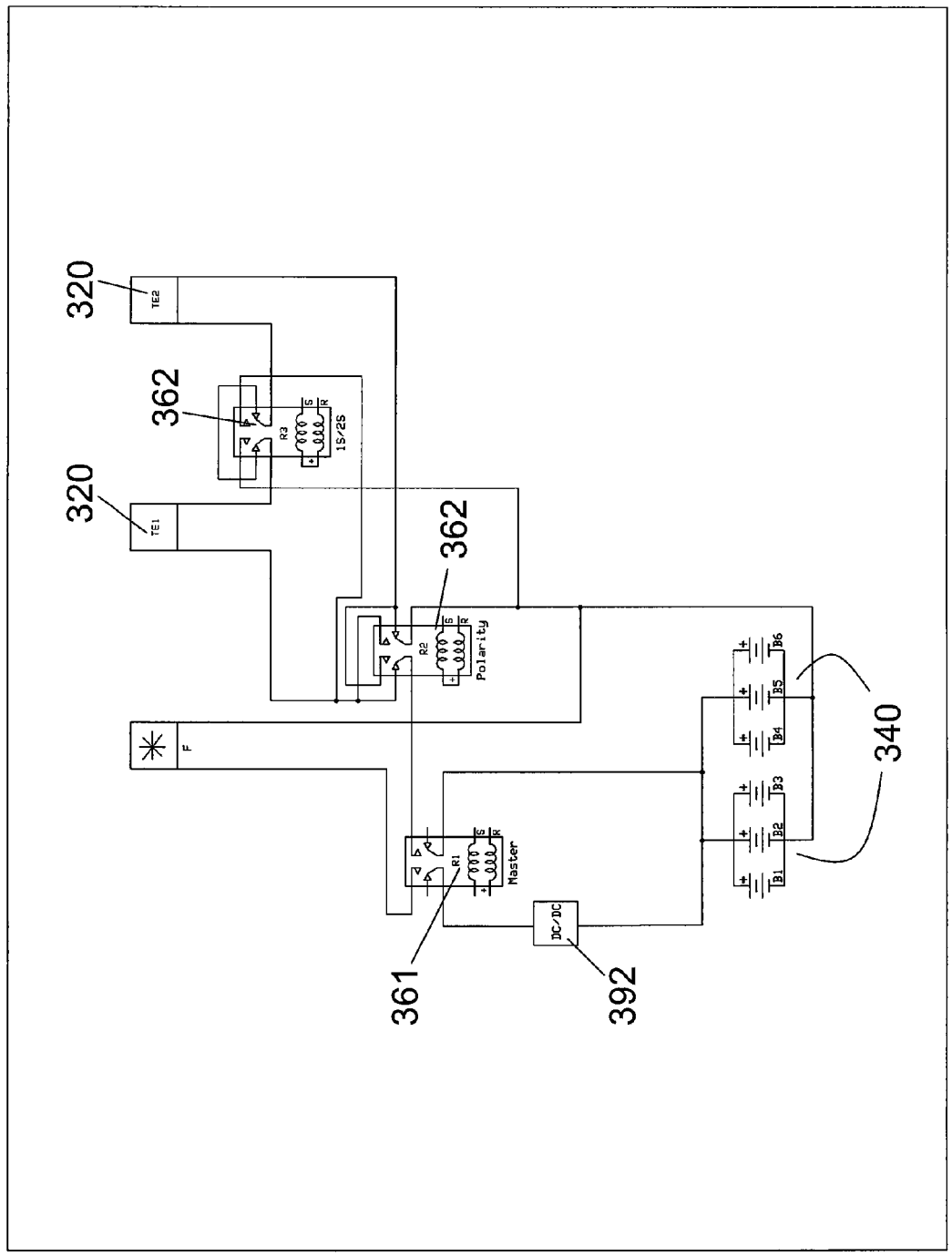
FIG. 20 shows an electrical schematic view, illustrating an alternately preferred electrical control of a thermoelectric heat pump assembly, according to the preferred embodiment of the invention.
Figure 21:
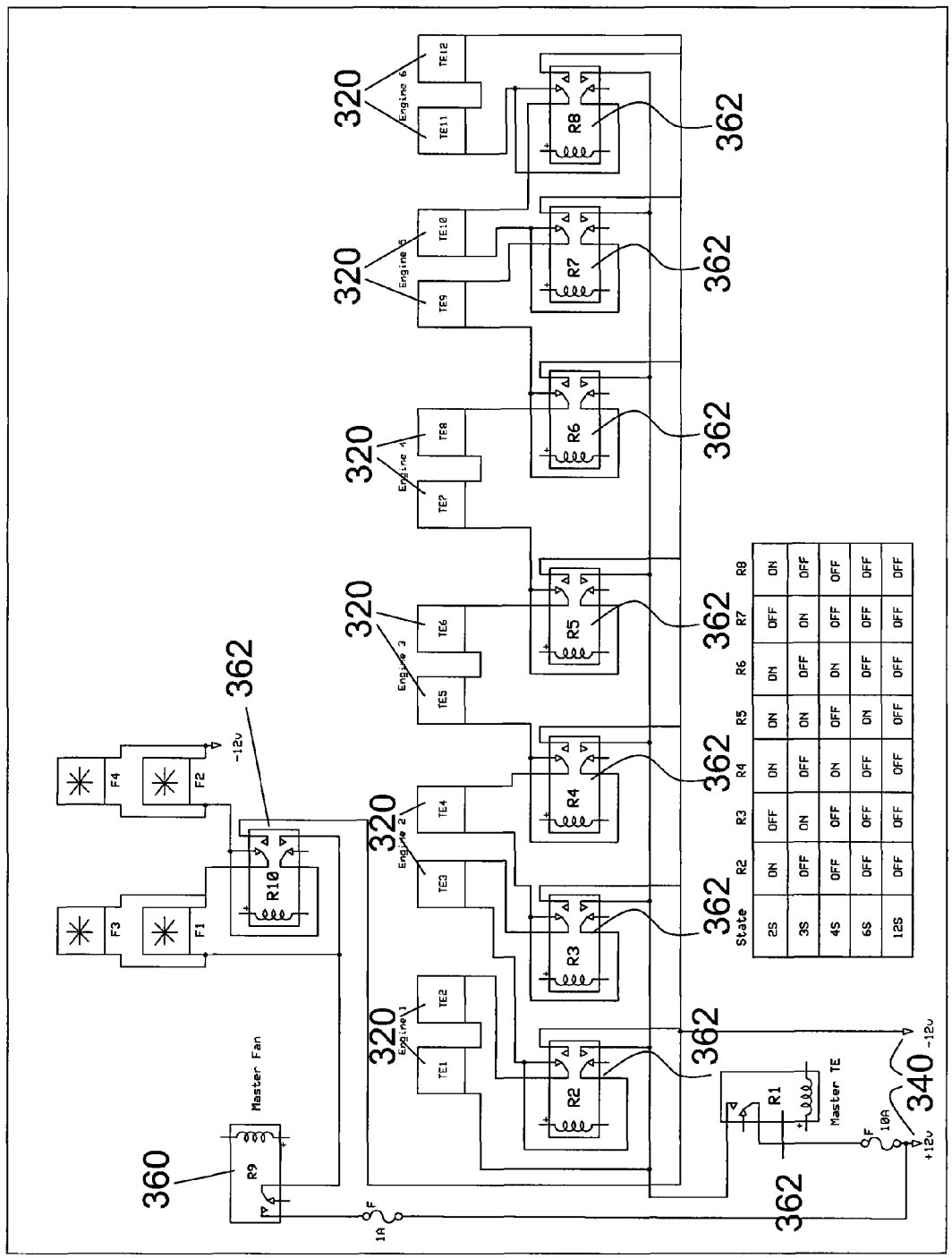
FIG. 21 shows an electrical schematic view, illustrating an alternately preferred electrical control of a thermoelectric heat pump assembly, according to the preferred embodiment of the invention.

Similar to FIG. 19, FIGS. 20-21 also show different modes relating to different scenarios involving 2 to 12 thermoelectric unit layers 320. For example, FIG. 20 shows the wiring diagram for a thermoelectric transport or storage device 120 comprising 2 thermoelectric unit layers 320. FIG. 21 shows the wiring diagram for a thermoelectric transport or storage device 120 comprising 12 thermoelectric unit layers 320. As shown in FIG. 21, utilizing 12 thermoelectric unit layers 320 allows thermoelectric transport or storage device 102 to switch between 2S, 3S, 4S, 6S, and 12S mode.

Figure 22:
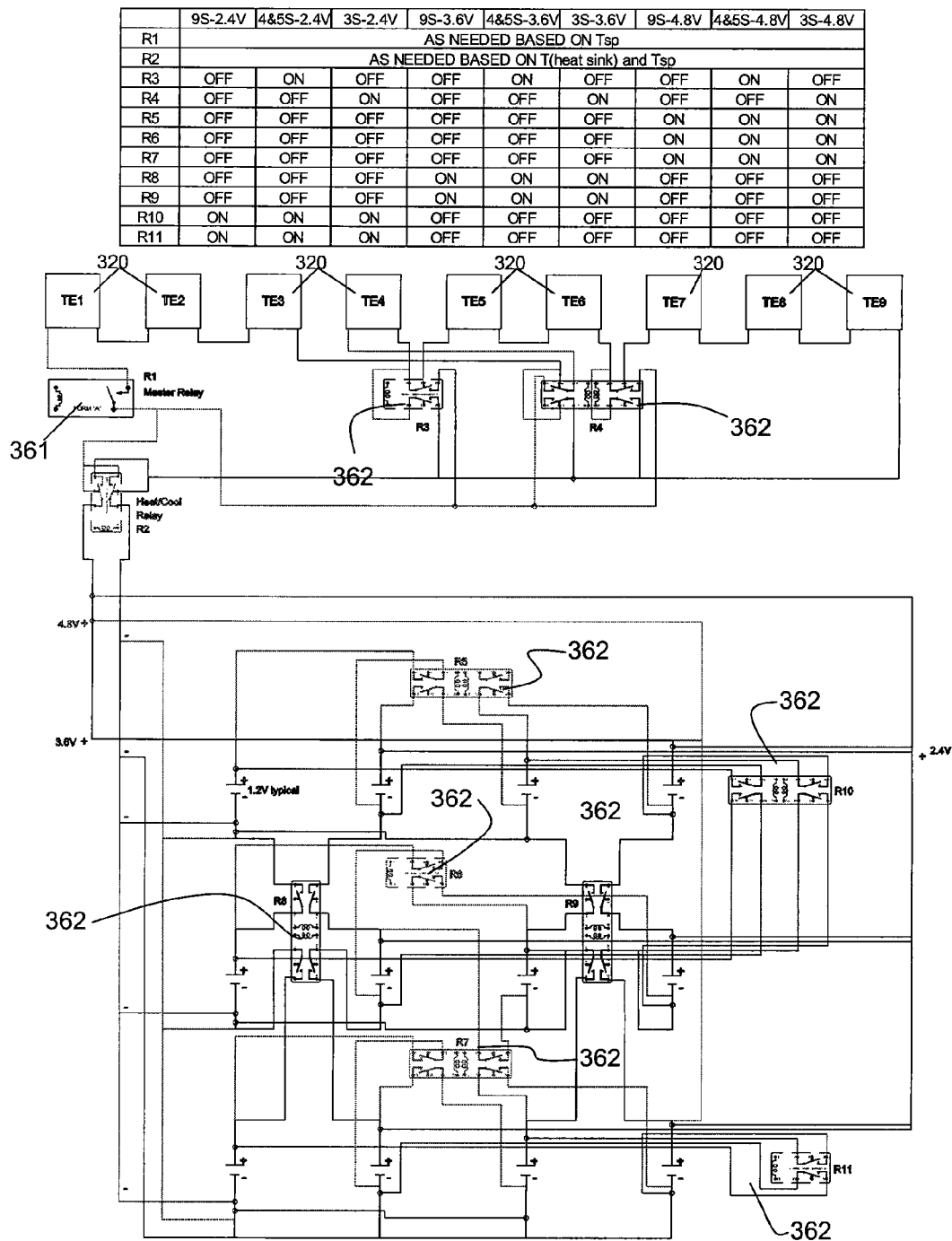
FIG. 22 shows an electrical schematic view, illustrating an alternately preferred electrical control of a thermoelectric heat pump assembly, according to the preferred embodiment of the invention.

More specifically, FIG. 22 shows which DPDT relays 362 (labeled R1-R11) are in the on and off position relating to a specific mode for a thermoelectric transport or storage device 120 comprising 9 thermoelectric unit layers 320. For example, in a 9S-2.4 volt mode R3-R9 are in the off-position, R10 and R11 are in the on-position. In a 4&5S-2.4 volt mode R4-R9 are in the off-position, R3, R10 and R11 are in the on-position. In a 3S-2.4 volt mode R3 and R5-R9 are in the off-position, R4, R10 and R11 are in the on-position. In a 9S-3.6 volt mode R3-R7, R10, and R11 are in the off-position, R8 and R9 are in the on-position. In a 4&5S-3.6 volt mode R4-R7, R10 and R11 are in the off-position, R3, R8 and R9 are in the on-position. In a 3S-3.6 volt mode R3, R5-R7, R10 and R11 are in the off-position, and R4, R8, and R9 are in the on-position. In a 9S-4.8 volt mode R3, R4 and R8-R10 are in the off-position, and R5-R7 are in the on-position. In a 4&5S-4.8 volt mode R4 and R8-R11 are in the off-position, and R3, as well as R5-R7 are in the on-position. In a 3S-4.8 volt mode R3 and R8-11 are in the off-position, and R4-R7 are in the on-position. In the various forgoing modes for FIG. 22, R1 and R2 are utilized depending on the Tsp and heat sink. Switching thermoelectric unit layers 320 between modes allows the thermoelectric transport or storage device 102 to more efficiently utilize energy source 340.

Figure 23:
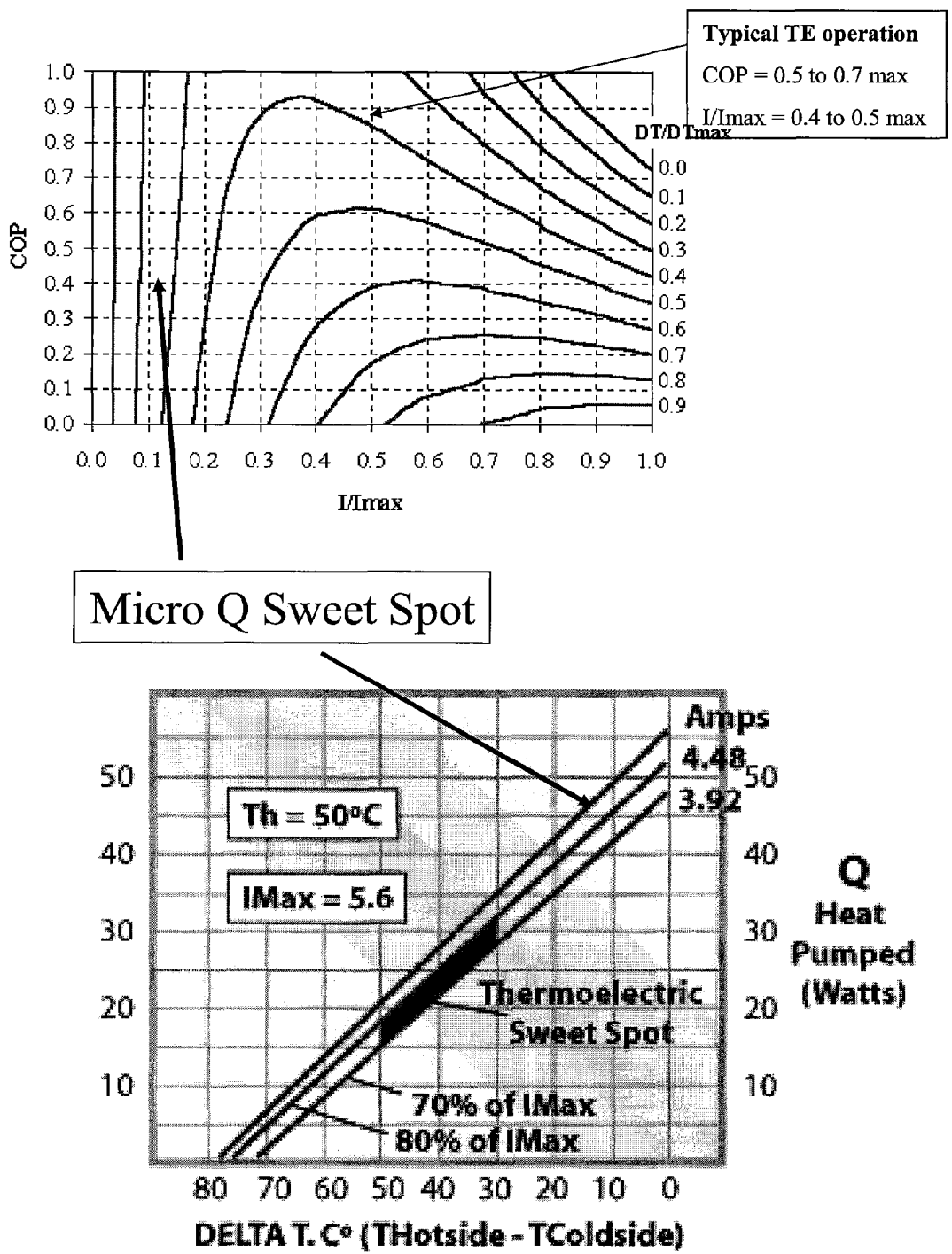
FIG. 23 shows two charts, each of which illustrate how preferred embodiments of the present invention are configured to maximize efficiency of operation compared to previously available thermoelectric heat pump systems; the charts further illustrate how the preferred embodiments of the present invention are configured to maximize heat pumped per unit of input power during overall use.

FIG. 23 shows two charts, each of which illustrate how preferred embodiments of the present invention are configured to maximize efficiency of operation compared to previously available thermoelectric heat pump systems. For example, preferred embodiments of the heat pump assembly of the invention is configured so that each thermoelectric unit layer at steady-state during operation has ratio of the heat removed divided by the input power (COP) that is prior to and less than the peak COP on a COP curve of performance (See infra FIGS. 29A-C and 30A-C).

Figure 24A:
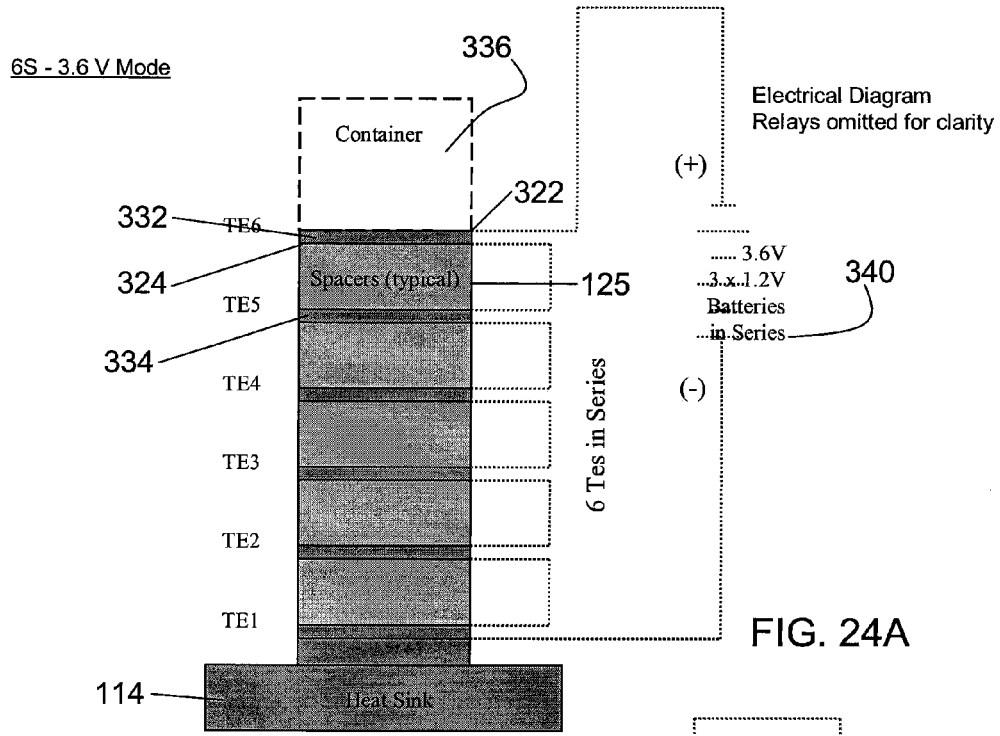
FIGS. 24A-B show an electrical schematic view, illustrating a preferred embodiment of the present invention, wherein the thermoelectric heat pump assembly contains six thermoelectric unit layers, and wherein the thermoelectric unit layers are reconfigurable between a higher power setting and a lower power setting, and series and/or parallel configurations.
Figure 24B:
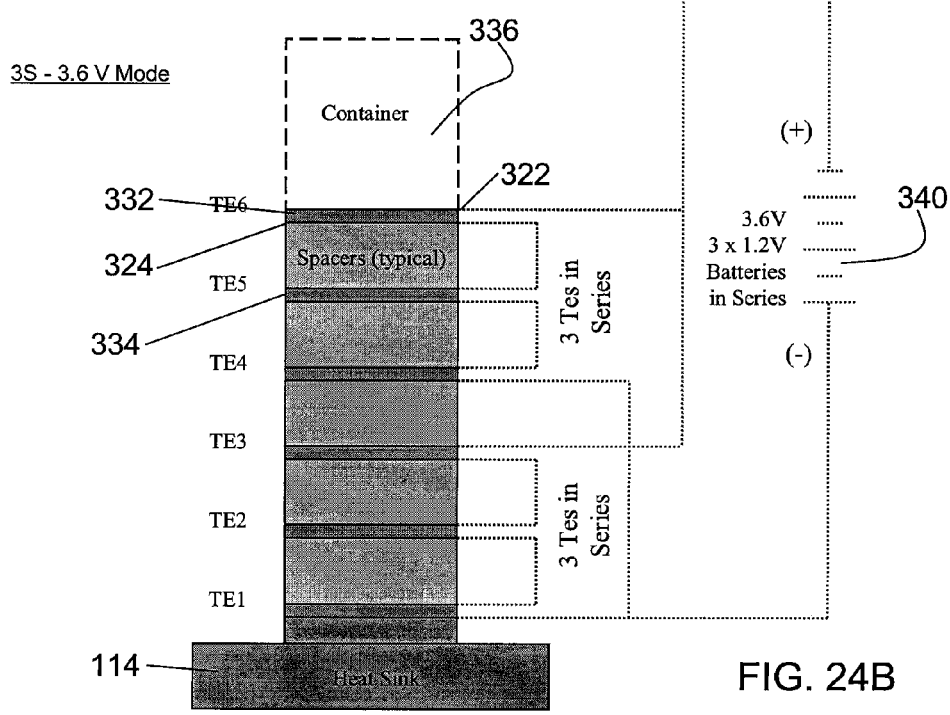

FIGS. 24A-27 show the thermoelectric unit layers 320 of thermoelectric transport or storage device 102. More specifically, FIG. 24A shows a 6 layer thermoelectric unit layer 320 in series, as well as in 6S-3.6 volt mode wherein thermoelectric unit layers 320 receive current from energy source 340 in order to create a heat pump which draws heat from thermal isolation chamber 336 to heat sink 114. Each thermoelectric layer 320 comprises capacitance spacer block 125, cold side 322 of thermoelectric unit layer 320, and hot side 324 of thermoelectric unit layer 320, wherein first thermoelectric unit layer 332 is adjacent to thermal isolation chamber 336. In the 6S-3.6 volt mode heat is transferred from thermal isolation chamber 336 to heat sink 114. Similar to FIG. 24A, FIG. 24B shows a 6 layer thermoelectric unit layer 320. However, FIG. 24B shows the 6 layer thermoelectric unit layer 320 wherein 3 thermoelectric unit layers 320 are in 2 sets of series, corresponding to a 3S-3.6 volt mode.

Figure 25A:
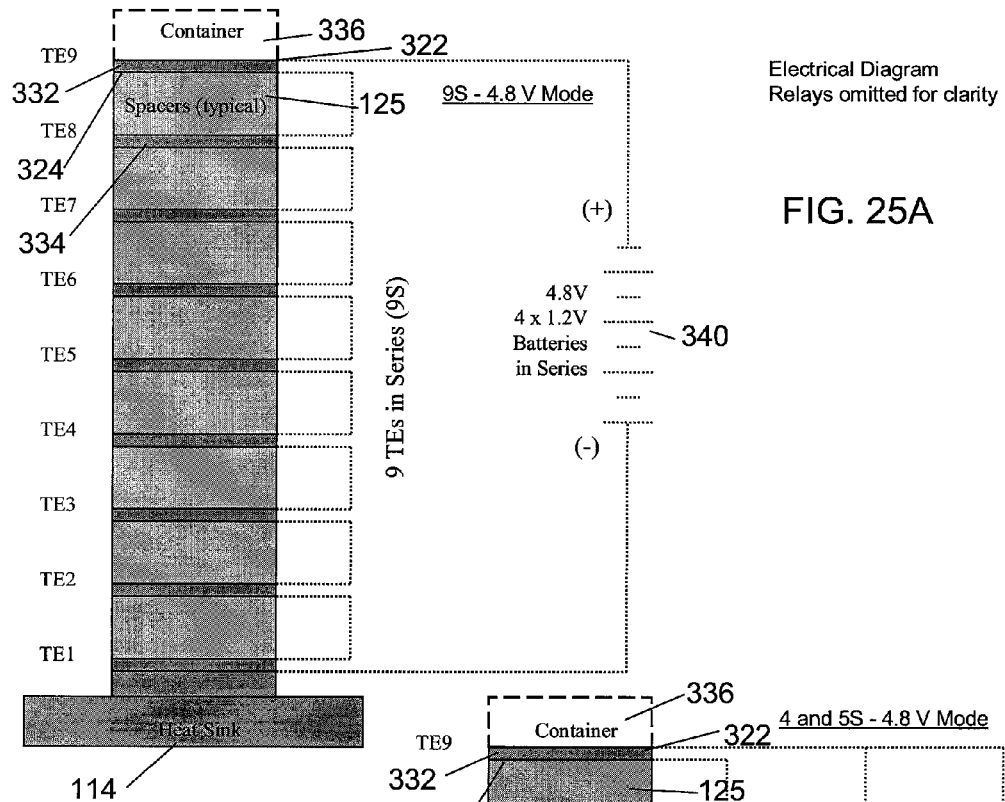
FIG. 25 shows an electrical schematic view, illustrating a preferred embodiment of the present invention, wherein the thermoelectric heat pump assembly contains nine thermoelectric unit layers, and wherein the thermoelectric unit layers are reconfigurable between a higher power setting and a lower power setting, and series and/or parallel configurations.
Figure 25B:
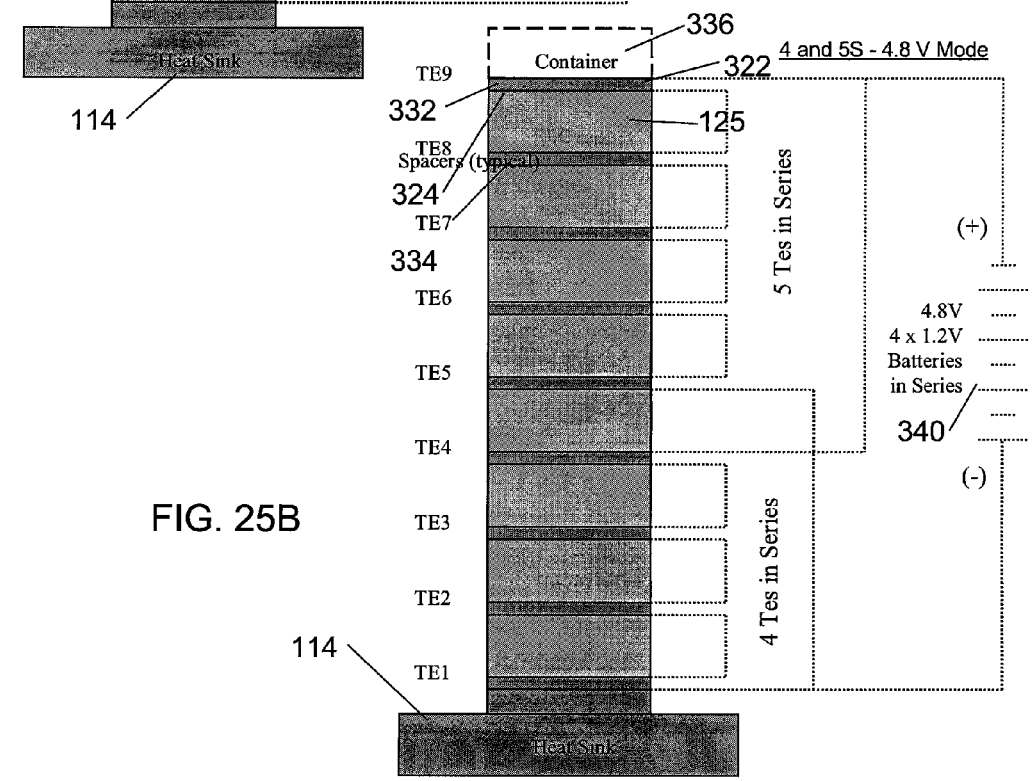
Figure 26A:
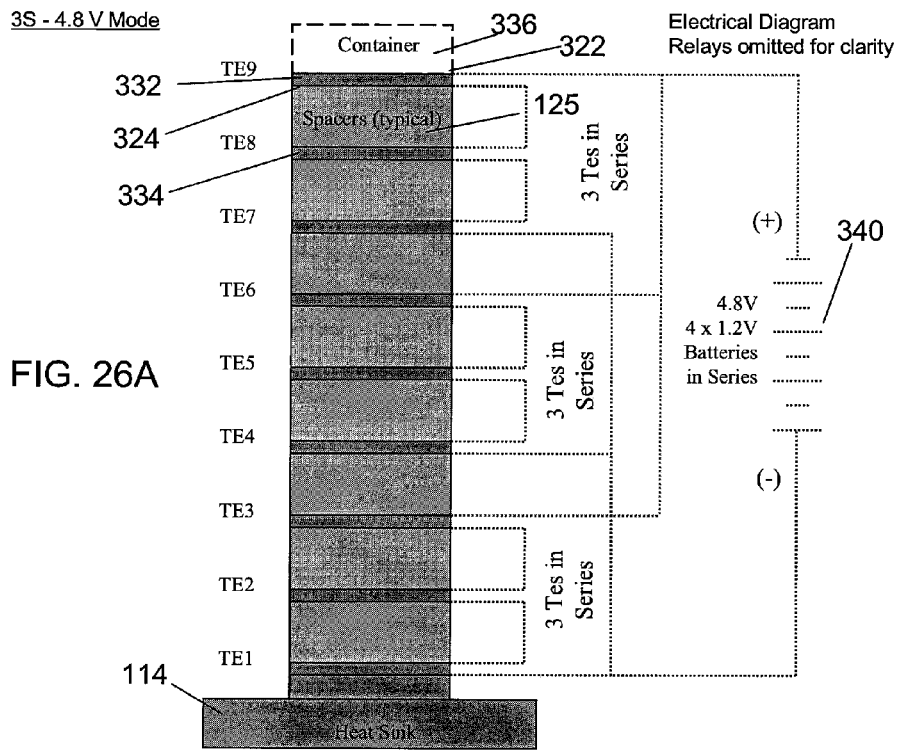
FIG. 26 shows: 1) in the top figure, an electrical schematic view, illustrating a preferred embodiment of the present invention, wherein the thermoelectric heat pump assembly contains nine thermoelectric unit layers, and wherein the thermoelectric unit layers are reconfigurable between a higher power setting and a lower power setting, and series and/or parallel configurations; and 2) in the bottom figure, an electrical schematic view, illustrating a preferred embodiment of the present invention, wherein the thermoelectric transport and storage device contains at least two thermoelectric heat pump assemblies.
Figure 26B:
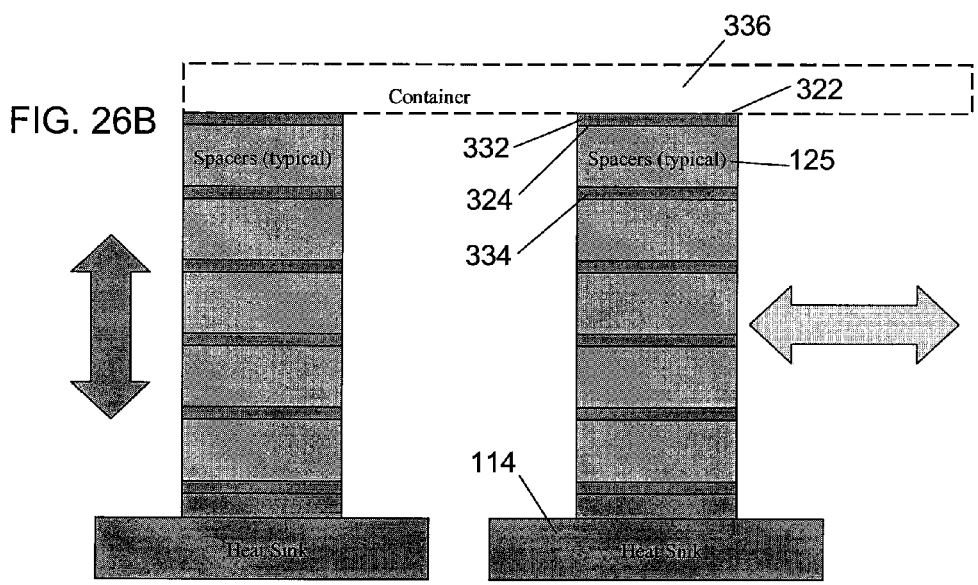

FIGS. 25A and 25B show 9 layer thermoelectric unit layer 320 stacks. In FIG. 25A all 9 thermoelectric unit layers 320 are in series and correspond to a 9S-4.8 volt mode. In FIG. 25B the 9 layer thermoelectric unit layers 320 are broken into one set of 5 thermoelectric unit layers in series and one set of 4 thermoelectric unit layers in series, corresponding to a 4&5S-4.8 volt mode. FIG. 26A shows the 9 layer thermoelectric unit layer 320 stack in three sets of 3 thermoelectric unit layers in series.

Figure 27A:
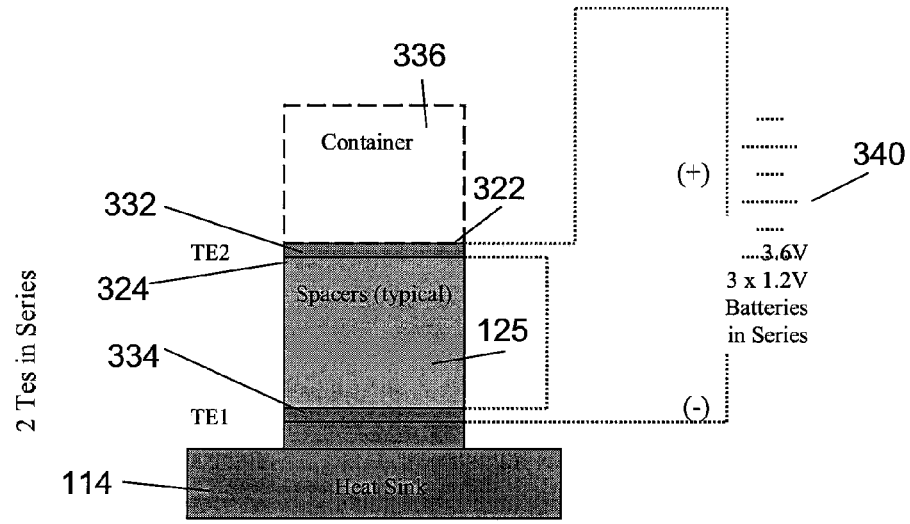
FIG. 27 shows an electrical schematic view, illustrating a preferred embodiment of the present invention, wherein the thermoelectric heat pump assembly contains two thermoelectric unit layers, and wherein the thermoelectric unit layers are reconfigurable between a higher power setting and a lower power setting, and series and/or parallel configurations.
Figure 27B:
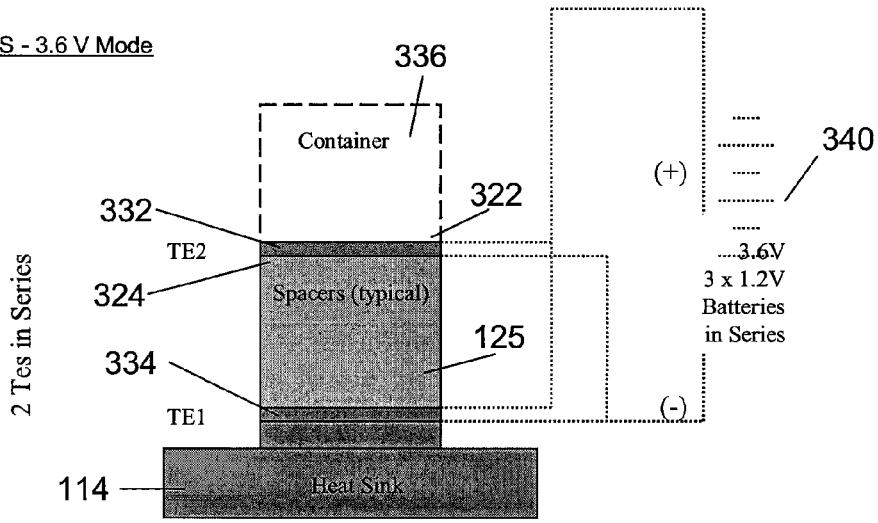

FIG. 26A shows how the thermoelectric unit layer 320 stacks may be placed in parallel when one thermoelectric unit layer 320 stack is not sufficient. FIGS. 27A and 27B show a 2 layer thermoelectric unit layer 320 wherein FIG. 27A is in 2S-3.6 volt mode and FIG. 27B is in 1S-3.6 volt mode. As previously stated, switching thermoelectric unit layers 320 between modes allow the thermoelectric transport or storage device 102 to more efficiently utilize energy source 340 while maintaining a desired Tc.

Figure 29A:
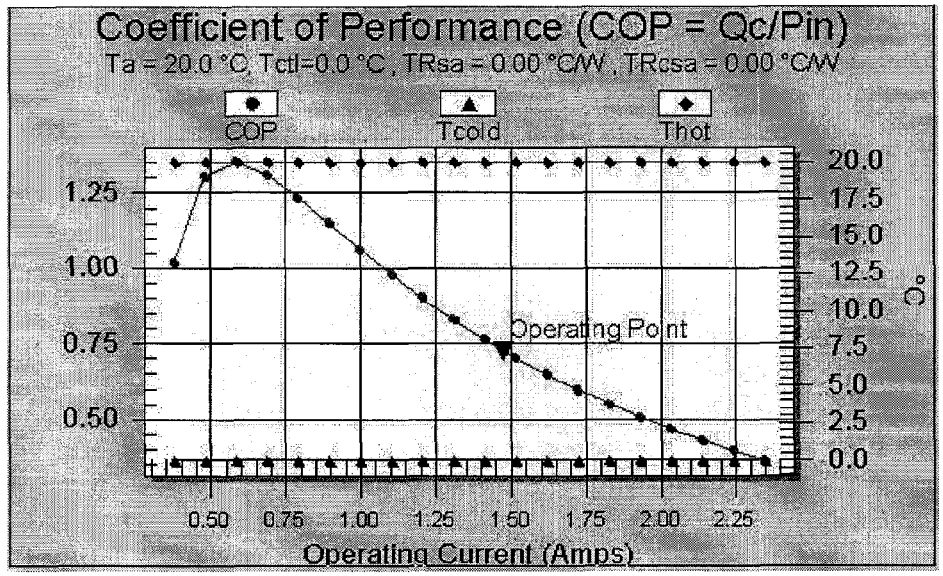
FIGS. 29A-C show charts, illustrating how preferred embodiments of the present invention are configured to maximize efficiency of operation compared to typical thermoelectric heat pump systems; the charts further illustrate how the preferred embodiments of the present invention are configured to maximize heat pumped per unit of input power during overall use, while minimizing the ratio of input current to maximum available current at a given steady-state temperature.
Figure 29B:
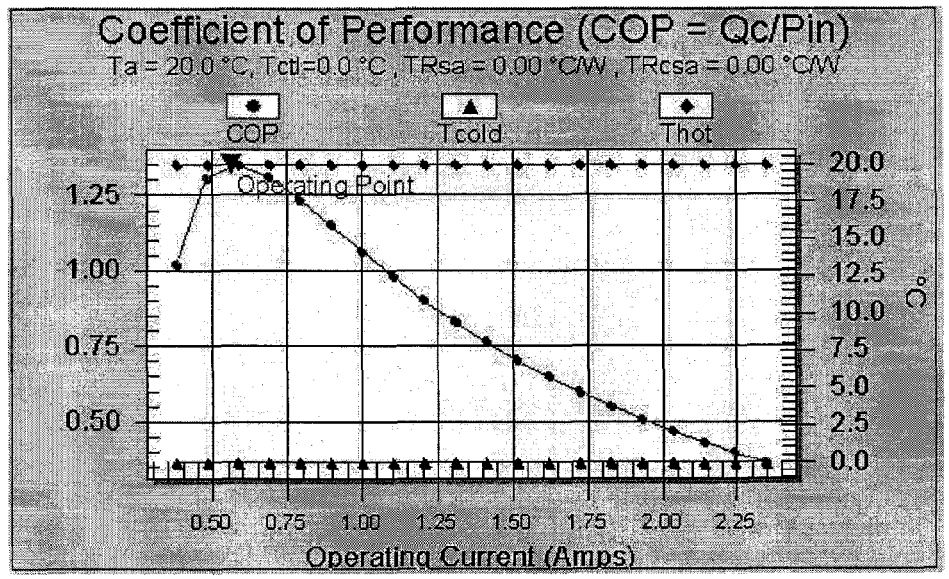
Figure 29C:
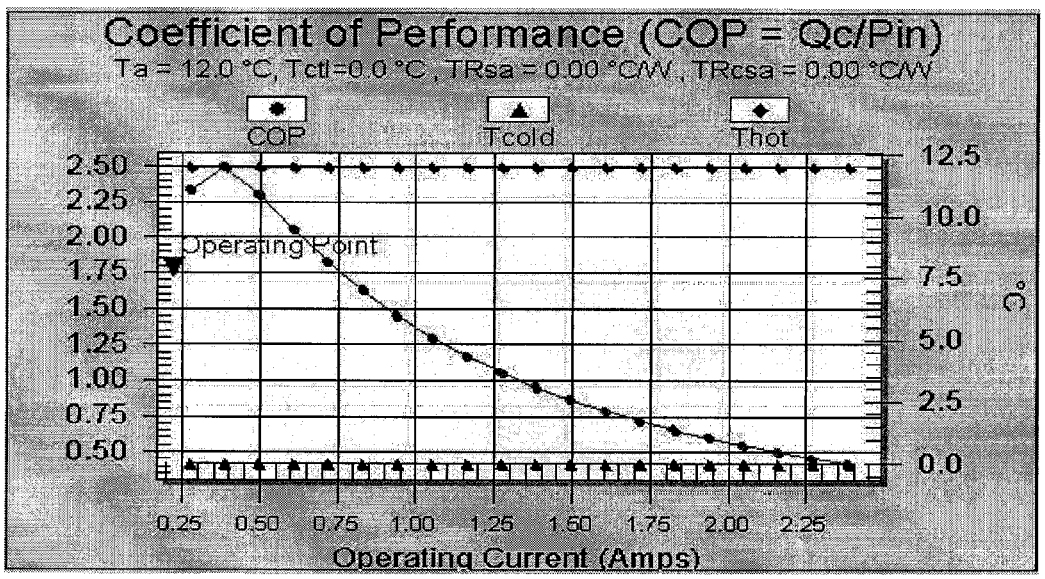
Figure 30A:
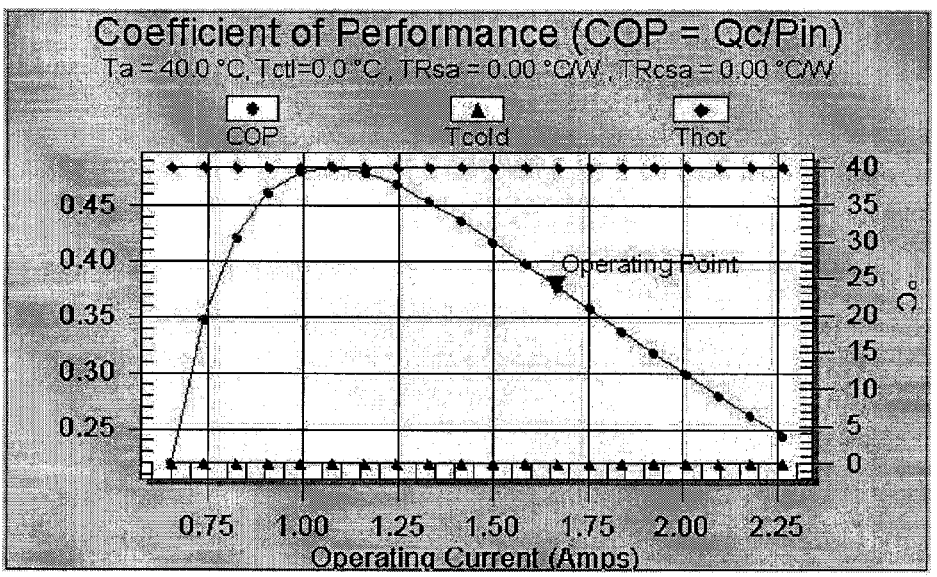
FIGS. 30A-C show charts, illustrating how preferred embodiments of the present invention are configured to maximize efficiency of operation compared to typical thermoelectric heat pump systems; the charts further illustrate how the preferred embodiments of the present invention are configured to maximize heat pumped per unit of input power during overall use, while minimizing the ratio of input current to maximum available current at a given steady-state temperature.
Figure 30B:
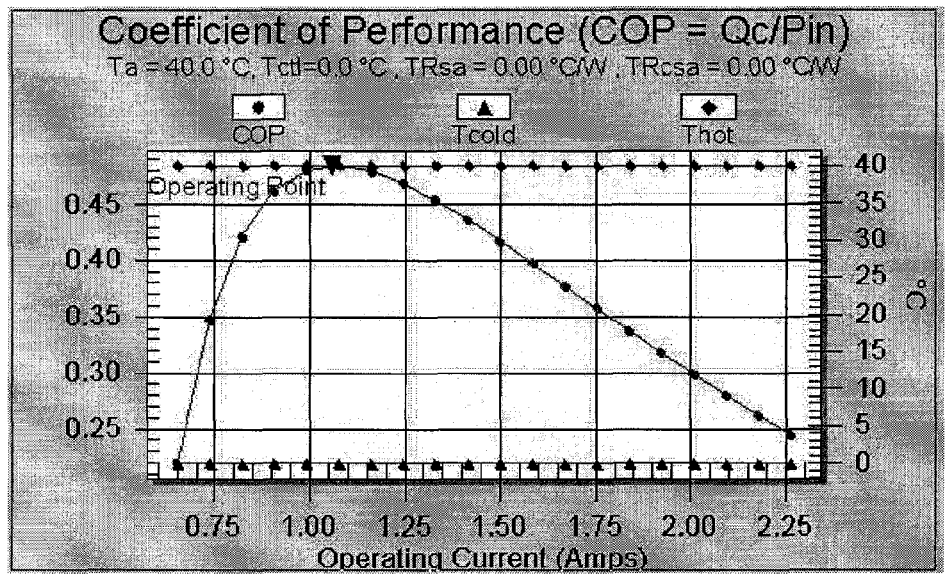
Figure 30C:
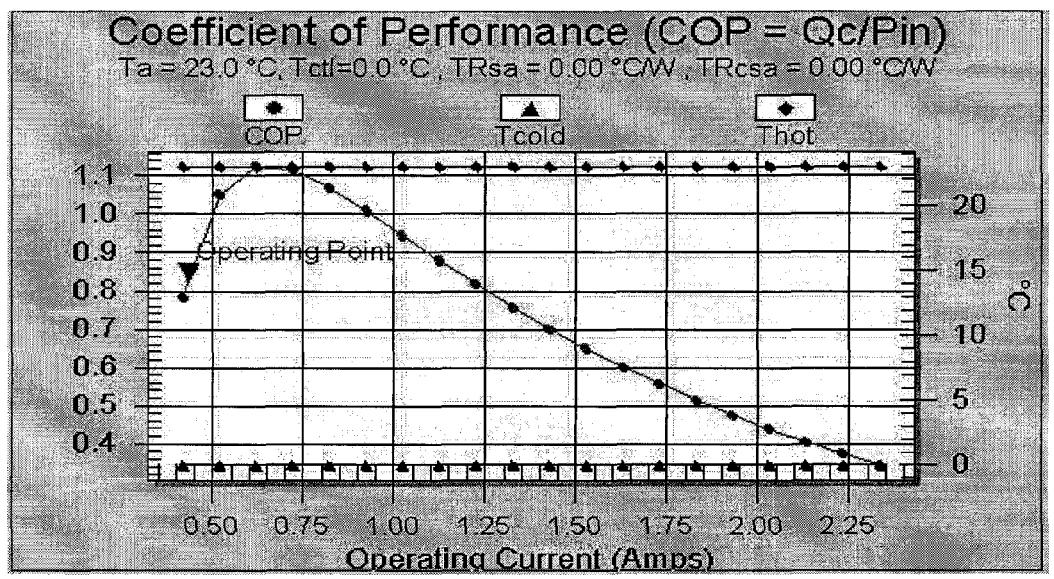

FIGS. 28A and 28B further emphasize advantages of thermoelectric transport or storage device 102, (see FIG. 13B), wherein the maximum current, current, maximum Delta-T, Delta-T, transferred heat, voltage, ratio of current to maximum current, ratio of Delta-T to maximum Delta-T, are displayed. FIG. 28A further shows the 1S mode and 2S mode at Delta-T of 20.9° C. and 39.4° C. Likewise, FIG. 28B shows a 1S and 2S mode at Delta-T of 10° C., 20° C. and 40° C. However, FIG. 28B defines values for heat transferred Q. FIG. 29A shows a graph of a typical operating point coefficient of performance at a Delta-T of 20° C., wherein Delta-T is the temperature difference between thermal isolation chamber 336 and heat sink 114. The coefficient of performance is defined as the amount of heat transferred from thermal isolation chamber 336 divided by the amount of power (voltage multiplied by current) required to operate thermoelectric transport or storage device 102. FIG. 29B further shows the optimum operating point coefficient of performance at a Delta-T of 20° C. which corresponds to FIG. 29C showing the operating point coefficient of performance of thermoelectric transport or storage device 102. As shown in FIG. 29A through FIG. 29C the operating point coefficient of performance for thermoelectric transport or storage device 102 is well above the typical operating point coefficient of performance. That is, thermoelectric transport or storage device 102 is able to pump more heat from thermal isolation chamber 336 to heat sink 114 using less current and ultimately less power than typical thermoelectric systems. Further improvements over typical thermoelectric systems was also shown in FIG. 30A through FIG. 30C at a Delta-T of 40° C.

Although applicant has described applicant's preferred embodiments of this invention, it will be understood that the broadest scope of this invention includes modifications. Such scope is limited only by the below claims as read in connection with the above specification. Further, many other advantages of applicant's invention will be apparent to those skilled in the art from the above descriptions and the below claims.

What is claimed is:

1. A thermoelectric heat pump assembly having a top end and a bottom end, the thermoelectric heat pump assembly comprising:
   (a) two to nine thermoelectric unit layers capable of active use of the Peltier effect, each thermoelectric unit layer having a cold side and a hot side;
   (b) at least one capacitance spacer block that stores heat and provides a buffer to delay transfer of heat from one thermoelectric unit layer to another, the capacitance spacer block having a top portion and a bottom portion and being between a first thermoelectric unit layer and a second thermoelectric layer, wherein the top portion of the capacitance spacer block is thermally connected to the hot side of the first thermoelectric unit layer and the bottom portion is thermally connected to the cold side of the second thermoelectric unit layer, thereby forming a sandwich layer that pumps heat from the first thermoelectric unit layer to the second thermoelectric layer;
   (c) at least one energy source operably connected to each thermoelectric unit layer, wherein the energy source is suitable to provide a current, the thermoelectric heat pump assembly being configured so that each individual thermoelectric unit layer has a ratio of input current to maximum available current (I/Imax) of 0.09 or less at a steady-state when a change in temperature ($\Delta T$) of the heat pump assembly at the top end compared to the bottom end of the heat pump assembly is about 20° C. and heat removal (Q) is about 0 Watts; and
   (d) a heat sink associated with a fax assembly, wherein the heat sink is thermally connected at the bottom end of the heat pump assembly.

2. A thermoelectric heat pump assembly having a top end and a bottom end, the thermoelectric heat pump assembly comprising:
   (a) two to nine thermoelectric unit layers capable of active use of the Peltier effect, each thermoelectric unit layer having a cold side and a hot side;
   (b) at least one capacitance spacer block that stores heat and provides a buffer to delay transfer of heat from one thermoelectric unit layer to another, the capacitance spacer block having a top portion and a bottom portion and being between a first thermoelectric unit layer and a second thermoelectric layer, wherein the top portion of the capacitance spacer block is thermally connected to the hot side of the first thermoelectric unit layer and the bottom portion is thermally connected to the cold side of the second thermoelectric unit layer, thereby forming a sandwich layer that pumps heat from the first thermoelectric unit layer to the second thermoelectric layer;
   (c) at least one energy source operably connected to each thermoelectric unit layer, wherein the energy source is suitable to provide a current; and
   (d) a heat sink associated with a fan assembly, wherein the heat sink is thermally connected at the bottom end of the heat pump assembly, the heat pump assembly being configured to minimize a temperature rise or drop on the heat sink at a steady-state so that the temperature rise or drop on the heat sink does not exceed 3° Celsius as compared to ambient.

3. A thermoelectric heat pump assembly having a top end and a bottom end, the thermoelectric heat pump assembly comprising:
   (a) two to nine thermoelectric unit layers capable of active use of the Peltier effect, each thermoelectric unit layer having a cold side and a hot side;
   (b) at least one capacitance spacer block that stores heat and provides a buffer to delay transfer of heat from one thermoelectric unit leer to another, the capacitance spacer block having a top portion and a bottom portion and being between a first thermoelectric unit layer and a second thermoelectric layer, wherein the top portion of the capacitance spacer block is thermally connected to the hot side of the first thermoelectric unit layer and the bottom portion is thermally connected to the cold side of the second thermoelectric unit layer, thereby forming a sandwich layer that pumps heat from the first thermoelectric unit layer to the second thermoelectric layer;
   (c) at least one energy source operably connected to each thermoelectric unit layer, wherein the energy source is suitable to provide a current;
   (d) a heat sink associated with a fan assembly, wherein the heat sink is thermally connected at the bottom end of the heat pump assembly; and
   (e) a microcontroller operatively associated with the energy source and at least one relay, wherein the microcontroller activates the relay which directs current from the energy source to at least one of the thermoelectric unit layers and reconnects the thermoelectric unit layer in series or parallel with another thermoelectric unit layer.

4. The thermoelectric heat pump assembly of claim 3, wherein the microcontroller defines a setpoint temperature (Tsp) and compares the Tsp to a temperature (Tc) of a container operatively associated with the thermoelectric heat pump assembly, wherein the microcontroller controls the at least one relay to connect the at least one thermoelectric unit layer in series if Tc checks positive or equal against Tsp, and wherein the microcontroller deactivates the at least one relay if Tsp checks negative or equal against Tc.

5. The thermoelectric heat pump assembly of claim 3, wherein the microcontroller defines a setpoint temperature (Tsp) and compares the Tsp to a temperature (Tc) of a container operatively associated with the thermoelectric heat pump assembly, wherein the microcontroller activates the at least one relay to connect the at least one thermoelectric unit layer in parallel if Tc checks positive or equal against Tsp, and wherein the microcontroller deactivates the at least one relay if Tsp checks negative or equal against Tc.

6. The thermoelectric heat pump assembly according to claim 5, wherein the Tc checks positive or equal if the Tc is greater than the Tsp plus 0.1° C., and wherein the at least one thermoelectric unit layer is in series and the energy source provides a potential difference of about 2.4 volts.

7. The thermoelectric heat pump assembly of claim 3, wherein the thermoelectric heat pump assembly is configured so that each individual thermoelectric unit layer has a ratio of input current to maximum available current (I/Imax) of 0.08 or less at a steady-state when a change in temperature ($\Delta T$) of the heat pump assembly at the top end compared to the bottom end of the heat pump assembly is about 20° C. and heat (Q) is about 0 Watts.

8. The thermoelectric heat pump assembly of claim 3, wherein the thermoelectric heat pump assembly is configured so that each individual thermoelectric unit layer has a ratio of input current to maximum available current (I/Imax) of 0.10 or less, when change in temperature ($\Delta T$) of the heat pump assembly at the top end compared to the bottom end of the heat pump assembly is about 20° C. and heat (Q) is about 5 Watts.

9. The thermoelectric heat pump assembly of claim 3, wherein the thermoelectric heat pump assembly is configured so that each individual thermoelectric unit layer has a ratio of input current to maximum available current (I/Imax) of 0.17 or less at a steady-state when a change in temperature (ΔT) of the heat pump assembly at the top end compared to the bottom end of the heat pump assembly is about 40° C. and heat (Q) is about 0 Watts.

10. The thermoelectric heat pump assembly of claim 3, wherein the thermoelectric heat pump assembly is configured so that each individual thermoelectric unit layer has a ratio of input current to maximum available current (I/Imax) of 0.22 or less, when change in temperature (ΔT) of the heat pump assembly at the top end compared to the bottom end of the heat pump assembly is about 40° C. and heat (Q) is about 1 Watt.

11. The thermoelectric heat pump assembly of claim 3, wherein the heat pump assembly is configured to minimize a temperature rise or drop on the heat sink at a steady-state so that the temperature rise or drop on the heat sink does not exceed 2.5° Celsius.

12. The thermoelectric heat pump assembly of claim 3, wherein each thermoelectric unit layer comprises at least 127 coupled pairs of thermoelectric units and has a heat pumping capability of between 15 Watts and 20 Watts.

13. The thermoelectric heat pump assembly of claim 3, wherein each thermoelectric unit layer comprises thermoelectric units electrically connected in parallel or series, but thermally connected in series.

14. The thermoelectric heat pump assembly of claim 3, wherein each thermoelectric unit layer in the heat pump assembly is separated by a capacitance spacer block.

15. The thermoelectric heat pump assembly of claim 3, wherein the number of thermoelectric unit layers is three to nine.

16. The thermoelectric heat pump assembly of claim 3, wherein the thermoelectric heat pump assembly includes programmable circuitry suitable for a user-selected temperature input.

17. The thermoelectric heat pump assembly of claim 3, wherein each thermoelectric unit layer has a maximum change in temperature (ΔTmax) potential and comprises at least 127 coupled pairs of thermoelectric units, and wherein the heat pump assembly is configured so that each thermoelectric layer operates at less than 20% of the ΔTmax at steady-state when a change in temperature (ΔT) of the heat pump assembly at the top end compared to the bottom end of the heat pump assembly is 20° C.

18. The thermoelectric heat pump assembly of claim 3, wherein each thermoelectric unit layer has a maximum change in temperature (ΔTmax) potential and comprises at least 127 coupled pairs of thermoelectric units, and wherein the heat pump assembly is configured so that each thermoelectric layer operates at less than 40% of the ΔTmax at steady-state when a change in temperature (ΔT) of the heat pump assembly at the top end compared to the bottom end of the heat pump assembly is 40° C.

19. A method of safely transporting temperature sensitive goods at a selected temperature profile during transport, comprising the steps of:
  (a) placing the temperature sensitive goods in a transportation device adapted to thermally isolate the temperature sensitive goods from an outside environment, wherein the transportation device comprises at least one temperature control system adapted to actuate the selected temperature profile while the temperature sensitive goods are in the transportation device, the temperature control system comprising at least one thermoelectric heat pump of claim 4 in thermal association with the temperature sensitive goods being transported; and
  (b) transporting the temperature sensitive goods while the transportation device is activated according to the selected temperature profile.

20. The method of claim 19, wherein the transportation device comprises at least four thermoelectric heat pumps thermally associated with the temperature sensitive goods being transported.

* * * * *